(12) United States Patent
Schmidt et al.

(10) Patent No.: US 6,485,797 B1
(45) Date of Patent: Nov. 26, 2002

(54) 5-ARYLINDANE DERIVATIVES AND FERROELECTRIC LIQUID CRYSTAL MIXTURE CONTAINING SAME

(75) Inventors: Wolfgang Schmidt, Dreieich (DE); Javier Manero, Liederbach (DE); Barbara Hornung, Hasselroth (DE); Rainer Wingen, Hattersheim (DE); Ayako Ogawa, Kakegawa (JP)

(73) Assignee: Aventis Research & Technologies GmbH & Co. KG, Frankfurt am Main (DE)

( * ) Notice: Subject to any disclaimer, the term of this patent is extended or adjusted under 35 U.S.C. 154(b) by 0 days.

(21) Appl. No.: 09/509,602

(22) PCT Filed: Oct. 8, 1999

(86) PCT No.: PCT/EP98/06415

§ 371 (c)(1),
(2), (4) Date: Aug. 31, 2000

(87) PCT Pub. No.: WO99/19420

PCT Pub. Date: Apr. 22, 1999

(30) Foreign Application Priority Data

Oct. 10, 1997 (EP) .............................. 97117536
Sep. 4, 1998 (DE) ......................... 198 40 447

(51) Int. Cl.[7] ................ C09K 19/34; C09K 19/32; C07D 239/02; C07D 213/02; C07C 25/24
(52) U.S. Cl. .............. 428/1.1; 252/299.62; 252/299.61; 544/334; 544/335; 546/345; 546/346; 570/183
(58) Field of Search ............... 252/299.62, 299.01; 428/1.1; 570/183

(56) References Cited

FOREIGN PATENT DOCUMENTS

| DE | A 43 03 634 | 8/1994 |
|---|---|---|
| EP | 0 546 338 | 6/1993 |
| EP | 0 725 121 | 8/1996 |
| EP | 0 768 360 | 4/1997 |
| EP | 0 711 818 | 5/2000 |
| JP | A 1-168792 | 7/1989 |
| JP | A 1-306493 | 12/1989 |
| JP | A 50344 | 11/1990 |
| JP | A 4-4290 | 1/1992 |
| JP | A 6-263663 | 12/1994 |
| JP | B 7-29990 | 4/1995 |
| WO | WO 97/04039 | 2/1997 |

OTHER PUBLICATIONS

Clark, Noel A. and Lagerwall, Sven T.; *Submicrosecond Bistable Electro–optic Switching in Liquid Crystals*, Mar. 13, 1980, pp. 899–901.
Jones, J.C., Towler, M.J., and Hughs, J.R., *Fast, High–contrast Ferroelectric Liquid Crystal Displays and the Role of Dielectric Biaxiality*, vol. 14, No. 2, (1993), pp. 86–93.
Koden, Mitsuhiro, *Ferroelectric Liquid Materials for Practical FLCD'S*, vol 179, pp. 121–129, (1996).
Surguy, P.W.H. et al, *The Joers/Alvey Ferroelectric MultiplexingSscheme*, vol. 122, pp. 63–79, (1991).
Ross, P.W. et al, *Color Digital Ferroelectric LCD's for Laptop Applications*, (1992), pp. 217–220.

*Primary Examiner*—Shean C. Wu
(74) *Attorney, Agent, or Firm*—Frommer Lawrence & Haug

(57) ABSTRACT

A ferroelectric liquid crystal mixture, especially useful for operation in the $\tau V_{min}$-mode, comprises a 5-Arylindane derivative of the formula (I),

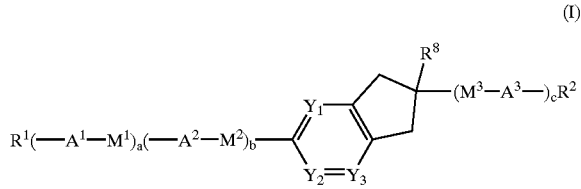

(I)

wherein
Y is CH, CF or N and
$R^1(-A^1-M^1)_a(-A^2-M^2)_b-$, $(M^3-A^3-)_cR^2$ are mesogenic groups.

12 Claims, No Drawings

5-ARYLINDANE DERIVATIVES AND FERROELECTRIC LIQUID CRYSTAL MIXTURE CONTAINING SAME

The present invention relates to novel 5-arylindane derivatives and ferroelectric liquid crystal mixtures. More particularly, it relates to a ferroelectric liquid crystal mixture, which shows a high switching speed when driven at a low voltage, and a liquid crystal display device with the use of this liquid crystal mixture.

Since Clark and Lagerwall found Surface Stabilized Ferroelectric Liquid Crystals (SSFLC) in 1980 [N. A. Clark and S. T. Lagerwall, Appl. Phys. Lett., 36, 899 (1980)], these liquid crystals have attracted attentions as display materials in the coming generation and a number of studies have been carried out thereon. The reasons therefore are as follows. (1) These ferroelectric liquid crystals have a high response speed. (2) They have memory properties which enable a display of a large information capacity and they can be produced at a relatively low cost, since no active device (thin film transistor, etc.) is needed. (3) They have a broad viewing angle. Thus, these liquid crystals are expected to be usable in a display device having a large screen size and a large display capacity.

To use a ferroelectric liquid crystal display device in practice, it is an important factor to achieve a highly defined contrast. It is very difficult to establish a highly defined contrast at the desired level by using ferroelectric liquid crystals. The reasons therefore reside in, for example, the zigzag defect in the smectic C phase, a decrease in the effective cone angle due to the chevron geometry, the insufficient memory properties, etc. There have been proposed various methods for achieving a highly defined contrast. Examples of these methods include the use of an oblique vapor-deposition film as an alignment layer, the C1 uniform method by using an alignment layer having a high pretilt, the utilization of a quasi-bookshelf geometry through an AC electric field processing or by using a naphthalene-based compound, and the use of a material having a negative dielectric anisotropy. Among the above-mentioned methods, the one with the use of a material having a negative dielectric anisotropy ($\Delta\varepsilon$) depends on a phenomenon that, when an electric field of a high frequency is applied perpendicularly to the electrode substrate, liquid crystal molecules having a negative As are aligned in parallel with the electrode substrate. This phenomenon is called the AC stabilization effect.

Multiplexed FLC devices can operate in two different ways: the so-called "normal mode" and the so-called "inverse mode", the latter also sometimes being referred to as "$\tau\ V_{min}$-mode" or "negative dielectric mode". The distinction of both modes lies in the addressing schemes and in the different requirement with respect to the dielectric tensor of the FLC material, i.e. the FLC mixture. Surveys are given, for example, in "Fast High Contrast Ferroelectric Liquid Crystal Displays and the Role of Dielectric Biaxiality" by J. C. Jones, M. J. Towler, J. R. Hughes, Displays, Volume 14, No. 2 (1993) 86–93 (referred to as Jones hereafter); M. Koden, Ferroelectrics 179, 121 (1996) and references cited therein.

In general, the switching characteristics of FLC can be discussed in terms of a diagram having the driving voltage (V) on the horizontal axis and the driving pulse width ($\tau$, time) on the vertical axis as in Jones, FIG. 4, 8, 10 or 11.

A switching curve is determined experimentally and divides the V,$\tau$ area into a switching and non-switching part. Usually, the higher the voltage, the smaller is the pulse width for switching. Such a behaviour is typically observed for the so-called "normal mode" FLC devices within the range of applied driving voltages.

For a suitable material, however, the V,$\tau$ curve reaches a minimum (at voltage $V_{min}$) as—for example—shown in Jones, FIG. 8, 10, 11 and then shows an upturn for higher voltages which is due to the superposition of dielectric and ferroelectric torques. FLC devices work in the inverse mode, if in the temperature range of operation, the sum of row and column driving voltage is higher than the voltage at the minimum of the V,$\tau$ curve, i.e. $V_{row}+V_{col}>V_{min}$.

Examples of this driving mode are given in P. W. H. Surguy et al., Ferroelectrics 1991, 122, 63 (referred to as Surguy hereafter) and P. W. Ross, Proc. SID, 1992, 217.

Surguy reported a driving system in which switching is effected under the voltage
$|V_s-V_d|$ but not under
$|V_s+V_d|$ or $|V_d|$.
($V_s$: strobe pulse; $V_d$: data pulse)

The driving voltage in this system is determined by ($\tau-V_{min}$) characteristics for the materials. According to Surguy, the value $V_{min}$ is defined as follows;

$$V_{\min} = E_{\min} * d = \frac{P_s * d}{\sqrt{3 * \varepsilon_0 * \Delta\varepsilon * \sin^2\Theta}}$$

In the above formula, $E_{min}$ stands for the minimum strength of the electric field; d stands for the cell gap, $P_s$ stands for the spontaneous polarization; $\Delta\varepsilon$ stands for the dielectric anisotropy; and $\Theta$ stands for the tilt angle of the liquid crystal material.

By taking the biaxial anisotropy ($\delta\varepsilon$) into consideration, furthermore, M. J. Towler et al. (Liquid Crystals 1992, Bd. 11) obtained the values $V_{min}$ and $\tau_{min}$ as defined below.

$$|V_{\min}| = \frac{P_s * d}{\varepsilon_0 * \sqrt{3 * (\sin^2\Theta - \delta\varepsilon)}}$$

$$\tau_{\min} \sim \frac{\eta * (\Delta\varepsilon * \sin^2\Theta - \delta\varepsilon)}{P_s^2}$$

($\eta$: viscosity)

However, the ferroelectric liquid crystal material disclosed by Ross et al. still shows only a slow response speed and $[V_s+V_d]$ exceeds 55 V, which makes it less usable in practice.

Further ferroelectric liquid crystal mixtures appropriate for driving systems with the use of the AC stabilization effect or driving systems with the use of the $\tau-V_{min}$ characteristics are disclosed, e.g. in JP A 168792/1989, 306493/1989 and 4290/1992, JP B 29990/1995 and JP A 503444/1990.

EP-B 0 546 338 discloses liquid crystal mixtures, especially ferroelectric (chiral smectic) liquid crystal mixtures containing specific indane-2,6-diyl-compounds. Apart from a 2,6-substitution the indane is not substituted.

DE-A43 03 634 discloses indane-2-yl-compounds which may be substituted in the 5- and/or 6-position by F, Cl, $CF_3$, $OCF_3$ or $OCF_2H$. The compounds may be used in liquid crystal mixtures.

JP-A-06263663 discloses 4,6-difluoro-indane-2-yl-compounds for liquid crystal mixtures.

However, since the development of ferroelectric liquid crystal mixtures can in no way be regarded as complete, the manufactures of displays are still interested in a very wide variety of mixtures. Another reason for this is that only the interaction of the liquid crystal mixtures with the individual components of the display device or of the cells (for example the alignment layer) allows conclusions to be drawn on the quality of the liquid crystal mixtures too.

The object of the present invention was therefore to provide ferroelectric liquid crystal mixtures and compounds thereof which are suitable for improving the property profile of ferroelectric liquid crystal displays, particularly of ferroelectric liquid crystal (FLC) displays operated in the inverse mode (using the ($\tau$-$V_{min}$) characteristics).

The present invention provides a ferroelectric liquid crystal mixture comprising a compound of group A:

A. 5-Arylindane derivatives of the formula (I),

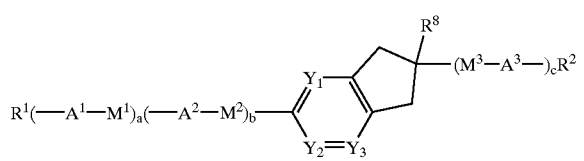

(I)

wherein the symbols and indices have the following meanings:

$R^1$ and $R^2$, independently of one another, are
(a) a hydrogen atom, —F, —Cl, —CN, —$CF_3$ or —$OCF_3$,
(b) a straight-chain or branched-chain alkyl group (with or without an asymmetric carbon atom) having from 1 to 20 carbon atoms, in which
b1) one or more non-adjacent and non-terminal —$CH_2$— groups may be replaced by —O—, —S—, —CO—, —CO—O—, —O—CO—, —O—CO—O— or —Si($CH_3$)$_2$— and/or
b2) one or more —$CH_2$— groups may be replaced by —CH=CH—, —C≡C—, 1,4-cyclohexylene, 1,4-phenylene, cyclopropane-1,2-diyl or 1,3-cyclopentylene and/or
b3) one or more hydrogen atoms of the alkyl group may be substituted by F and/or Cl and/or
b4) the terminal $CH_3$-group may be replaced by any one of the following chiral groups (optically active or racemic):

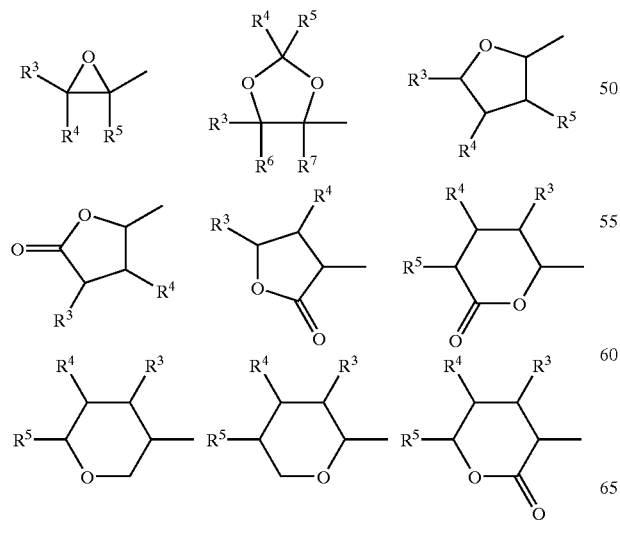

with the proviso that only one of $R^1$, $R^2$ can be a hydrogen atom, —F, —Cl, —CN, —$CF_3$ or —$OCF_3$;

$R^3$, $R^4$, $R^5$, $R^6$, $R^7$, independently of one another, are
a) a hydrogen atom,
b) a straight-chain or branched-chain alkyl group (with or without an asymmetric carbon atom) having from 1 to 16 carbon atoms, where
b1) one or more non-adjacent and non-terminal —$CH_2$— groups may be replaced by —O— and/or
b2) one or two —$CH_2$— groups may be replaced by —CH=CH— and/or
b3) one or more hydrogen atoms of the alkyl group may be substituted by F or Cl,
c) $R^4$ and $R^5$ may also together be —($CH_2$)$_4$— or —($CH_2$)$_5$— if they are bonded to an oxirane, dioxolane, tetrahydrofuran, tetrahydropyrane, butyrolactone or valerolactone system;

$R^8$ is
a) a hydrogen atom, a halogen atom or CN
b) a straight-chain or branched-chain alkyl group (with or without an asymmetric carbon atom) having from 1 to 16 carbon atoms, where
b1) one or more non-adjacent and non-terminal —$CH_2$— groups may be replaced by —O—, —S—, —CO—, —CO—O— or —O—CO— and/or
b2) one or more —$CH_2$— groups may be replaced by —CH=CH— or —C≡C— and/or
b3) one or more hydrogen atoms of the alkyl group may be substituted by F and/or Cl;

$Y^1$, $Y^2$ and $Y^3$, independently of one another, are —CF—, —N— or —CH—;

$M^1$, $M^2$, $M^3$, independently of one another, are —CO—O—, —O—CO—, —$CH_2$—O—, —O—$CH_2$—, —$CH_2$—$CH_2$—, —CH=CH—, —C≡C—, —$CH_2$—$CH_2$—CO—O—, —O—CO—$CH_2$—$CH_2$— or a single bond;

A¹, A², A³, independently of one another, are
1,4-phenylene, in which one or more H atoms may be replaced by F, Cl and/or CN, pyridine-2,5-diyl, in which one H atom may be replaced by F, pyrimidine-2,5-diyl, pyrazine-2,5-diyl, in which one H atom may be replaced by F, pyridazin-3,6-diyl, in which one H atom may be replaced by F, 1,4-cyclohexylene, in which one or two hydrogen atoms may be substituted by CN and/or F and/or CH₃, naphthalene-2,6-diyl, in which one or more H atoms may be replaced by F, Cl and/or CN, thiophene-2,5-diyl, in which one or two H atoms may be replaced by F, [1,3,4]-thiadiazole-2,5-diyl, [1,3]-thiazole-2,4-diyl, in which one H atom may be replaced by F, [1,3]-thiazole-2,5-diyl, in which one H atom may be replaced by F, or 1,3-dioxane-2,5-diyl;

a, b, c are 0 or 1 with the proviso, that compounds of the formula (I) may not contain more than four five- ore six-membered ring systems;

and a further compound of any of the groups B to G:

B. Phenanthrene derivatives of the formula (II)

(II)

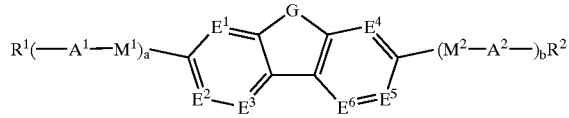

in which the symbols and indices have the following meanings:

E¹, E², E³, E⁴, E⁵ and E⁶ are —N—, —CF— or —CH—, with the following provisos:
  if E¹ (E⁴) is —N— or —CF—, E² and E³ (E⁵ and E⁶) must be —CH—;
  if E² and/or E³ (E⁵ and/or E⁶) are —CF—, E¹ (E⁴) must be —CH—;
  if E² (E⁵) is —N—, E¹ (E⁴) must be —CH—, while E³ (E⁶) can be —CH— or —CF—;
  and at least one of E¹ to E⁶ must be —N— or —CF—;

G is —CH₂CH₂— or —CH=CH—;

R¹ and R² independently of one another, are
  (a) a hydrogen atom, —F, —Cl, —CN, —CF₃ or —OCF₃,
  (b) a straight-chain or branched-chain alkyl group (with or without an asymmetric carbon atom) having from 1 to 20 carbon atoms, in which
    b1) one or more non-adjacent and non-terminal —CH₂— groups may be replaced by —O—, —S—, —CO—, —CO—O—, —O—CO—, —O—CO—O— or —Si(CH₃)₂— and/or
    b2) one or more —CH₂— groups may be replaced by —CH=CH—, —C≡C—, 1,4-cyclohexylene, 1,4-phenylene, cyclopropane-1,2-diyl or 1,3-cyclopentylene and/or
    b3) one or more hydrogen atoms of the alkyl group may be substituted by F and/or Cl and/or
    b4) the terminal CH₃-group may be replaced by any one of the following chiral groups (optically active or racemic):

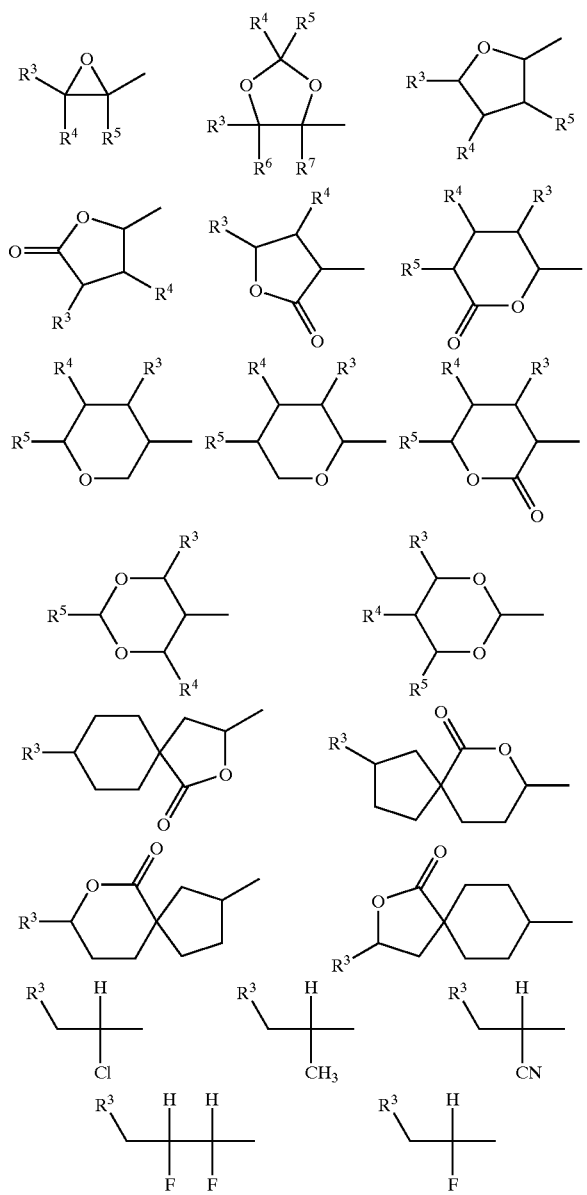

with the proviso that only one of R¹, R² can be a hydrogen atom, —F, —Cl, —ON, —CF₃ or—OCF₃;

R³, R⁴, R⁵, R⁶, R⁷, independently of one another, are
  a) a hydrogen atom,
  b) a straight-chain or branched-chain alkyl group (with or without an asymmetric carbon atom) having from 1 to 16 carbon atoms, where
    b1) one or more non-adjacent and non-terminal —CH₂— groups may be replaced by —O— and/or
    b2) one or two —CH₂— groups may be replaced by —CH=CH— and/or
    b3) one or more hydrogen atoms of the alkyl group may be substituted by F or Cl,
  c) R⁴ and R⁵ may also together be —(CH₂)₄— or —(CH₂)₅— if they are bonded to an oxirane, dioxolane, tetrahydrofuran, tetrahydropyrane, butyrolactone or valerolactone system;

M¹, M², independently of one another, are
—CO—O—, —O—CO—, —CH₂—O—, —O—CH₂—, —CH₂—CH₂—, —CH=CH—, —C≡C—, —CH$_2$—CH$_2$—CO—O—, —O—CO—CH$_2$—CH$_2$— or a single bond;

A$^1$, A$^2$, independently of one another, are
1,4-phenylene, in which one or more H atoms may be replaced by F, Cl and/or CN, pyridine-2,5-diyl, in which one H atom may be replaced by F, pyrimidine-2,5-diyl, pyrazine-2,5-diyl, in which one H atom may be replaced by F, pyridazin-3,6-diyl, in which one H atom may be replaced by F, 1,4-cyclohexylene in which one or two hydrogen atoms may be substituted by CN and/or F and/or CH$_3$, thiophene-2,5-diyl, [1,3,4]-thiadiazole-2,5-diyl, [1,3]-thiazole-2,4-diyl, [1,3]-thiazole-2,5-diyl or 1,3-dioxane-2,5-diyl;

a, b are 0 or 1 with the proviso, that compounds of the formula (II) may not contain more than three five- or six-membered ring systems;

C. 2-Fluoropyridine derivatives of the formula (III),

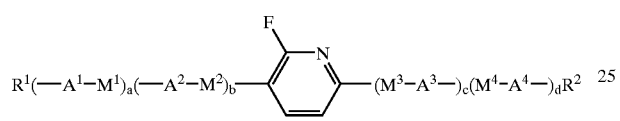

(III)

in which the symbols and indices have the following meanings:

R$^1$ and R$^2$, independently of one another, are
(a) a hydrogen atom, —F, —Cl, —CN, —CF$_3$ or —OCF$_3$,
(b) a straight-chain or branched-chain alkyl group (with or without an asymmetric carbon atom) having from 1 to 20 carbon atoms, in which
  b1) one or more non-adjacent and non-terminal —CH$_2$— groups may be replaced by —O—, —S—, —CO—, —CO—O—, —O—CO—, —O—CO—O— or —Si(CH$_3$)$_2$— and/or
  b2) one or more —CH$_2$— groups may be replaced by —CH=CH—, —C≡C—, 1,4-cyclohexylene, 1,4-phenylene, cyclopropane-1,2-diyl or 1,3-cyclopentylene and/or
  b3) one or more hydrogen atoms of the alkyl group may be substituted by F and/or Cl and/or
  b4) the terminal CH$_3$-group may be replaced by any one of the following chiral groups (optically active or racemic):

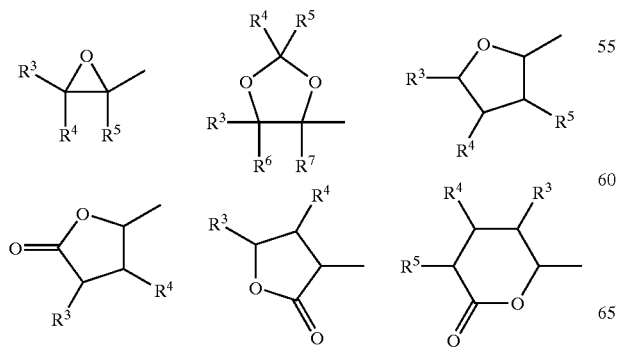

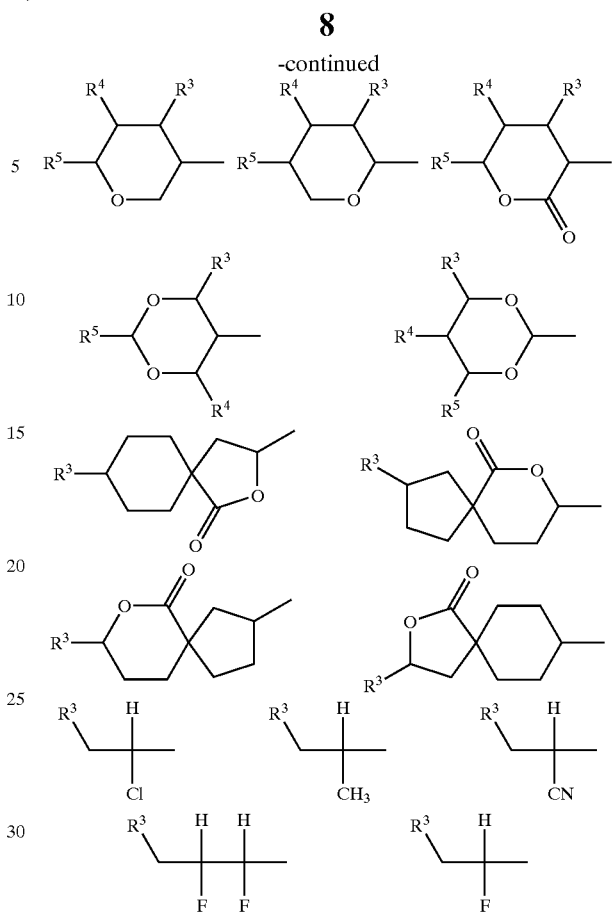

with the proviso that only one of R$^1$, R$^2$ can be a hydrogen atom, —F, —Cl, —CN, —CF$_3$ or —OCF$_3$;

R$^3$, R$^4$, R$^5$, R$^6$, R$^7$, independently of one another, are
a) a hydrogen atom,
b) a straight-chain or branched-chain alkyl group (with or without an asymmetric carbon atom) having from 1 to 16 carbon atoms, where
  b1) one or more non-adjacent and non-terminal —CH$_2$— groups may be replaced by —O— and/or
  b2) one or two —CH$_2$— groups may be replaced by —CH=CH— and/or
  b3) one or more hydrogen atoms of the alkyl group may be substituted by F or Cl,
c) R$^4$ and R$^5$ may also together be —(CH$_2$)$_4$— or —(CH$_2$)$_5$— if they are bonded to an oxirane, dioxolane, tetrahydrofuran, tetrahydropyrane, butyrolactone or valerolactone system;

M$^1$, M$^2$, M$^3$, M$^4$, independently of one another, are
—CO—O—, —O—CO—, —CH$_2$—O—, —O—CH$_2$—, —CH$_2$—CH$_2$—, —CH=CH—, —C≡C—, —CH$_2$—CH$_2$—CO—O—, —O—CO—CH$_2$—CH$_2$— or a single bond;

A$^1$, A$^2$, A$^3$, A$^4$, independently of one another, are
1,4-phenylene, in which one or more H atoms may be replaced by F, Cl and/or CN, pyridine-2,5-diyl, in which one H atom may be replaced by F, pyrimidine-2,5-diyl, pyrazine-2,5-diyl, in which one H atom may be replaced by F, pyridazin-3,6-diyl, in which one H atom may be replaced by F, 1,4-cyclohexylene in which one or two hydrogen atoms may be substituted by CN and/or F and/or CH$_3$, naphthalene-2,6-diyl in which one or more H atoms may be replaced by F, Cl and/or CN, thiophene-2,5-diyl, [1,3,4]-thiadiazole-2,5-diyl, [1,3]-thiazole-2,4-diyl, [1,3]-thiazole-2,5-diyl or 1,3-dioxane-2,5-diyl;

a, b, c, d are 0 or 1 with the proviso, that compounds of the formula (III) may not contain more than four five- ore six-membered ring systems;

D. Phenylene derivatives of the formula (IV),

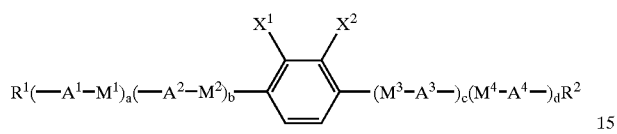

(IV)

in which the symbols and indices have the following meanings:

$R^1$ and $R^2$, independently of one another, are
(a) a hydrogen atom, —F, —Cl, —CN, —$CF_3$ or —$OCF_3$,
(b) a straight-chain or branched-chain alkyl group (with or without an asymmetric carbon atom) having from 1 to 20 carbon atoms, in which
  b1) one or more non-adjacent and non-terminal —$CH_2$— groups may be replaced by —O—, —S—, —CO—, —CO—O—, —O—CO—, —O—CO—O— or —Si($CH_3$)$_2$— and/or
  b2) one or more —$CH_2$— groups may be replaced by —CH=CH—, —C≡C—, 1,4-cyclohexylene, 1,4-phenylene, cyclopropane-1,2-diyl or 1,3-cyclopentylene and/or
  b3) one or more hydrogen atoms of the alkyl group may be substituted by F and/or Cl and/or
  b4) the terminal $CH_3$-group may be replaced by any one of the following chiral groups (optically active or racemic):

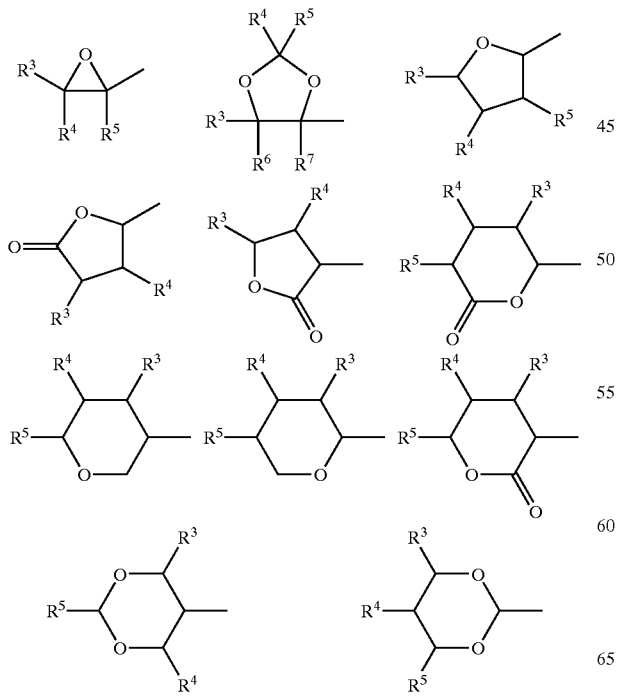

-continued

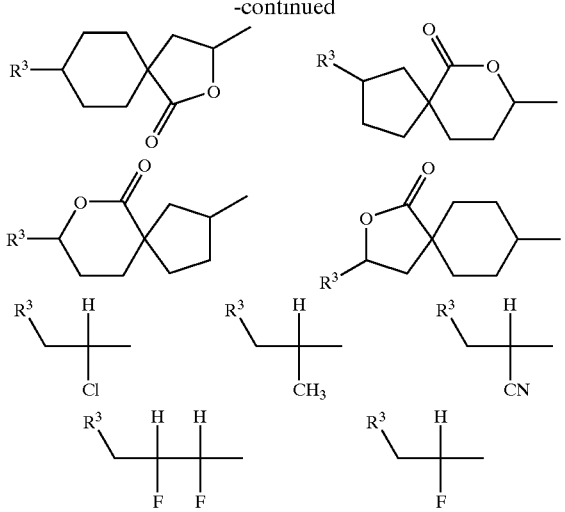

with the proviso that only one of $R^1$, $R^2$ can be a hydrogen atom, —F, —Cl, —CN, —$CF_3$ or —$OCF_3$;

$R^3$, $R^4$, $R^5$, $R^6$, $R^7$; independently of one another, are
a) a hydrogen atom,
b) a straight-chain or branched-chain alkyl group (with or without an asymmetric carbon atom) having from 1 to 16 carbon atoms, where
  b1) one or more non-adjacent and non-terminal —$CH_2$— groups may be replaced by —O— and/or
  b2) one or two —$CH_2$— groups may be replaced by —CH=CH— and/or
  b3) one or more hydrogen atoms of the alkyl group may be substituted by F or Cl,
c) $R^4$ and $R^5$ may also together be —($CH_2$)$_4$— or —($CH_2$)$_5$— if they are bonded to an oxirane, dioxolane, tetrahydrofuran, tetrahydropyrane, butyrolactone or valerolactone system;

$X^1$ and $X^2$, independently of one another, are hydrogen, F, Cl, $CF_3$ or CN, with the proviso that $X^1$ and $X^2$ are not simultaneously hydrogen;

$M^1$, $M^2$, $M^3$, $M^4$, independently of one another, are —CO—O—, —O—CO—, —$CH_2$—O—, —O—$CH_2$—, —$CH_2$—$CH_2$—, —CH=CH—, —C≡C—, —$CH_2$—$CH_2$—CO—O—, —O—CO—$CH_2$—$CH_2$— or a single bond;

$A^1$, $A^2$, $A^3$, $A^4$, independently of one another, are 1,4-phenylene, in which one or more H atoms may be replaced by F, Cl and/or CN, pine-2,5-diyl, in which one H atom may be replaced by F, pyrimidine-2,5-diyl, pyrazine-2,5-diyl, in which one H atom may be replaced by F, pyridazin-3,6-diyl, in which one H atom may be replaced by F, 1,4-cyclohexylene in which one or two hydrogen atoms may be substituted by CN and/or F and/or $CH_3$, naphthalene-2,6-diyl in which one or more H atoms may be replaced by F, Cl and/or CN, 1,2,3,4-tetrahydronapthalene-2,6-diyl, thiophene-2,5-diyl, [1,3,4]-thiadiazole-2,5-diyl, [1,3]-thiazole-2,4-diyl, [1,3]-thiazole-2,5-diyl or 1,3-dioxane-2,5-diyl;

a, b, c, d are 0 or 1 with the proviso, that compounds of the formula (IV) may not contain more than four five- ore six-membered ring systems;

E. Meta-substituted aromatic compounds of the formula (V):

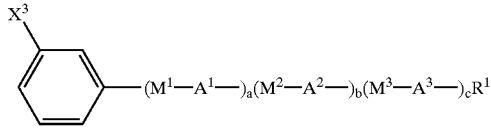

(V)

wherein the symbols and indices have the following meanings:

$X^3$ is
(a) —F, —Cl, —Br, —CN, —$CF_3$ or —$OCF_3$,
(b) a straight-chain or branched-chain alkyl group (with or without an asymmetric carbon atom) having from 1 to 12 carbon atoms, in which
  b1) one or two non-adjacent and non-terminal —$CH_2$— groups may be replaced by —O—, —S—, —CO—, —CO—O— or —O—CO— and/or
  b2) one or more hydrogen atoms of the alkyl group may be substituted by F and/or Cl and/or CN;

$R^1$ is
(a) a hydrogen atom, —F, —Cl, —CN, —$CF_3$ or —$OCF_3$,
(b) a straight-chain or branched-chain alkyl group (with or without an asymmetric carbon atoms) having from 1 to 20 carbon atoms, in which
  b1) one or more non-adjacent and non-terminal —$CH_2$— groups may be replaced by —O—, —S—, —CO—, —CO—O—, —O—CO—, —O—CO—O— or —Si($CH_3$)$_2$— and/or
  b2) one or more —$CH_2$— groups may be replaced by —CH=CH—, —C≡C—, 1,4-cyclohexylene, 1,4-phenylene, cyclopropane-1,2-diyl or 1,3-cyclopentylene and/or
  b3) one or more hydrogen atoms of the alkyl group may be substituted by F and/or Cl and/or
  b4) the terminal $CH_3$-group may be replaced by any one of the following chiral groups (optically active or racemic):

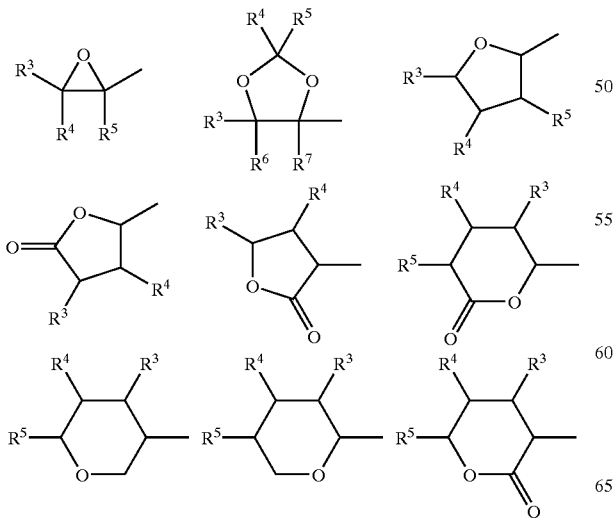

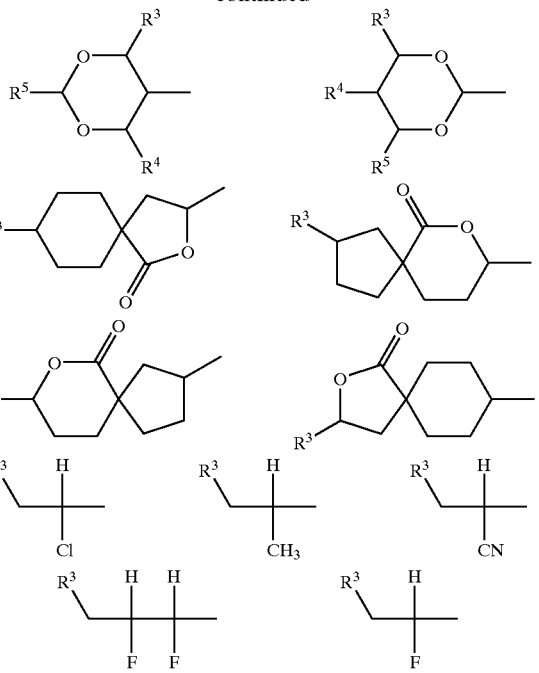

with the proviso that $R^1$ can not be a hydrogen atom, —F, —Cl, —CN, —$CF_3$ or —$OCF_3$ if $X^3$ is —F, —Cl, —Br, —CN, —$CF_3$ or —$OCF_3$;

$R^3$, $R^4$, $R^5$, $R^6$, $R^7$, independently of one another, are
a) a hydrogen atom,
b) a straight-chain or branched-chain alkyl group (with or without an asymmetric carbon atom) having from 1 to 16 carbon atoms, where
  b1) one or more non-adjacent and non-terminal —$CH_2$— groups may be replaced by —O— and/or
  b2) one or two —$CH_2$— groups may be replaced by —CH=CH— and/or
  b3) one or more hydrogen atoms of the alkyl group may be substituted by F or Cl,
c) $R^4$ and $R^5$ may also together be —($CH_2$)$_4$— or —($CH_2$)$_5$— if they are bonded to an oxirane, dioxolane, tetrahydrofuran, tetrahydropyrane, butyrolactone or valerolactone system;

$M^1$, $M^2$, $M^3$, independently of one another, are, —CO—O—, —O—CO—, —$CH_2$—O—, —O—$CH_2$—, —$CH_2$—$CH_2$—, —CH=CH—, —C≡C—, —$CH_2$—$CH_2$—CO—O—, —O—CO—$CH_2$—$CH_2$— or a single bond;

$A^1$, $A^2$, $A^3$, independently of one another, are 1,4-phenylene, in which one or more H atoms may be replaced by F, Cl and/or CN, pyridine-2,5-diyl, in which one H atom may be replaced by F, pyrimidine-2,5-diyl, pyrazine-2,5-diyl, in which one H atom may be replaced by F, pyridazin-3,6-diyl, in which one H atom may be replaced by F, 1,4-cyclohexylene in which one or two hydrogen atoms may be substituted by CN and/or F and/or $CH_3$, naphthalene-2,6-diyl in which one or more H atoms may be replaced by F, Cl and/or CN, thiophene-2,5-diyl, [1,3,4]-thiadiazole-2,5-diyl, [1,3]-thiazole-2,4-diyl, [1,3]-thiazole-2,5-diyl or 1,3-dioxane-2,5-diyl;

a, b, c are 0 or 1 with the proviso, that compounds of the formula (V) may not contain more than four five- ore six-membered ring systems;

F. (1,3,4)-Thiadiazoles of the formula (VI):

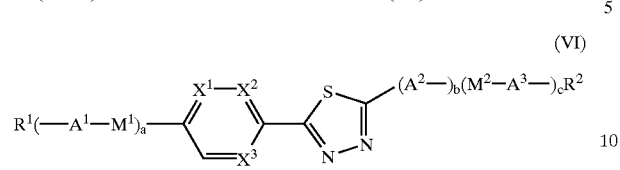

(VI)

wherein the symbols and indices have the following meanings:

$R^1$ and $R^2$, independently of one another, are
(a) a hydrogen atom, —F, —Cl, —CN, —CF$_3$ or—OCF$_3$,
(b) a straight-chain or branched-chain alkyl group (with or without an asymmetric carbon atom) having from 1 to 20 carbon atoms, in which
b1) one or more non-adjacent and non-terminal —CH$_2$— groups may be replaced by —O—, —S—, —CO—, —CO—O—, —O—CO—, —O—CO—O— or —Si(CH$_3$)$_2$— and/or
b2) one or more —CH$_2$-groups may be replaced by —CH=CH—, —C≡C—, 1,4-cyclohexylene, 1,4-phenylene, cyclopropane-1,2-diyl or 1,3-cyclopentylene and/or
b3) one or more hydrogen atoms of the alkyl group may be substituted by F and/or Cl and/or
b4) the terminal CH$_3$— group may be replaced by any one of the following chiral groups (optically active or racemic):

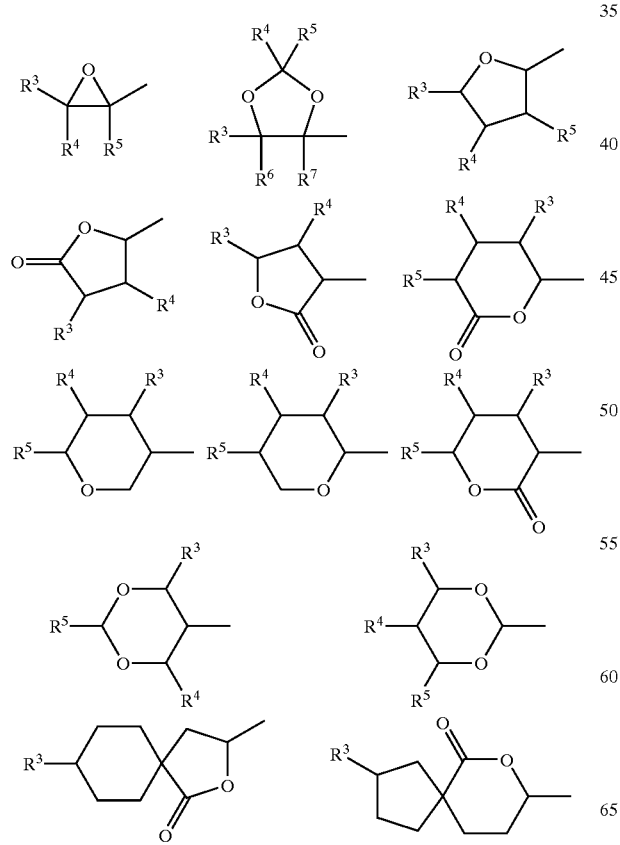

with the proviso that only one of $R^1$, $R^2$ can be a hydrogen atom, —F, —Cl, —CN, —CF$_3$ or —OCF$_3$;

$R^3$, $R^4$, $R^5$, $R^6$, $R^7$, independently of one another, are
a) a hydrogen atom,
b) a straight-chain or branched-chain alkyl group (with or without an asymmetric carbon atom) having from 1 to 16 carbon atoms, where
b1) one or more non-adjacent and non-terminal —CH$_2$— groups may be replaced by —O— and/or
b2) one or two —CH$_2$— groups may be replaced by —CH=CH— and/or
b3) one or more hydrogen atoms of the alkyl group may be substituted by F or Cl,
c) $R^4$ and $R^5$ may also together be —(CH$_2$)$_4$— or —(CH$_2$)$_5$— if they are bonded to an oxirane, dioxolane, tetrahydrofuran, tetrahydropyrane, butyrolactone or valerolactone system;

$X^1$, $X^2$, $X^3$, independently of one another, are —CF—, —N— or —CH—;

$M^1$, $M^2$, independently of one another, are —CO—O—, —O—CO—, —CH$_2$—O—, —O—CH$_2$—, —CH$_2$—CH$_2$—, —CH=CH—, —C≡C—, —CH$_2$—CH$_2$—CO—O—, —O—CO—CH$_2$—CH$_2$— or a single bond;

$A^1$, $A^3$ independently of one another, are
1,4-phenylene, in which one or more H atoms may be replaced by F, Cl and/or ON, pyridine-2,5-diyl, in which one H atom may be replaced by F, pyrimidine-2,5-diyl, pyrazine-2,5-diyl, in which one H atom may be replaced by F, pyridazin-3,6-diyl, in which one H atom may be replaced by F, 1,4-cyclohexylene in which one or two hydrogen atoms may be substituted by CN and/or F and/or CH$_3$, naphthalene-2,6-diyl in which one or more H atoms may be replaced by F, Cl and/or CN, thiophene-2,5-diyl, [1,3,4]-thiadiazole-2,5-diyl, [1,3]-thiazole-2,4-diyl, [1,3]-thiazole-2,5-diyl or 1,3-dioxane-2,5-diyl;

a, b, c are 0 or 1 with the proviso, that compounds of the formula (VI) may not contain more than four five- ore six-membered ring systems;

G. 4-Cyanocyclohexyls of the formula (VII):

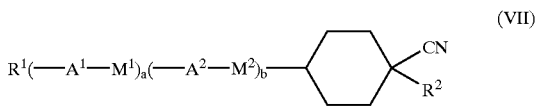

(VII)

wherein the symbols and indices have the following meanings:

R¹ is
  (a) a hydrogen atom, —F, —Cl, —CN, —CF₃ or —OCF₃,
  (b) a straight-chain or branched-chain alkyl group (with or without an asymmetric carbon atom) having from 1 to 20 carbon atoms, in which
    b1) one or more non-adjacent and non-terminal —CH₂— groups may be replaced by —O—, —S—, —CO—, —CO—O—, —O—CO—, —O—CO—O— or —Si(CH₃)₂— and/or
    b2) one or more —CH₂— groups may be replaced by —CH=CH—, —C≡C—, 1,4-cyclohexylene, 1,4-phenylene, cyclopropane-1,2-diyl or 1,3-cyclopentylene and/or
    b3) one or more hydrogen atoms of the alkyl group may be substituted by F and/or Cl and/or
    b4) the terminal CH₃-group may be replaced by any one of the following chiral groups (optically active or racemic):

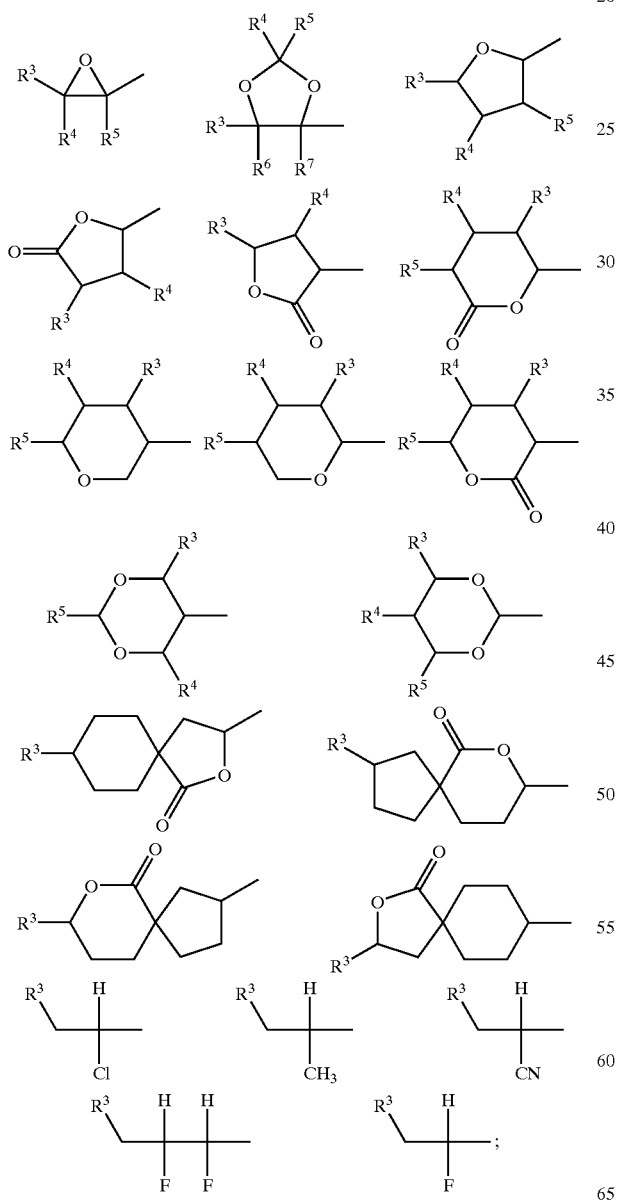

R² is
  (a) a straight-chain or branched-chain alkyl group (with or without an asymmetric carbon atom), having from 1 to 16 carbon atoms, in which
    a1) one or two non-adjacent and non-terminal —CH₂— groups may be replaced by —O—, —S—, —CO—, —CO—O—, —O—CO— or —Si(CH₃)₂— and/or
    a2) one or two —CH₂— groups may be replaced by —CH=CH—, —C≡C— and/or
    a3) one or more hydrogen atoms of the alkyl group may be substituted by F and/or Cl and/or CN and/or CF₃;
R³, R⁴, R⁵, R⁶, R⁷, independently of one another, are
  a) a hydrogen atom,
  b) a straight-chain or branched-chain alkyl group (with or without an asymmetric carbon atom) having from 1 to 16 carbon atoms, where
    b1) one or more non-adjacent and non-terminal —CH₂— groups may be replaced by —O— and/or
    b2) one or two —CH₂— groups may be replaced by —CH=CH— and/or
    b3) one or more hydrogen atoms of the alkyl group may be substituted by F or Cl,
  c) R⁴ and R⁵ may also together be —(CH₂)₄— or —(CH₂)₅— if they are bonded to an oxirane, dioxolane, tetrahydrofuran, tetrahydropyrane, butyrolactone or valerolactone system;
M¹, M², independently of one another, are
  —CO—O—, —O—CO—, —CH₂—O—, —O—CH₂—, —CH₂—CH₂—, —CH=CH—, —C≡C—, —CH₂—CH₂—CO—O—, —O—CO—CH₂—CH₂— or a single bond;
A¹, A², independently of one another, are
  1,4-phenylene, in which one or more H atoms may be replaced by F, Cl and/or CN, pyridine-2,5-diyl, in which one H atom may be replaced by F, pyrimidine-2,5-diyl, pyrazine-2,5-diyl, in which one H atom may be replaced by F, pyridazin-3,6-diyl, in which one H atom may be replaced by F, 1,4-cyclohexylene in which one or two hydrogen atoms may be substituted by CN and/or F and/or CH₃, naphthalene-2,6-diyl in which one or more H atoms may be replaced by F, Cl and/or CN, thiophene-2,5-diyl, [1,3,4]-thiadiazole-2,5-diyl, [1,3]-thiazole-2,4-diyl, [1,3]-thiazole-2,5-diyl or 1,3-dioxane-2,5-diyl;
a, b are 0 or 1 with the proviso, that compounds of the formula (VII) may not contain more than four five- ore six-membered ring systems.

A further object of the invention is to provide a ferroelectric liquid crystal display device, especially one operated in the τV$_{min}$ mode, using the above described mixture.

Yet a further object of the invention is the use of the above described mixture in a ferroelectric liquid crystal display, especially one operated in the τV$_{min}$ mode.

Mixtures according to the invention are distinguished, inter alia, by a large absolute value of the dielectric anisotropy, a low viscosity, low melting point and supercooling. They are capable of achieving a high response speed and a low voltage driving.

Preferred are those compounds of group A, in which the symbols and indices in the formula (I) have the following meanings:
  R¹ and R², independently of one another, are
    (a) a hydrogen atom,
    (b) a straight-chain or branched-chain alkyl group (with or without an asymmetric carbon atom) having from 1 to 16 carbon atoms, in which b1) one or two non-adjacent and non-terminal —CH$_2$— groups may be replaced by —O—, —CO—O—, —O—CO— or —Si(CH$_3$)$_2$— and/or b2) one —CH$_2$— group may be replaced by trans-1,4-cyclohexylene, 1,4-phenylene or cyclopropane-1,2-diyl and/or b3) one or more hydrogen atoms of the alkyl group may be substituted by F and/or b4) the terminal CH$_3$-group may be replaced by any one of the following chiral groups (optically active or racemic):

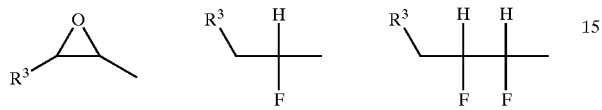

with the proviso that only one of R$^1$, R$^2$ can be a hydrogen atom;

R$^3$, R$^4$, R$^5$, R$^7$, independently of one another, are
a) a hydrogen atom,
b) a straight-chain or branched-chain alkyl group (with or without an asymmetric carbon atom) having from 1 to 12 carbon atoms, where
b1) one non-terminal —CH$_2$— group may be replaced by —O—,
c) R$^4$ and R$^5$ may also together be —(CH$_2$)$_4$— or —(CH$_2$)$_5$— if they are bonded to an oxirane, dioxolane, tetrahydrofuran, tetrahydropyrane, butyrolactone or valerolactone system;

R$^8$ is
a) a hydrogen atom
b) a straight-chain or branched-chain alkyl group (with or without an asymmetric carbon atom) having from 1 to 12 carbon atoms, where
b1) one or two non-adjacent and non-terminal —CH$_2$— groups may be replaced by —O— and/or
b2) one or more hydrogen atoms of the alkyl group may be substituted by F;

Y$^1$, Y$^2$ and Y$^3$, independently of one another, are —CF— or —CH—; M$^1$, M$^2$, M$^3$, independently of one another, are
—CO—O—, —O—CO—, —CH$_2$—O—, —O—CH$_2$— or a single bond;

A$^1$, A$^2$, A$^3$, independently of one another, are
1,4-phenylene, in which one or two H atoms may be replaced by F, pyridine-2,5-diyl, in which one H atom may be replaced by F, pyrimidine-2,5-diyl, pyrazine-2,5-diyl, trans-1,4-cyclohexylene, thiophene-2,5-diyl, in which one or two H atoms may be replaced by F, [1,3,4]-thiadiazole-2,5-diyl, or [1,3]-thiazole-2,5-diyl, in which one H atom may be replaced by F.

Examples of particularly preferred compounds of the formula (I) include:

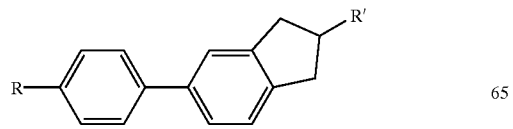

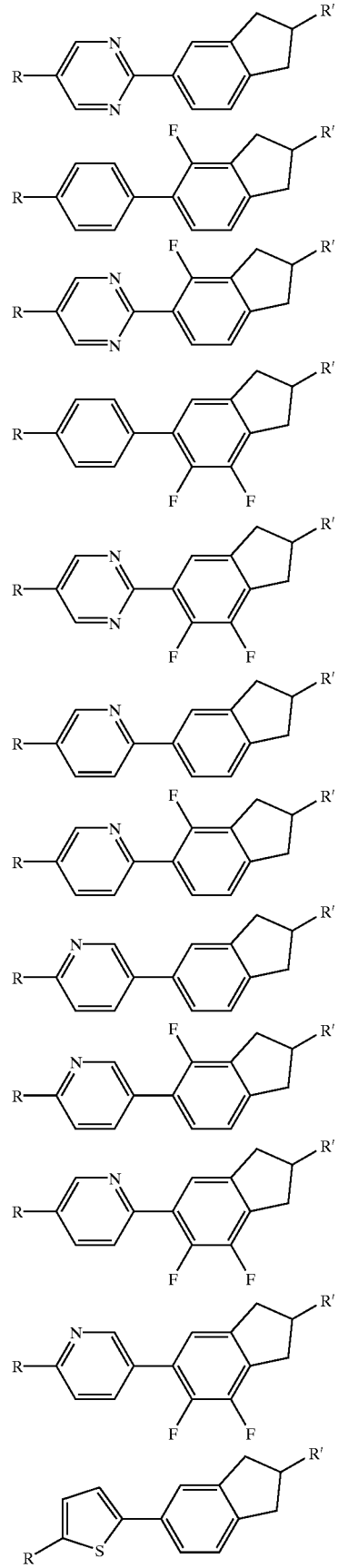

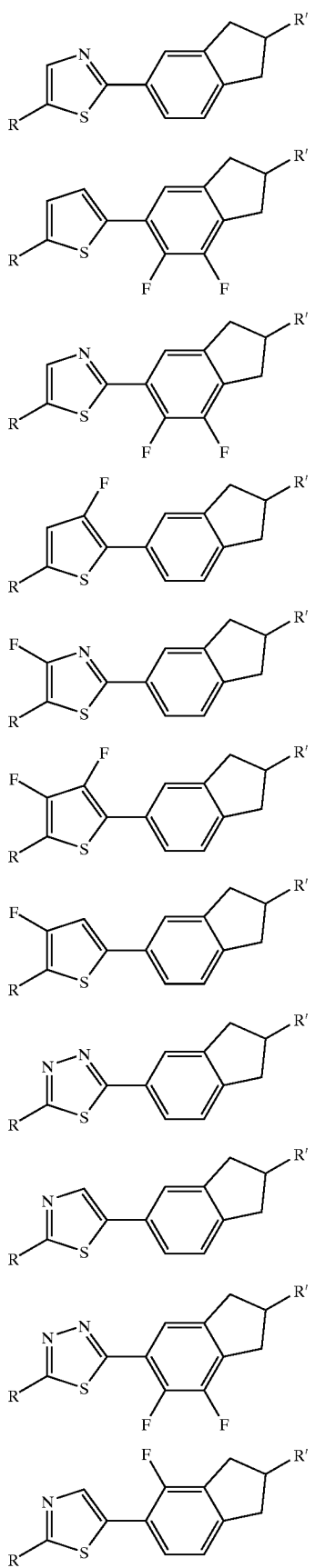
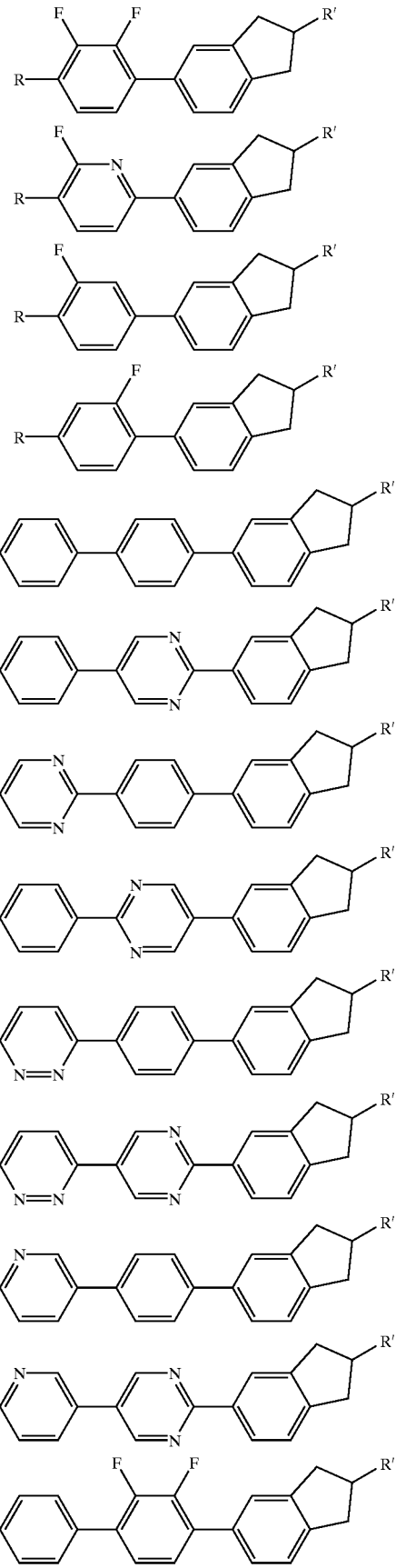

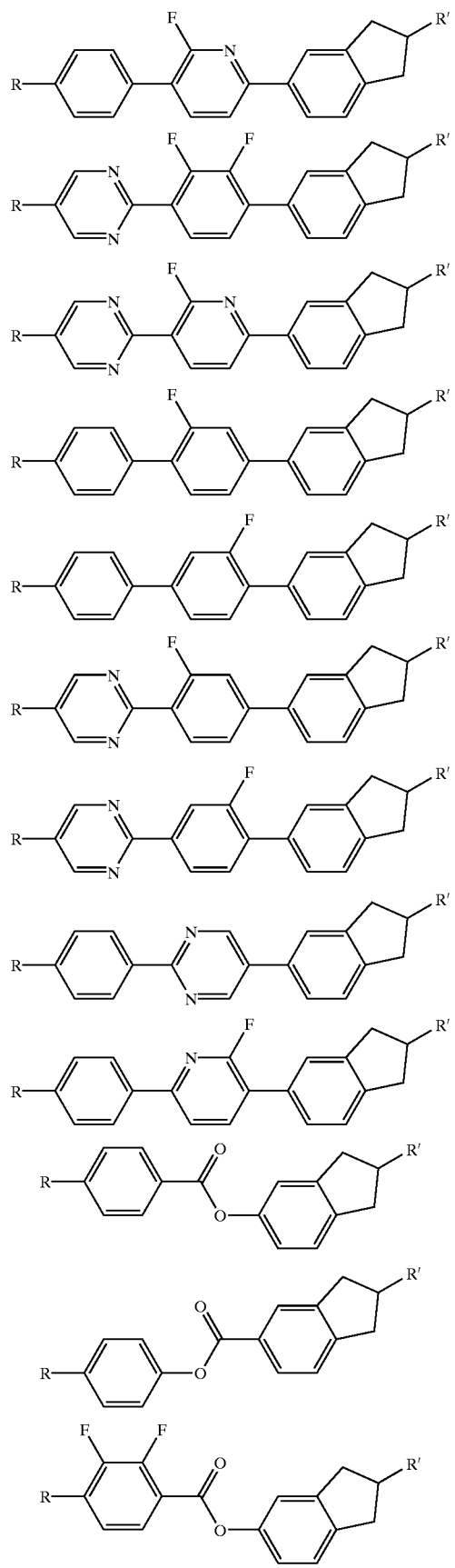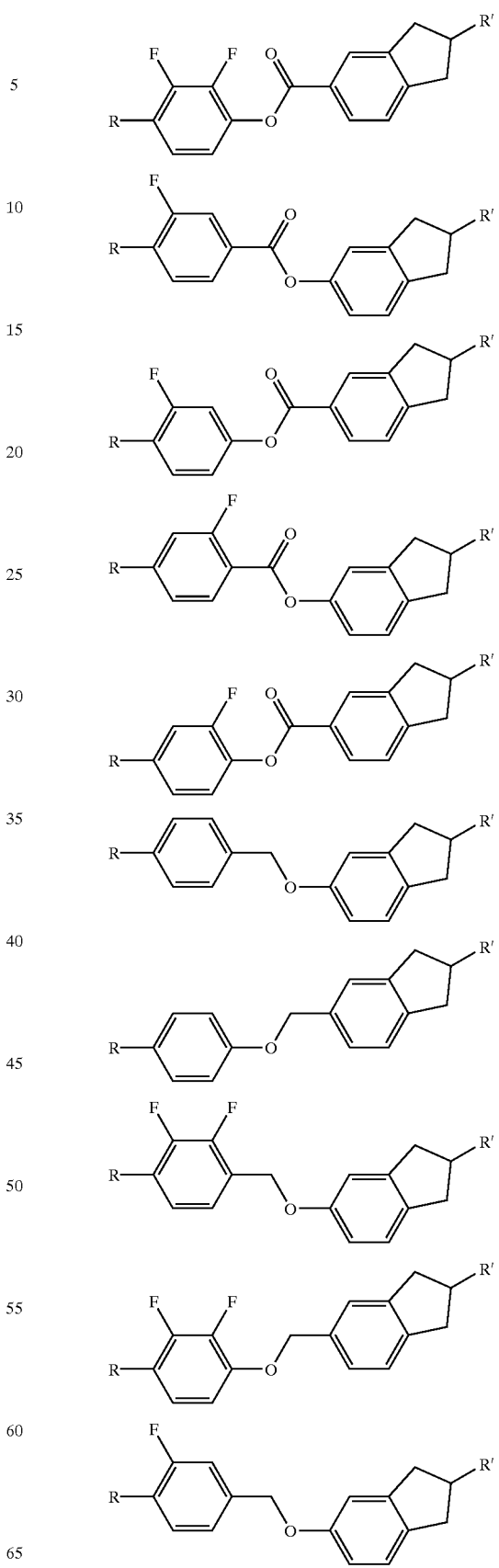

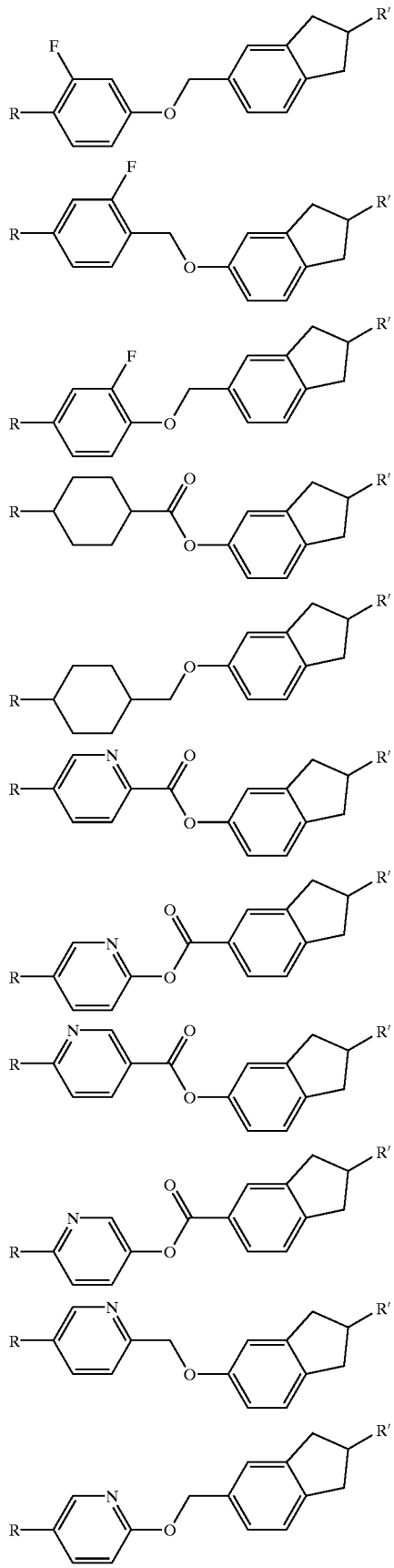

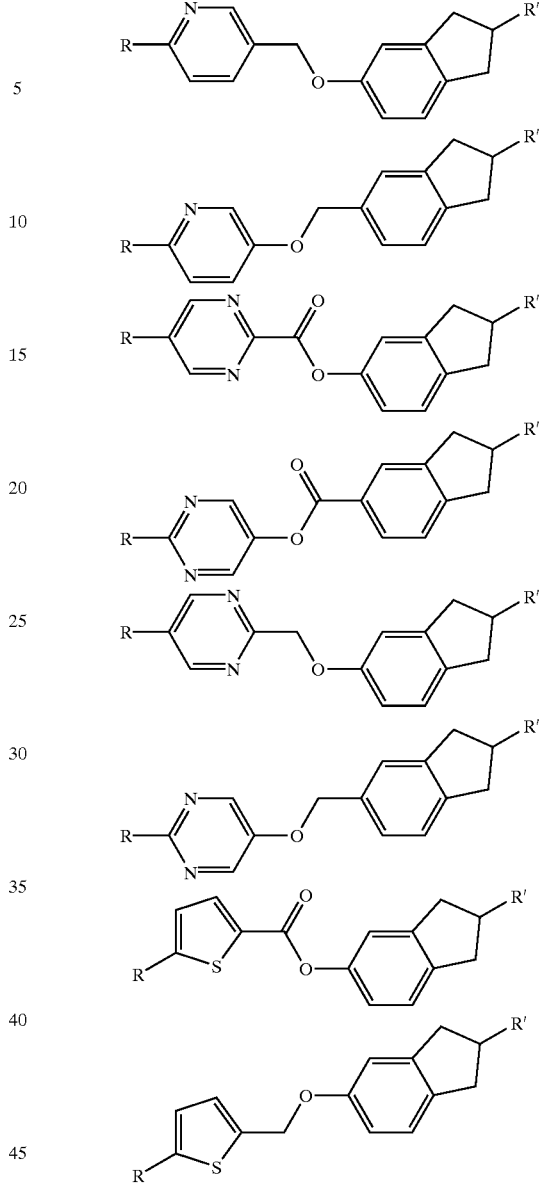

wherein R and R' have the same meanings as $R^1$ and $R^2$ in formula (I).

Further particular preference is given to the compounds of the formula (I) in which $R^1$ and $R^2$ are a straight-chain or branched-chain alkyl group having from 1 to 14 carbon atoms (with or without asymmetric carbon atoms), in which one or two —CH$_2$— groups may also be replaced by —O—, cyclopropane-1,2-diyl or —Si(CH$_3$)$_2$—, with the proviso that oxygen atoms must not be bonded directly to one another; one or more hydrogen atoms of the alkyl group may be substituted by F; $R^1$ or $R^2$ can also be hydrogen, but not both simultaneously.

Very particularly preferred are the following compounds of the formula (I):

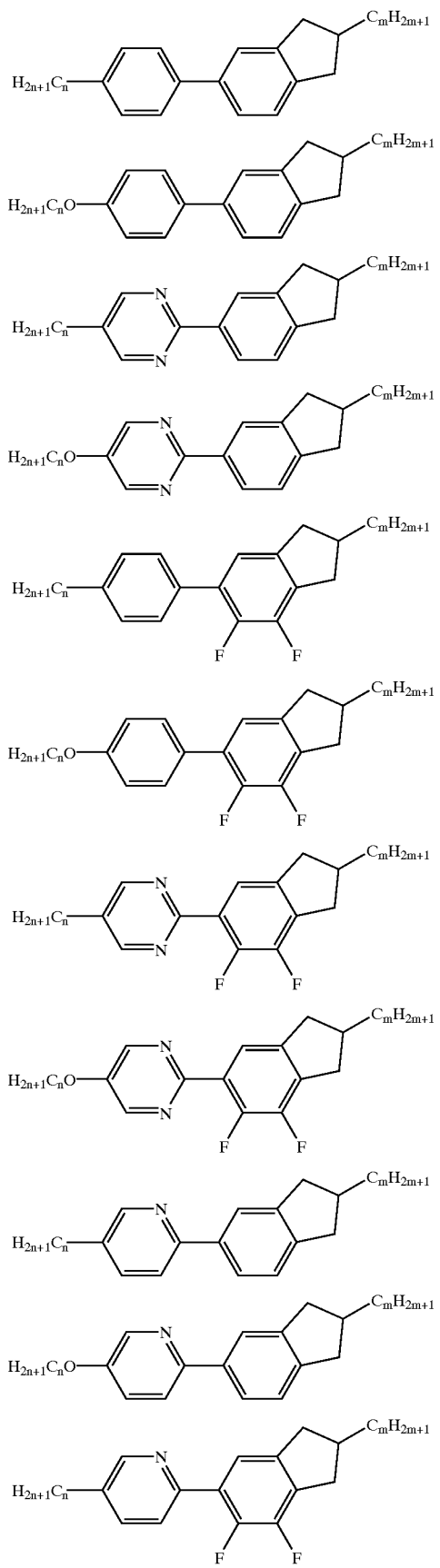
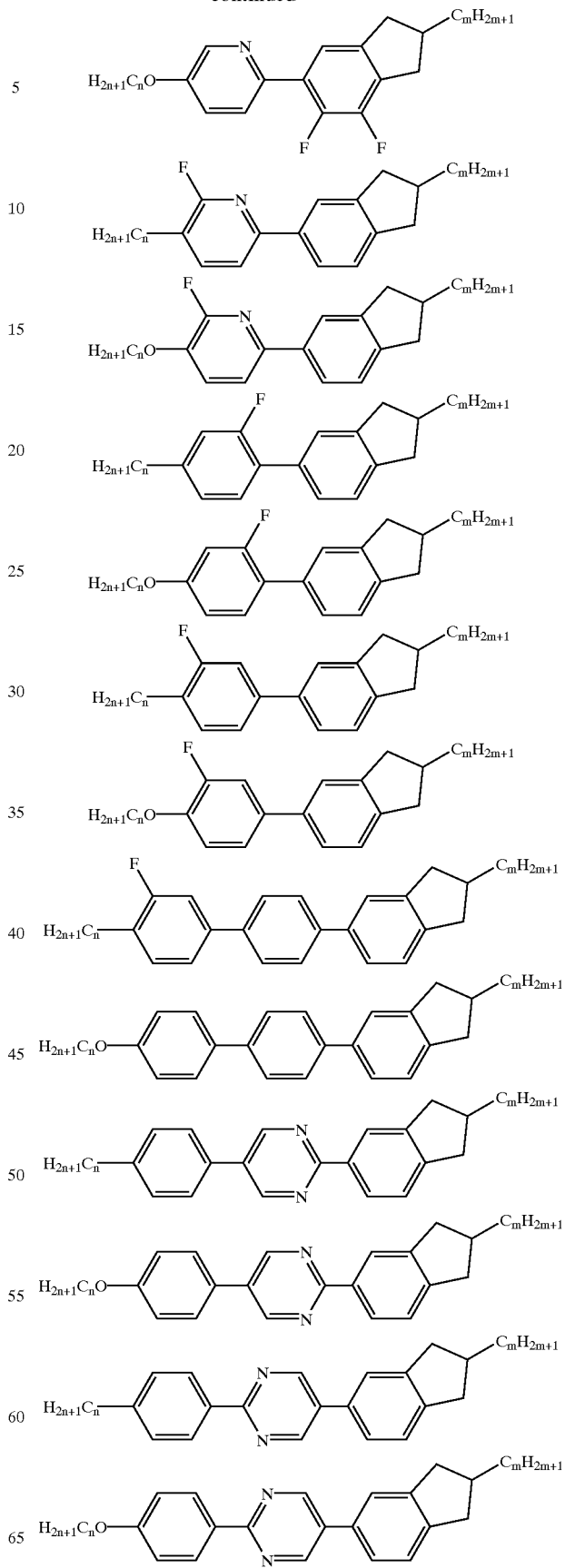

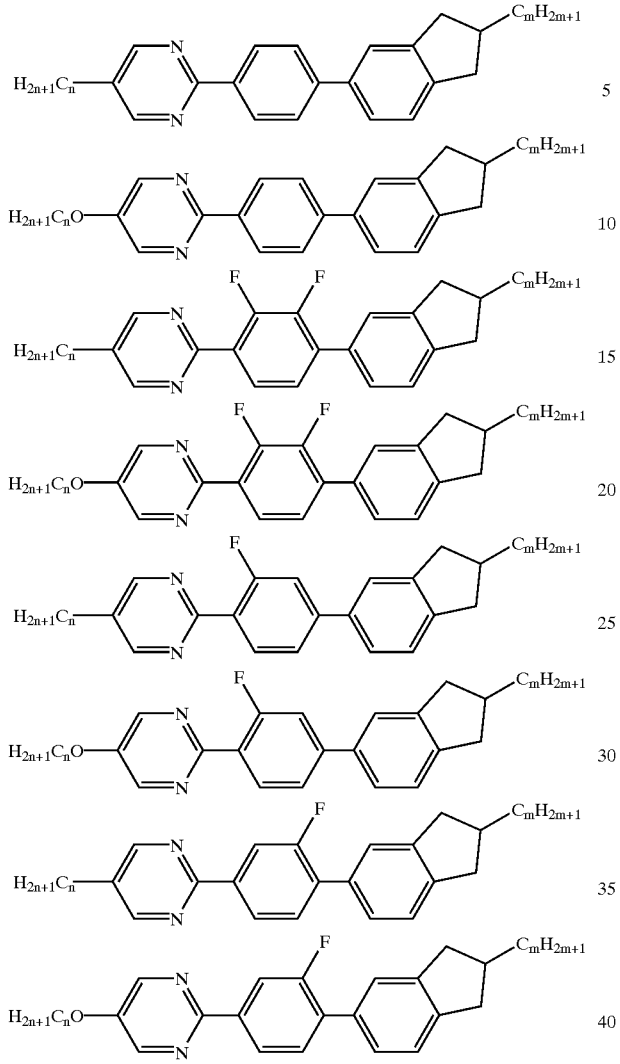

wherein n and m, independently from one another, are 0 to 16 with the proviso that 3<n+m<29.

The invention also relates to the compounds of the formula (I) and the above preferred compounds. Further preferred compounds of the formula I are those with the following residnes:

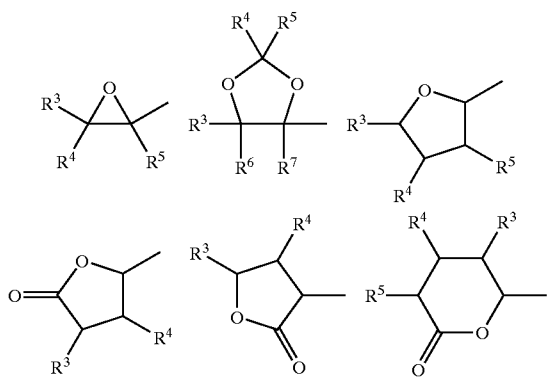

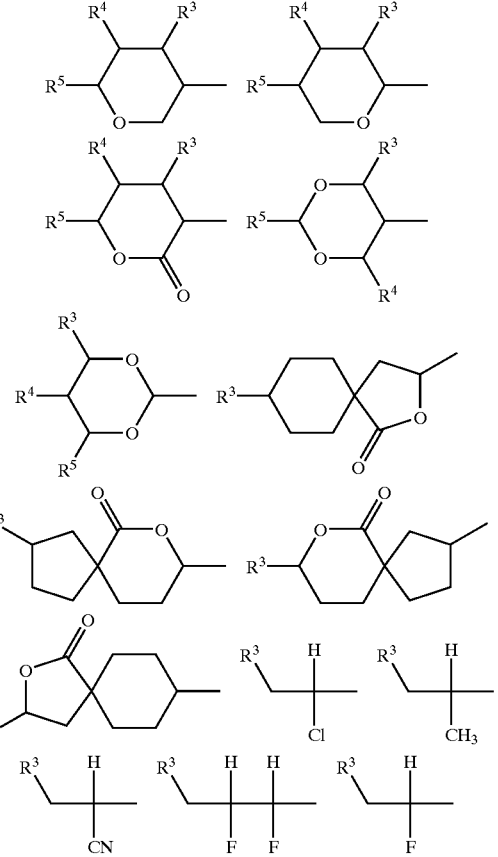

$R^1$: Hydrogen or a straight-chain or branched-chain alkyl group (with or without an asymmetric carbon atom) having from 1 to 20 carbon atoms, in which one or more non-adjacent and non-terminal $CH_2$-groups may be replaced by —O—, —CO—O—, —O—CO—, —OC(=O)O— or —Si(CH$_3$)$_2$— and one or more hydrogen atoms may be substituted by F, and $R^1$ can be hydrogen only if a is not zero;

$R^2$: Hydrogen or a straight-chain or branched-chain alkyl group (with or without an asymmetric carbon atom) having from 1 to 20 carbon atoms, in which one non-terminal $CH_2$-group may be replaced by —O— and one or more hydrogen atoms may be substituted by F, and $R^2$ can be hydrogen only if d is not zero, $M^1$: —CO—O—, —O—CO—, —CH$_2$—O—, —O—CH$_2$—, —CH$_2$CH$_2$—, —C≡C— or a single bond $M^2$: —CH$_2$CH$_2$— or a single bond $A^1$: 1,4-phenylene, in which one or two H atoms may be replaced by F, pyridine-2,5-diyl, in which on H atom may be replaced by F, pyrimidine-2,5-diyl, wherein one H atom may be replaced by F, 1,4-cyclohexylene, 4-(4-$R^1$)-cyclohexyl)phenylene, 4-biphenyl-4'-yl, in which one or two H-atoms may be replaced by F, or 4-(1-$R^1$-silycyclohexane-4-yl)phenylene $A^2$: 1,4-cyclohexylene or 1,4-phenylene, in which one or two H-atoms may be replaced by F X: H or F a, b: zero or 1, wherein the sum (a+b) is at least 1.

Preferably the symbols and indices of the formula (IA) have one or more of the following meanings:

$R^1$, $R^2$ are the same or different
  a) a straight-chain or branched-chain alkyl group (with or without an asymmetric carbon atom) having from 1 to 18 carbon atoms; where
  b) one non-terminal $CH_2$-group may be replaced by —O—
  c) one or more H-atoms may be replaced by F;

$M^1$ is —$CH_2CH_2$—, —C≡C— or a single bond;

$A^1$ is -1,4 phenylene, in which 1 or two H-atoms may be replaced by F, pyridine-2,5-diyl, wherein one H-atom may be replaced by F, or pyrimidine-2,5-diyl;

$A^2$ is 1,4-cyclohexylene;

X is H;

a is one and b is zero.

Specifically preferred compounds of the formula (IA) are selected from the group consisting of the compounds corresponding to the formulae (Ia) to (In).

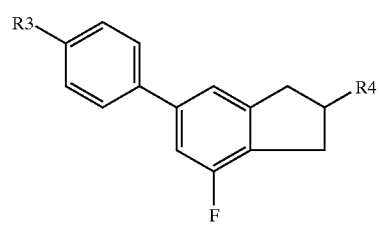
(Ia)

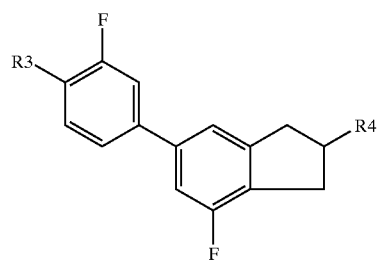
(Ib)

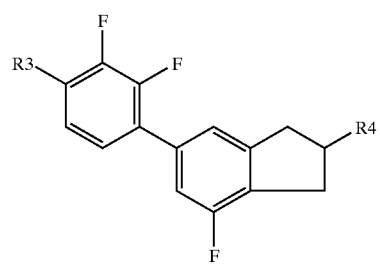
(Ic)

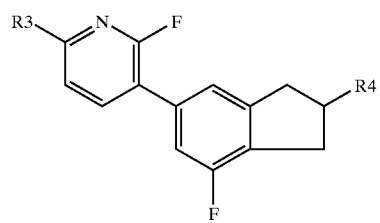
(Id)

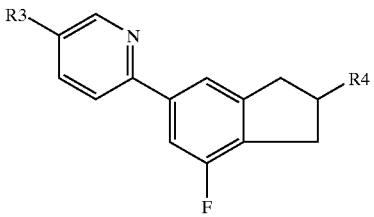
(Ie)

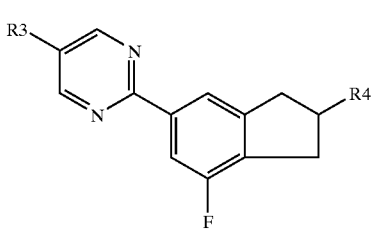
(If)

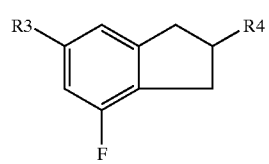
(Ig)

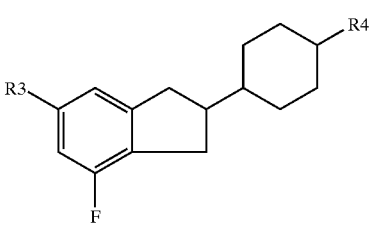
(Ih)

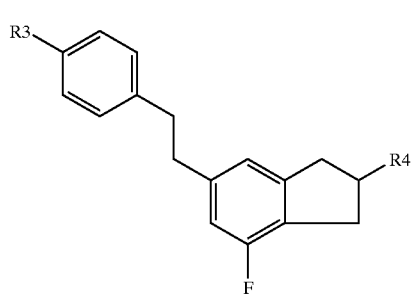
(Ii)

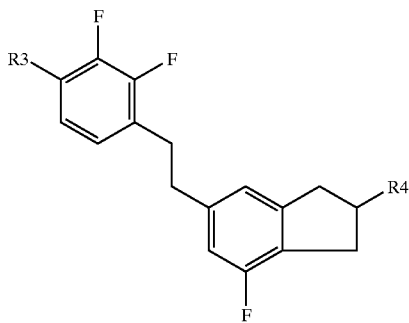
(Ik)

-continued

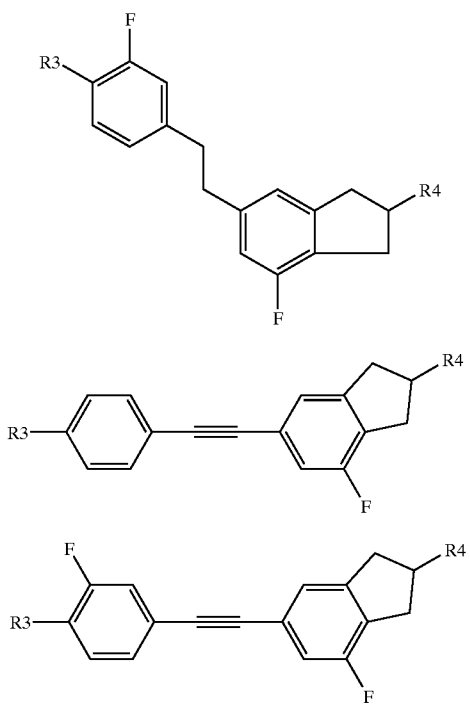

wherein
  $R^3$ is a straight-chain or branched-chain alkyl or alkyloxy-group having from 1 to 12 carbon atoms, and
  $R^4$ is a straight-chain or branched-chain alkyl group having from 1 to 12 carbon atoms.

Especially preferred are the followings meanings for the indices:
  $R^1$, $R^2$ are straight-chain alkyl groups having from 1 to 18 carbon atoms.
  $M^1$, $M^2$ are single bonds.
  $A^1$ is pyrimidine-2,5-diyl.
  a is one and
  b is zero.

Of the above compounds, the compounds (Ig), (Ih), (Ii), (Ik), (Il), (Im) and (In) are specifically useful in nematic liquid crystalline mixtures, especially nematic crystalline mixtures for active matrix displays.

$R^3$, $R^4$ are preferably alkyl groups having from 1 to 6 carbon atoms.

The compounds of the formula (IA) can advantageously be used in liquid crystalline mixtures since they have an advantageous influence on the melting point and/or the dielectric anisotropy even at low levels of admixture. They show no disadvantageous effects on other parameters of the liquid crystalline mixture (e.g. spontaneous polarization, switching time and clearance point).

Especially the compounds of the formula (IA) enrich the variety of liquid crystalline compounds which can be employed in liquid crystalline mixtures. The compounds may be the basic materials of which the liquid crystalline phases are mainly composed. The compounds of the formula (IA) can be admixed to crystalline basic materials of other structures as well, e.g. in order to improve the dielectric and/or optical anisotropy of the mixture or to optimize the viscosity of the threshold voltage. The compounds of the formula (IA) can be used e.g. for ECB-displays, for electroclinic displays and ferroelectric displays as well as ferroelectric active matrix displays. The compounds of the formula (IA) are especially useful in FLC-mixtures which are operated in the inverse mode.

Preferred are those compounds of group B, in which the symbols and indices in the formula (II) have the following meanings:
  $E^1$, $E^2$, $E^3$, $E^4$, $E^5$ and $E^6$ are —N—, —CF— or —CH—, with the following provisos:
    if $E^1$ and/or $E^4$ are —N— or —CF—, $E^2$, $E^3$, $E^5$ and $E^6$ must be —CH—;
    if $E^2$ and/or $E^3$ and/or $E^5$ and/or $E^6$ are —CF—, $E^1$ and $E^4$ must be —CH—;
    if $E^2$ and/or $E^5$ are —N—, $E^1$ and $E^4$ must be —CH—, while $E^3$ and/or $E^6$ can be —CH— or —CF—;
    and at least one of $E^1$ to $E^6$ must be —N— or —CF—;
  $R^1$ and $R^2$, independently of one another, are
    (a) a hydrogen atom,
    (b) a straight-chain or branched-chain alkyl group (with or without an asymmetric carbon atom) having from 1 to 16 carbon atoms, in which
      b1) one or two non-adjacent and non-terminal —CH$_2$— groups may be replaced by —O—, —CO, —O—CO— or —Si(CH$_3$)$_2$— and/or
      b2) one —CH$_2$— group may be replaced by trans-1,4-cyclohexylene, 1,4-phenylene or cyclopropane-1,2-diyl and/or
      b3) one or more hydrogen atoms of the alkyl group may be substituted by F and/or
      b4) the terminal CH$_3$-group may be replaced by any one of the following chiral groups (optically active or racemic):

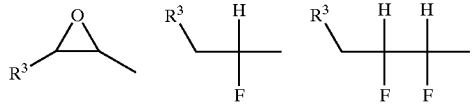

with the proviso that only one of $R^1$, $R^2$ can be a hydrogen atom;
  $R^3$, $R^4$, $R^5$, $R^6$, $R^7$, independently of one another, are
    a) a hydrogen atom,
    b) a straight-chain or branched-chain alkyl group (with or without an asymmetric carbon atom) having from 1 to 12 carbon atoms, where
      b1) one non-terminal —CH$_2$— group may be replaced by —O—,
    c) $R^4$ and $R^5$ may also together be —(CH$_2$)$_4$— or —(CH$_2$)$_5$— if they are bonded to an oxirane, dioxolane, tetrahydrofuran, tetrahydropyrane, butyrolactone or valerolactone system;
  $M^1$, $M^2$, independently of one another, are
    —CO—O—, —O—CO—, —CH$_2$—O—, —O—CH$_2$— or a single bond;
  $A^1$, $A^2$, independently of one another, are
    1,4-phenylene, in which one or two H atoms may be replaced by F, pyridine-2,5-diyl, in which one H atom may be replaced by F, pyrimidine-2,5-diyl, trans-1,4-cyclohexylene, thiophene-2,5-diyl, [1,3,4]-thiadiazole-2,5-diyl or [1,3]-thiazole-2,5-diyl.

Particular preference is given to the compounds of the formula (IIa) in which $E^1$ and/or $E^4$ are —CF—:

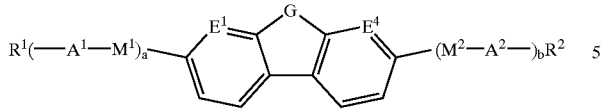
(IIa)

wherein R and R' have the same meanings as $R^1$ and $R^2$ in formula (II), and of these, very particular preference is given to the following compounds:

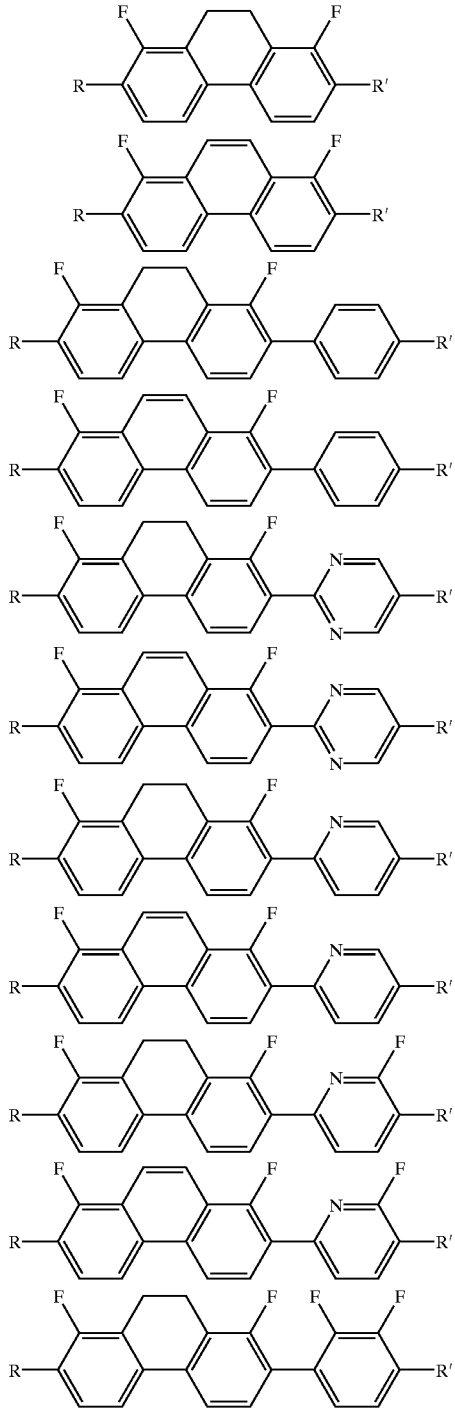

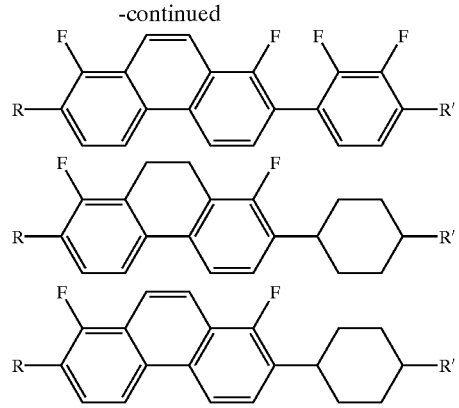

wherein R and R' have the same meanings as $R^1$ and $R^2$ in formula (II).

Further very particular preference is given to the compounds of the formula (IIa) in which $R^1$ and $R^2$ are a straight-chain or branched-chain alkyl group having from 1 to 16 carbon atoms (with or without asymmetric carbon atoms), in which one or two $CH_2$-groups may be replaced by —O—, cyclopropane-1,2-diyl or —Si(CH$_3$)$_2$—, with the proviso that oxygen atoms must not be bonded directly to one another; one or more hydrogen atoms of the alkyl group may be substituted by F; $R^1$ or $R^2$ can also be hydrogen, but not both simultaneously.

Particular preference is furthermore given to compounds of the formula (IIb) in which $E^2$, $E^3$, $E^5$ and $E^6$, independently of one another, are —CH— or —CF—, and at least one of those is —CF—:

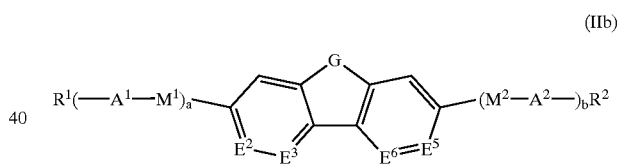
(IIb)

wherein $R^1$ and $R^2$ have the same meanings as in formula (II), and of these, very particular preference is given to the following compounds:

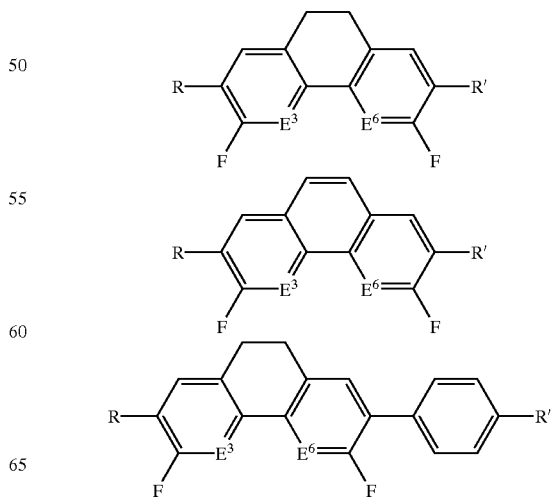

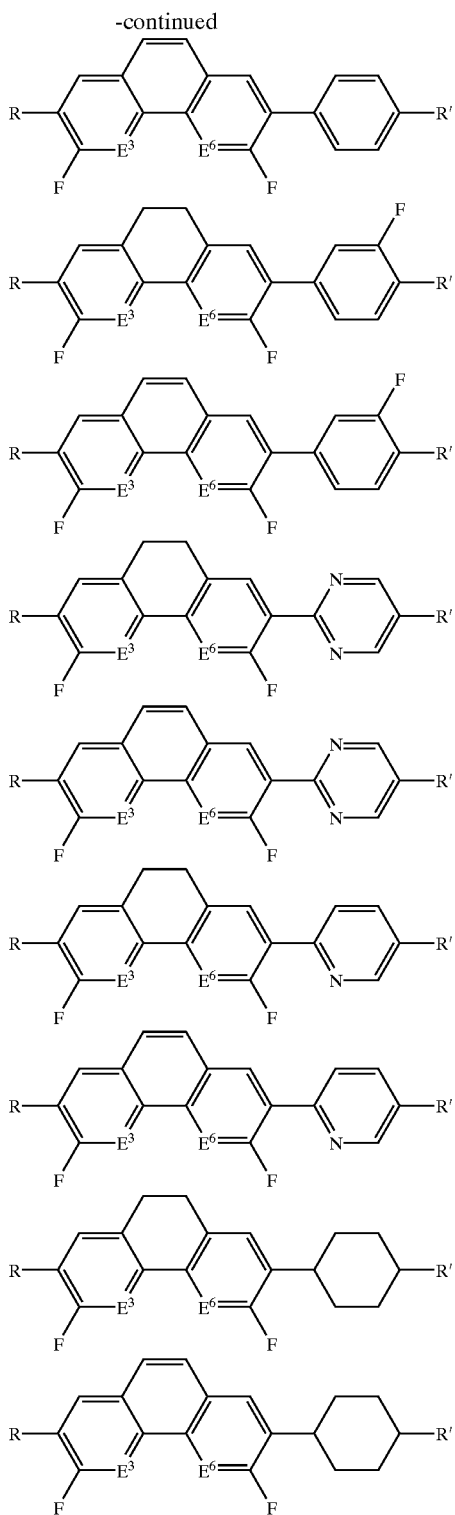

wherein R and R' have the same meanings as $R^1$ and $R^2$ in formula (II).

Further very particular preference is given to the compounds of the formula (IIb) in which $R^1$ and $R^2$ are a straight-chain or branched-chain alkyl group having from 1 to 16 carbon atoms (with or without an asymmetric carbon atom), in which one or two —$CH_2$— groups may also be replaced by —O—, cyclopropane-1,2-diyl or —Si($CH_3$)$_2$—, with the proviso that oxygen atoms must not be bonded directly to one another; one or more hydrogen atoms of the alkyl group may be substituted by F; $R^1$ or $R^2$ can also be hydrogen, but not both simultaneously.

Preferred compounds of component C., i.e. 2-fluoropyridine derivatives of the formula (III), are those in which the symbols and indices have the following meanings:

$R^1$ and $R^2$, independently of one another, are
(a) a hydrogen atom,
(b) a straight-chain or branched-chain alkyl group (with or without an asymmetric carbon atom) having from 1 to 16 carbon atoms, in which
b1) one or two non-adjacent and non-terminal —$CH_2$— groups may be replaced by —O—, —CO—O—, —O—CO— or —Si($CH_3$)$_2$— and/or
b2) one or more hydrogen atoms of the alkyl group may be substituted by F and/or
b3) the terminal $CH_3$-group may be replaced by any one of the following chiral groups (optically active or racemic):

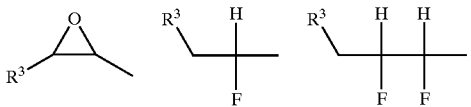

with the proviso that only one of $R^1$, $R^2$ can be a hydrogen atom;
$R^3$, $R^4$, $R^5$, $R^6$, $R^7$, independently of one another, are
a) a hydrogen atom,
b) a straight-chain or branched-chain alkyl group (with or without an asymmetric carbon atom) having from 1 to 12 carbon atoms, where
b1) one non-terminal —$CH_2$— group may be replaced by —O—,
c) $R^4$ and $R^5$ may also together be —($CH_2$)$_4$— or —($CH_2$)$_5$— if they are bonded to an oxirane, dioxolane, tetrahydrofuran, tetrahydropyrane, butyrolactone or valerolactone system;
$M^1$, $M^2$, $M^3$, $M^4$, independently of one another, are
—CO—O—, —O—CO—, —$CH_2$—O—, —O—$CH_2$— or a single bond;
$A^1$, $A^2$, $A^3$, $A^4$, independently of one another, are
1,4-phenylene, in which one or two H atoms may be replaced by F, pyridine-2,5-diyl, in which one H atom may be replaced by F, pyrimidine-2,5-diyl, trans-1,4-cyclohexylene, naphtalene-2,6-diyl, thiophene-2,5-diyl or [1,3]-thiazole-2,5-diyl.

Particularly preferred compounds of the formula (III) include:

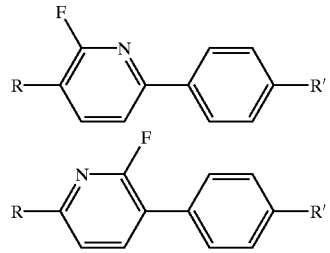

-continued
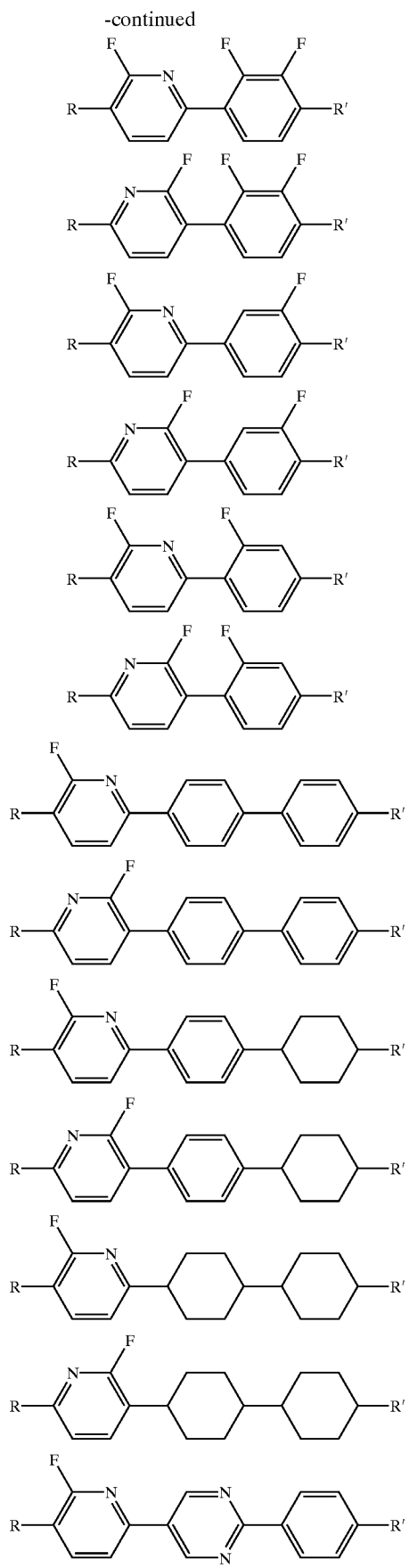
-continued
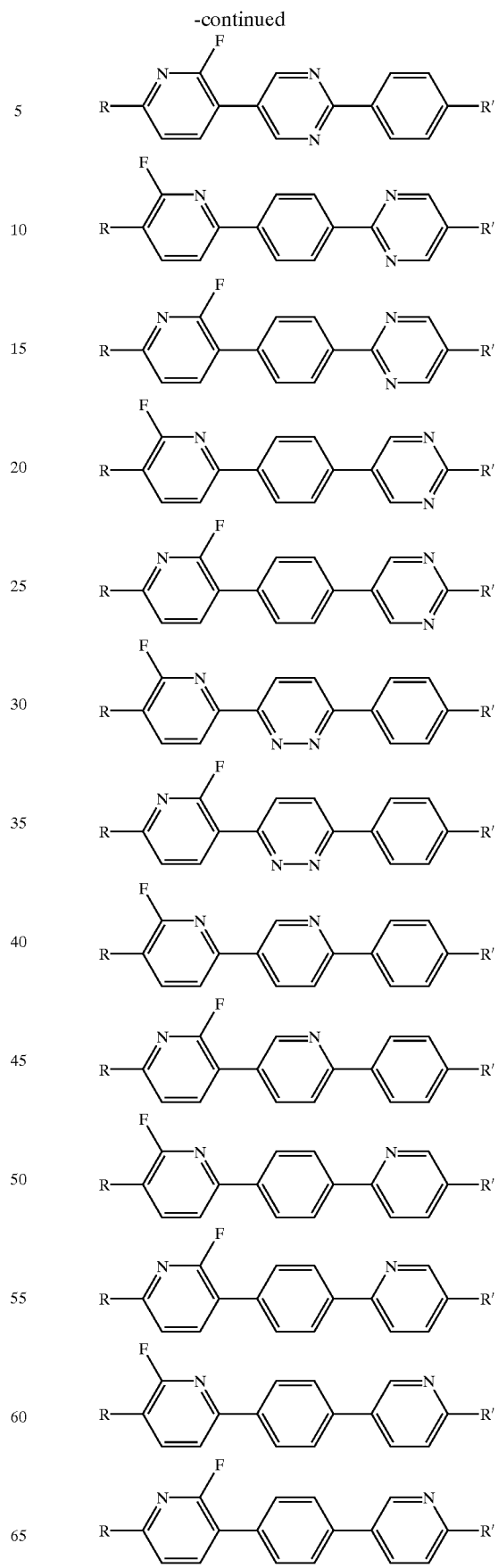

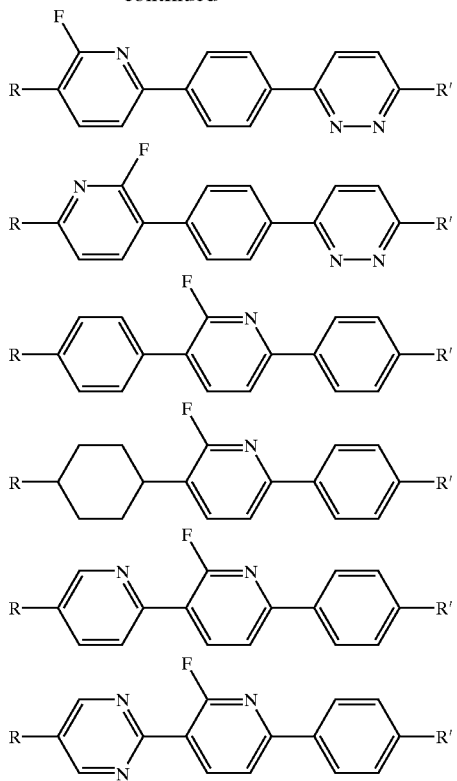

wherein R and R' have the same meanings as $R^1$ and $R^2$ in formula (III).

Further particular preference is given to the compounds of the formula (III) in which $R^1$ and $R^2$ are a straight-chain or branched-chain alkyl group having from 1 to 16 carbon atoms (with or without an asymmetric carbon atom), in which one or two —CH$_2$— groups may also be replaced by —O—, cyclopropane-1,2-diyl or —Si(CH$_3$)$_2$—, with the proviso that oxygen atoms must not be bonded directly to one another; one or more hydrogen atoms of the alkyl group may be substituted by F; $R^1$ or $R^2$ can also be hydrogen, but not both simultaneously.

Very particular preference is given to the following compounds of the formula (III):

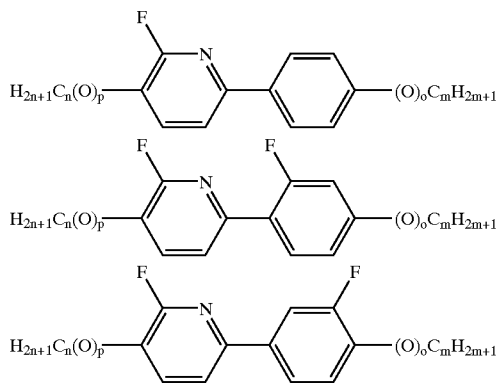

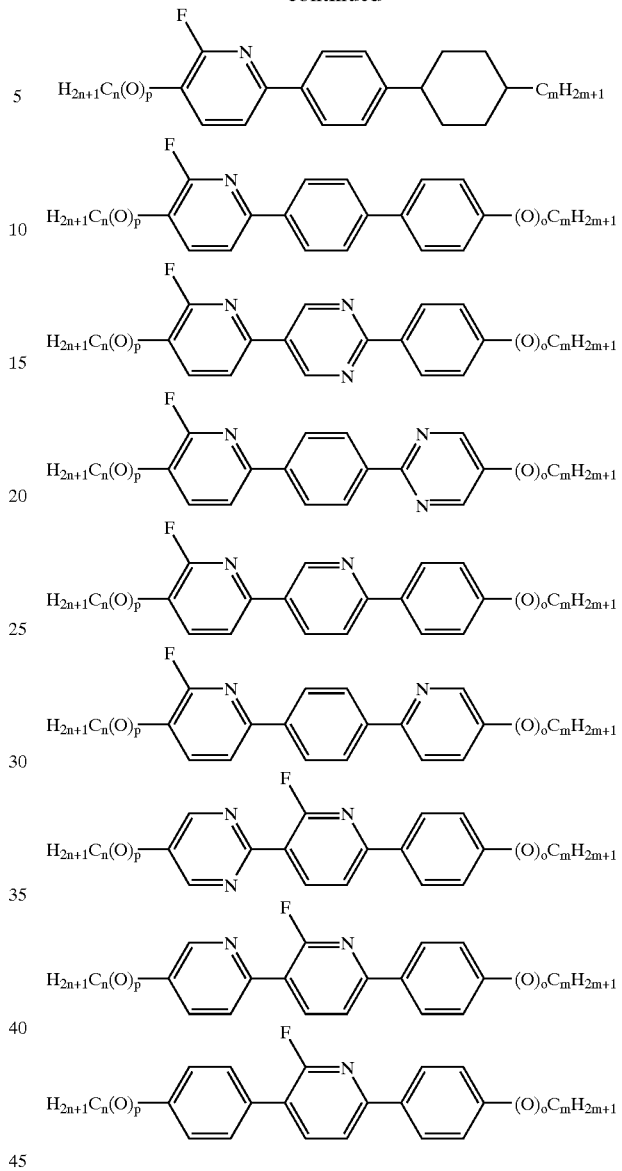

wherein n and m, independently from one another, are 0 to 16 (with the proviso that 3<n+m<29) and o and p, independently from one another, are 0 or 1.

Preferred compounds of group D, i.e., of formula (IV), are those in which the symbols and indices in formula (IV) have the following meanings:

$R^1$ and $R^2$, independently of one another, are
(a) a hydrogen atom,
(b) a straight-chain or branched-chain alkyl group (with or without an asymmetric carbon atom) having from 1 to 16 carbon atoms, in which
  b1) one or two non-adjacent and non-terminal —CH$_2$— groups may be replaced by —O—, —CO—O—, —O—CO— or —Si(CH$_3$)$_2$— and/or
  b2) one or more hydrogen atoms of the alkyl group may be substituted by F and/or
  b3) the terminal CH$_3$-group may be replaced by any one of the following chiral groups (optically active or racemic):

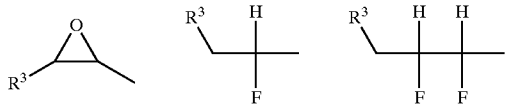

with the proviso that only one of $R^1$, $R^2$ can be a hydrogen atom;

$R^3$, $R^4$, $R^5$, $R^6$, $R^7$, independently of one another, are
  a) a hydrogen atom,
  b) a straight-chain or branched-chain alkyl group (with or without an asymmetric carbon atom) having from 1 to 12 carbon atoms, where
    b1) one non-terminal —$CH_2$—group may be replaced by —O—,
  c) $R^4$ and $R^5$ may also together be —(CH2)4— or —$(CH_2)_5$— if they are bonded to an oxirane, dioxolane, tetrahydrofuran, tetrahydropyrane, butyrolactone or valerolactone system;

$X^1$ and $X^2$, independently of one another, are selected from hydrogen, CN and F, with the proviso that $X^1$ and $X^2$ are not simultaneously hydrogen; preferably $X^1$ and/or $X^2$ are F;

$M^1$, $M^2$, $M^3$, $M^4$, independently of one another, are —CO—O—, —O—CO—, —$CH_2$—O—, —O—$CH_2$— or a single bond;

$A^1$, $A^2$, $A^3$, $A^4$, independently of one another, are 1,4-phenylene, in which one or two H atoms may be replaced by F, pyridine-2,5-diyl, in which one H atom may be replaced by F, pyrimidine-2,5-diyl, trans-1,4-cyclohexylene or naphtalene-2,6-diyl.

Examples of particularly preferred compounds of the formula (IV) include:

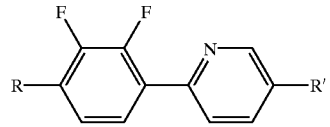

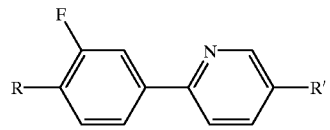

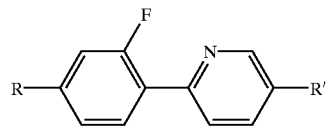

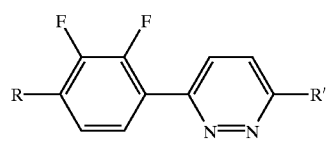

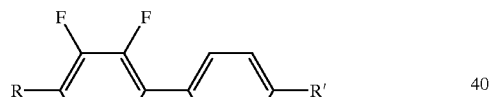

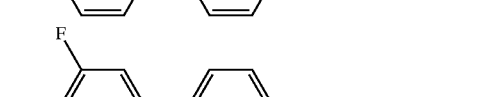

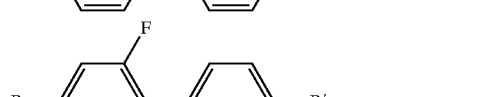

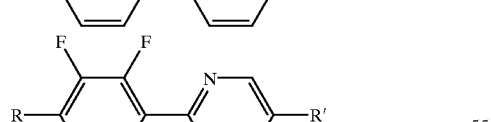

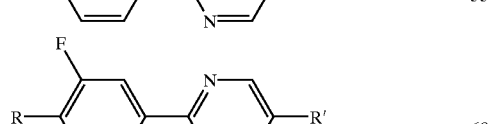

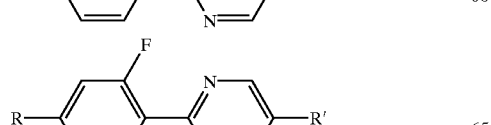

-continued

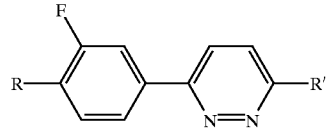

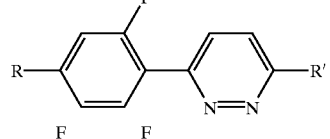

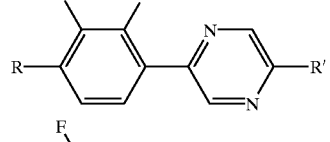

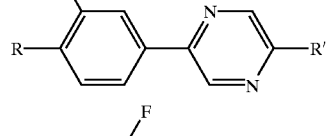

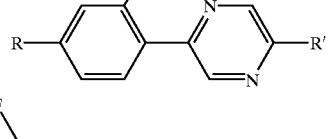

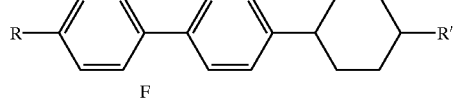

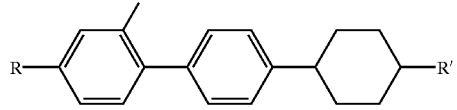

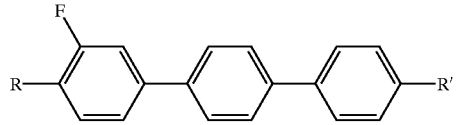

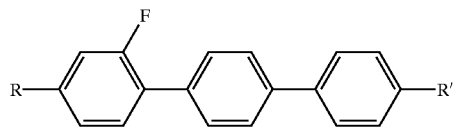

-continued

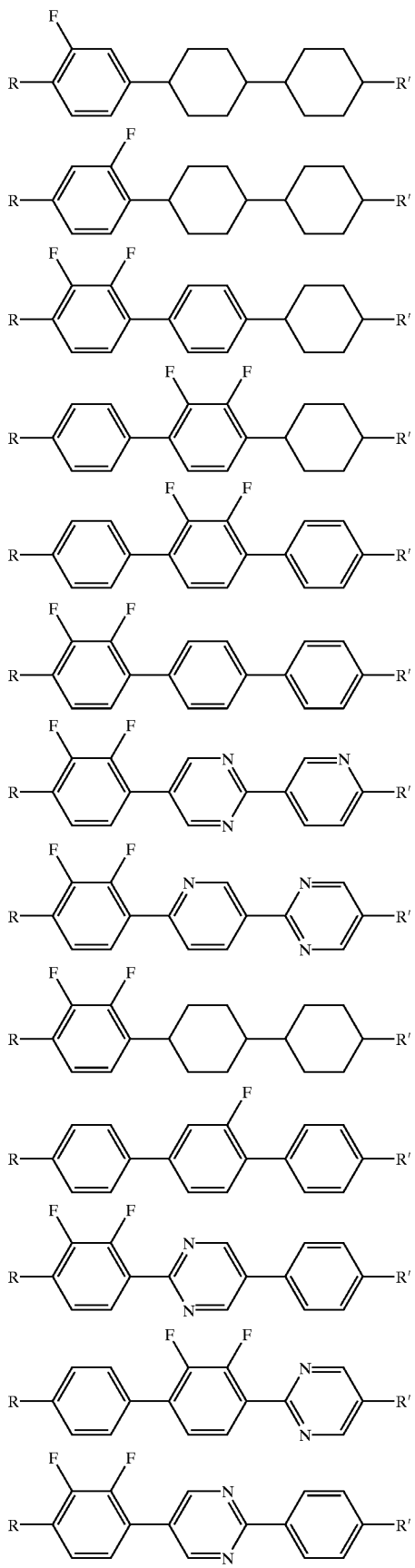

-continued

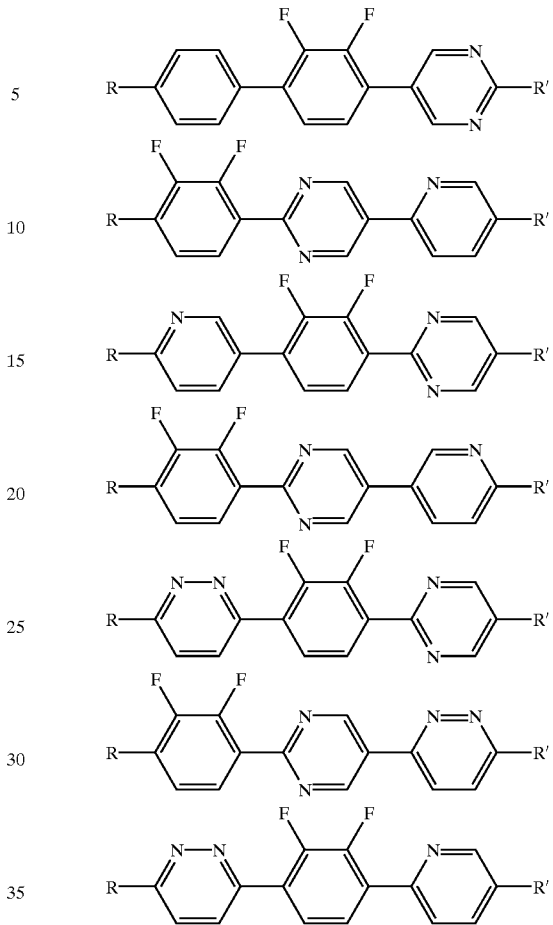

wherein R and R' have the same meaning as $R^1$ and $R^2$ in formula (IV).

Further particular preference is given to the compounds of the formula (IV) in which $R^1$ and $R^2$ are a straight-chain or branched-chain alkyl group having from 1 to 16 carbon atoms (with or without asymmetric carbon atoms), in which one or two —CH$_2$— groups may also be replaced by —O—, cyclopropane-1,2-diyl or —Si(CH$_3$)$_2$—, with the proviso that oxygen atoms must not be bonded directly to one another; one or more hydrogen atoms of the alkyl group may be substituted by F; $R^1$ or $R^2$ can also be hydrogen, but not both simultaneously.

Very particular preference is given to the following compounds of the formula (IV):

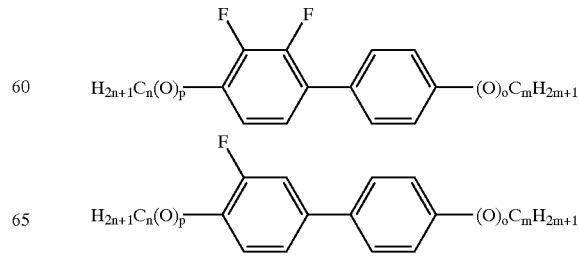

-continued

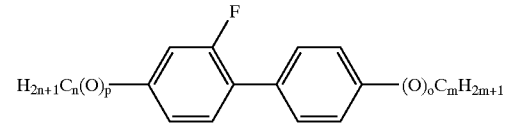
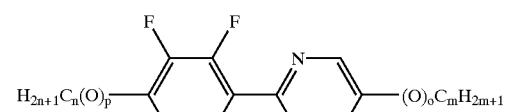
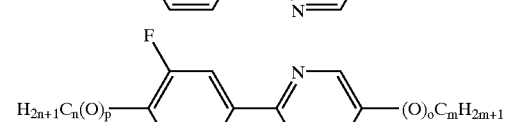
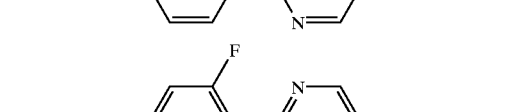
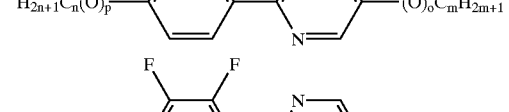
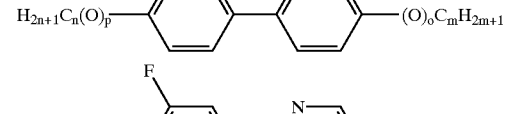
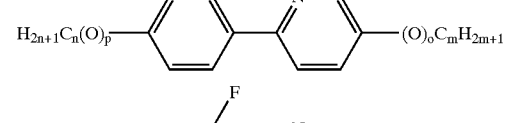
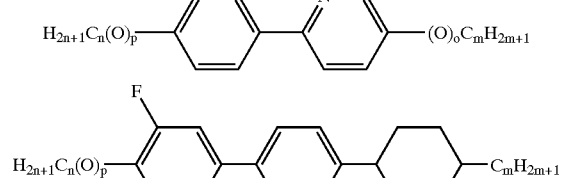
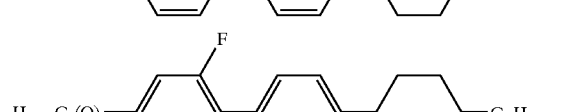
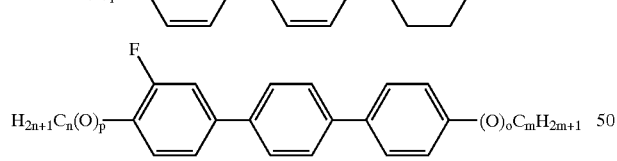
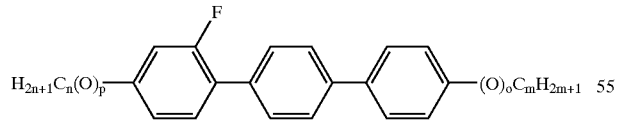
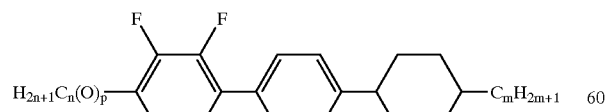
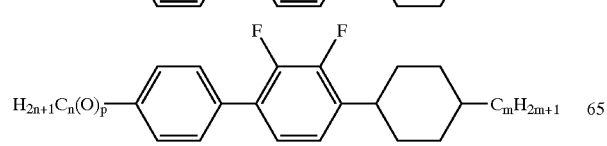

-continued

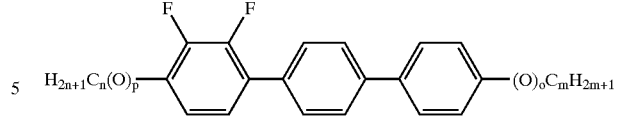
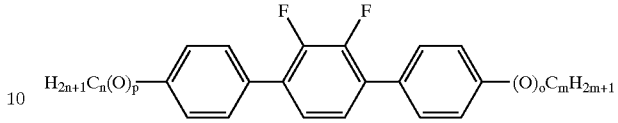
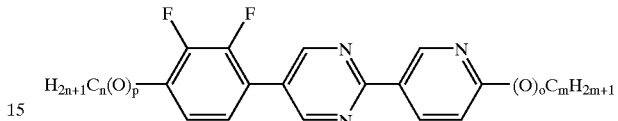
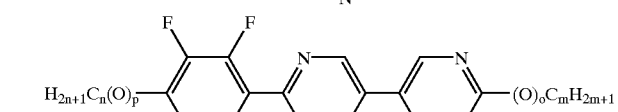
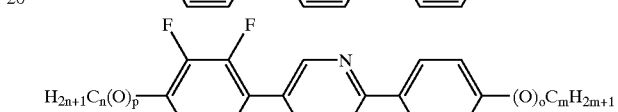
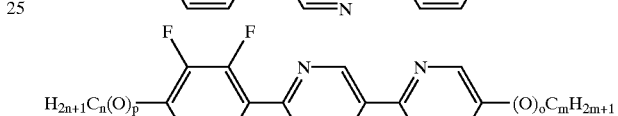
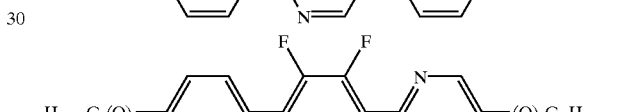
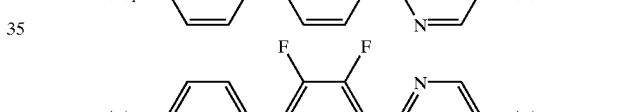

wherein n and m, independently from one another, are 0 to 16 (with the proviso that $3<n+m<29$) and o and p, independently from one another, are 0 or 1.

Preferred compounds of group E, i.e. of formula (V), are those, in which the symbols and indices in the formula (V) have the following meanings:

$X^3$ is
(a) —F or —F$_3$,
(b) a straight-chain or branched-chain alkyl group (with or without an asymmetric carbon atom) having from 1 to 10 carbon atoms, in which
  b1) one or two non-adjacent and non-terminal —CH$_2$— groups may be replaced by —O—, —CO—O— or —O—CO— and/or
  b2) one or more hydrogen atoms of the alkyl group may be substituted by F;

$R^1$ is
(a) a hydrogen atom,
(b) a straight-chain or branched-chain alkyl group (with or without an asymmetric carbon atom) having from 1 to 16 carbon atoms, in which
  b1) one or two non-adjacent and non-terminal —CH$_2$— groups may be replaced by —O—, —CO—O—, —O—CO— or —Si(CH$_3$)$_2$— and/or
  b2) one or more hydrogen atoms of the alkyl group may be substituted by F and/or b4) the terminal CH$_3$-group may be replaced by any one of the following chiral groups (optically active or racemic):

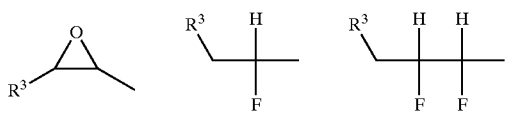

with the proviso that R$^1$ can not be a hydrogen atom if X$^3$ is —F or —CF$_3$;

R$^3$, R$^4$, R$^5$, R$^6$, R$^7$, independently of one another, are
  a) a hydrogen atom,
  b) a straight-chain or branched-chain alkyl group (with or without an asymmetric carbon atom) having from 1 to 12 carbon atoms, where
    b1) one non-terminal —CH$_2$— group may be replaced by —O—,
  c) R$^4$ and R$^5$ may also together be —(CH$_2$)$_4$— or —(CH$_2$)$_5$— if they are bonded to an oxirane, dioxolane, tetrahydrofuran, tetrahydropyrane, butyrolactone or valerolactone system;

M$^1$, M$^2$, M$^3$ independently of one another, are
  —CO—O—, —O—CO—, —CH2—O—, —O—CH$_2$— or a single bond;

A$^1$, A$^2$, A$^3$, independently of one another, are
  1,4-phenylene, in which one or two H atoms may be replaced by F, pyridine-2,5-diyl, in which one H atom may be replaced by F, pyrimidine-2,5-diyl, trans-1,4-cyclohexylene, naphtalene-2,6-diyl, thiophene-2,5-diyl, [1,3,4]-thiadiazole-2,5-diyl or [1,3]-thiazole-2,5-diyl.

Examples of particularly preferred compounds of the formula (V) include:

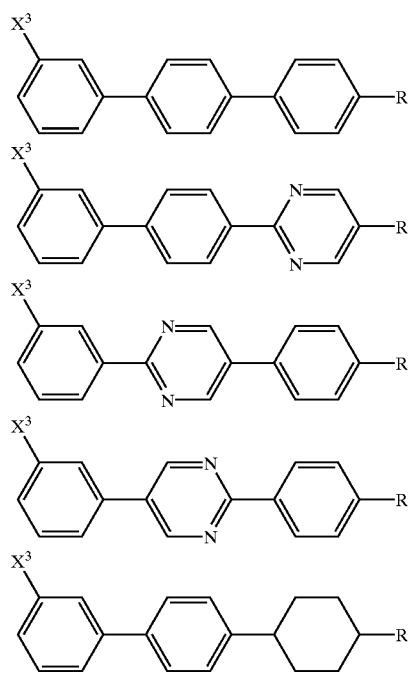

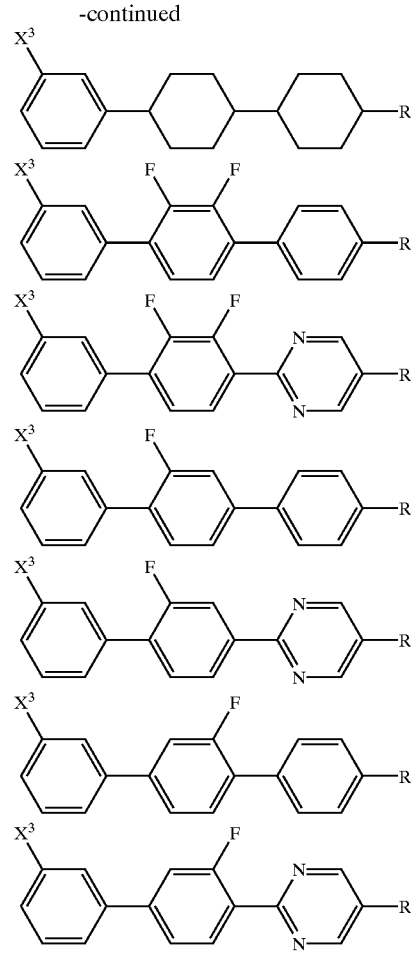

wherein R has the same meaning as R$^1$ in formula (V).

Further particular preference is given to the compounds of the formula (V) in which R$^1$ and R$^2$ are a straight-chain or branched-chain alkyl group having from 1 to 16 carbon atoms (with or without an asymmetric carbon atom), in which one or two —CH$_2$— groups may also be replaced by —O— or —Si(CH$_3$)$_2$—, with the proviso that oxygen atoms must not be bonded directly to one another; one or more hydrogen atoms of the alkyl group may be substituted by F.

Preferred are those compounds of group F, in which the symbols and indices in the formula (VI) have the following meanings:

R$^1$ and R$^2$, independently of one another, are
  (a) a hydrogen atom,
  (b) a straight-chain or branched-chain alkyl group (with or without an asymmetric carbon atom) having from 1 to 16 carbon atoms, in which
    b1) one or two non-adjacent and non-terminal —CH$_2$— groups may be replaced by —O—, —CO—O—, —O—CO— or —Si(CH$_3$)$_2$— and/or
    b2) one —CH$_2$— group may be replaced by trans-1,4-cyclohexylene, 1,4-phenylene or cyclopropane-1,2-diyl and/or
    b3) one or more hydrogen atoms of the alkyl group may be substituted by F and/or
    b4) the terminal CH$_3$-group may be replaced by any one of the following chiral groups (optically active or racemic):

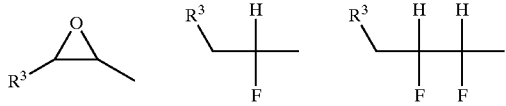

with the proviso that only one of $R^1$, $R^2$ can be a hydrogen atom;

$R^3$, $R^4$, $R^5$, $R^6$, $R^7$, independently of one another, are
a) a hydrogen atom,
b) a straight-chain or branched-chain alkyl group (with or without an asymmetric carbon atom) having from 1 to 12 carbon atoms, where
b1) one non-terminal —$CH_2$— group may be replaced by —O—,
c) $R^4$ and $R^5$ may also together be —$(CH_2)_4$— or —$(CH_2)_5$— if they are bonded to an oxirane, dioxolane, tetrahydrofuran, tetrahydropyrane, butyrolactone or valerolactone system;

$M^1$, $M^2$, independently of one another, are
—CO—O—, —O—CO—, —$CH_2$—O—, —O—$CH_2$— or a single bond;

$A^1$, $A^2$, $A^3$, independently of one another, are
1,4-phenylene, in which one or two H atoms may be replaced by F, pyridine-2,5-diyl, in which one H atom may be replaced by F, pyrimidine-2,5-diyl, trans-1,4-cyclohexylene, naphtalene-2,6-diyl, thiophene-2,5-diyl, [1,3,4]-thiadiazole-2,5-diyl or [1,31]-thiazole-2,5-diyl.

Examples of particularly preferred compounds of the formula (VI) include:

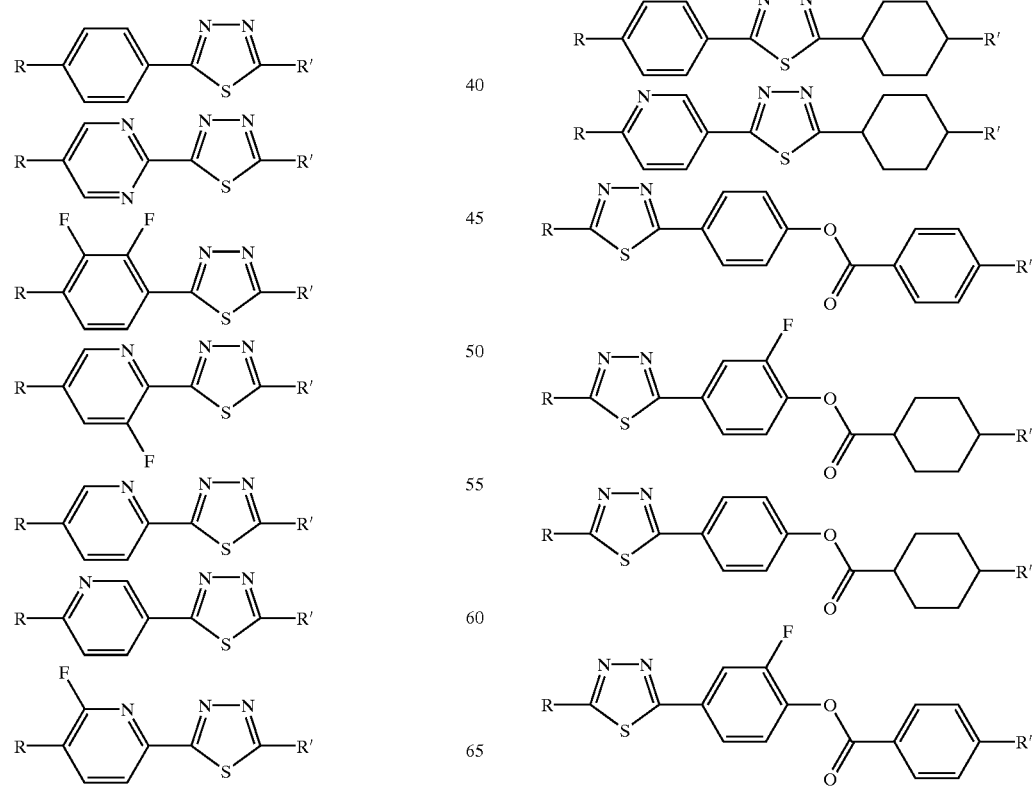

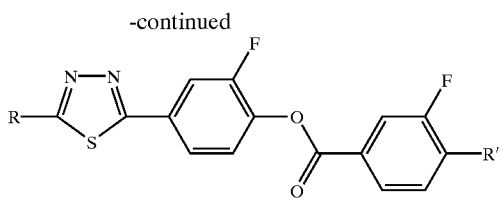

wherein R and R' have the same meaning as $R^1$ and $R^2$ in formula (VI).

Further particular preference is given to the compounds of the formula (VI) in which $R^1$ and $R^2$ are a straight-chain or branched-chain alkyl group having from 1 to 16 carbon atoms (with or without an asymmetric carbon atom), in which one or two —$CH_2$— groups may also be replaced by —O—, cyclopropane-1,2-diyl or —Si($CH_3$)$_2$—, with the proviso that oxygen atoms must not be bonded directly to one another; one or more hydrogen atoms of the alkyl group may be substituted by F; $R^1$ or $R^2$ can also be hydrogen, but not both simultaneously.

Very particular preference is given to the following compounds of the formula (VI):

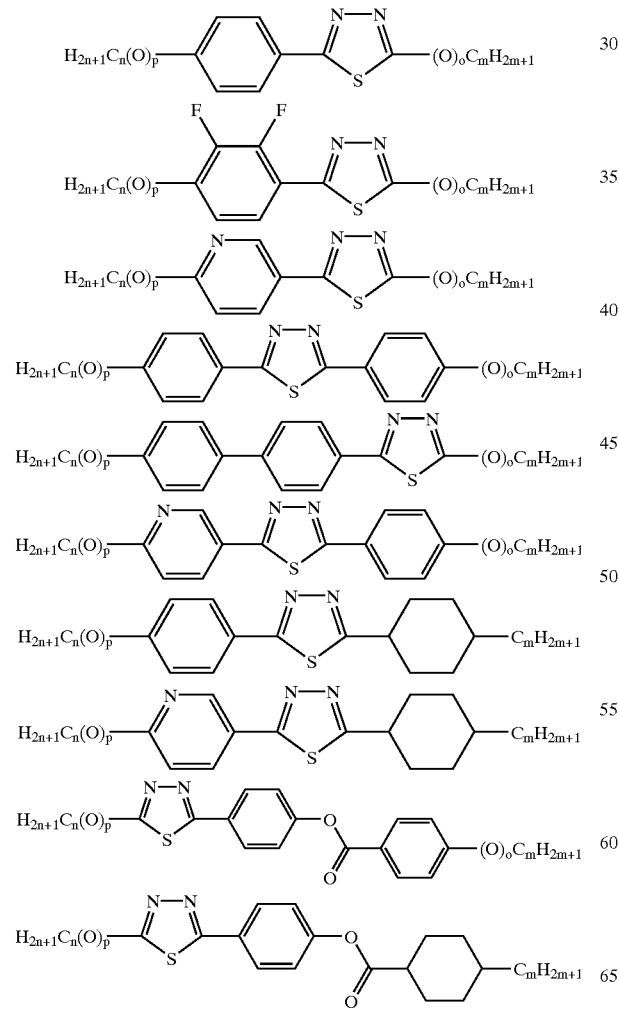

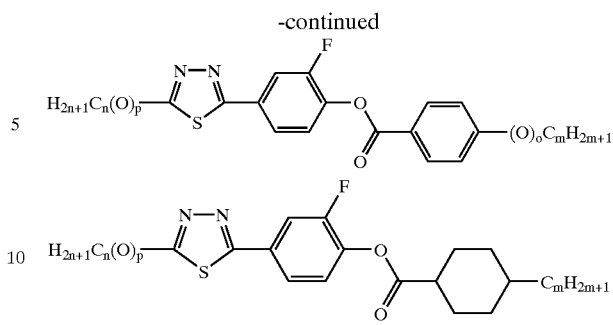

wherein n and m, independently from one another, are 0 to 16 (with the proviso that 3<n+m<29); and o and p, independently from one another, are 0 or 1.

Preferred are those compounds of group G, in which the symbols and indices in the formula (VII) have the following meanings:

$R^1$ is
  (a) a hydrogen atom,
  (b) a straight-chain or branched-chain alkyl group (with or without an asymmetric carbon atom) having from 1 to 16 carbon atoms, in which
    b1) one or two non-adjacent and non-terminal —$CH_2$— groups may be replaced by —O—, —CO—O—, —O—CO— or —Si($CH_3$)$_2$— and/or
    b2) one —$CH_2$— group may be replaced by trans-1,4-cyclohexylene, 1,4-phenylene or cyclopropane-1,2-diyl and/or
    b3) one or more hydrogen atoms of the alkyl group may be substituted by F and/or
    b4) the terminal $CH_3$-group may be replaced by any one of the following chiral groups (optically active or racemic):

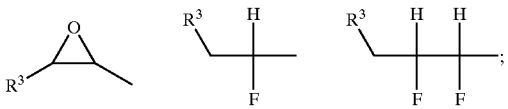

$R^2$ is
  (a) a hydrogen atom,
  b) a straight-chain or branched-chain alkyl group (with or without an asymmetric carbon atom) having from 1 to 14 carbon atoms, in which
    b1) one or two non-adjacent and non-terminal —$CH_2$— groups may be replaced by —O—, —CO—O—, —O—CO— or —Si($CH_3$)$_2$— and/or
    b2) one or more hydrogen atoms of the alkyl group may be substituted by F;

$R^3$, $R^4$, $R^5$, $R^6$, $R^7$, independently of one another, are
  a) a hydrogen atom,
  b) a straight-chain or branched-chain alkyl group (with or without an asymmetric carbon atom) having from 1 to 12 carbon atoms, where
    b1) one non-terminal —$CH_2$— group may be replaced by —O—,
  c) $R^4$ and $R^5$ may also together be —($CH_2$)$_4$— or —($CH_2$)$_5$— if they are bonded to an oxirane, dioxolane, tetrahydrofuran, tetrahydropyrane, butyrolactone or valerolactone system;

$M^1$, $M^2$, independently of one another, are —CO—O—, —O—CO—, —$CH_2$—O—, —O—$CH_2$— or a single bond;

$A^1$, $A^2$, independently of one another, are 1,4-phenylene, in which one or two H atoms may be replaced by F, pyridine-2,5-diyl, in which one H atom may be replaced by F, pyrimidine-2,5-diyl, 1,4-cyclohexylene, naphtalene-2,6-diyl, thiophene-2,5-diyl, [1,3,4]-thiadiazole-2,5-diyl or [1,3]-thiazole-2,5-diyl.

Examples of particularly preferred compounds of the formula (VII) include:

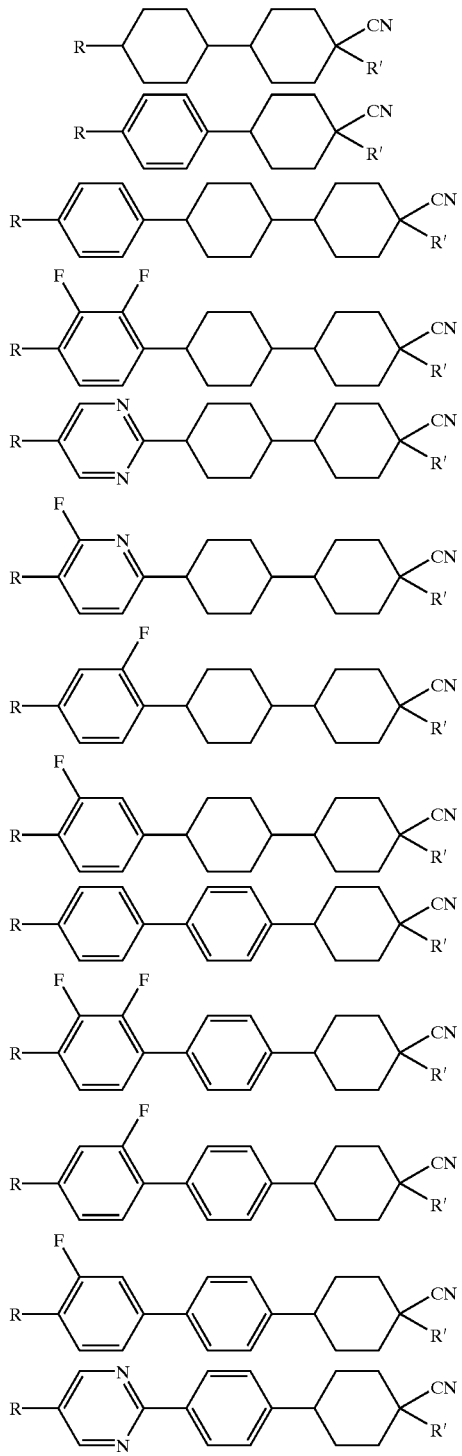

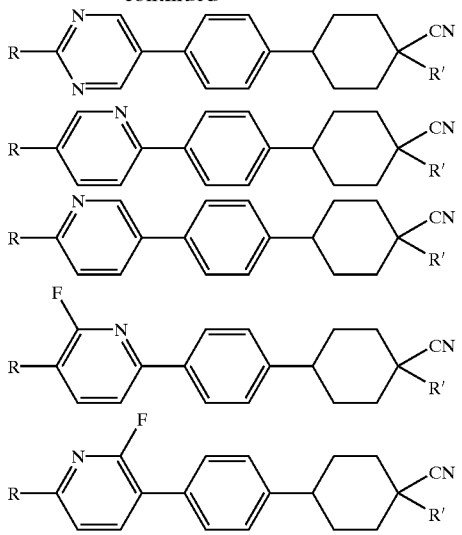

wherein R and R' have the same meanings as $R^1$ and $R^2$ in formula (VII).

Further particular preference is given to the compounds of the formula (VII) in which $R^1$ and $R^2$ are a straight-chain or branched-chain alkyl group having from 1 to 16 carbon atoms (with or without asymmetric carbon atoms), in which one or two —$CH_2$— groups may also be replaced by —O—, cyclopropane-1,2-diyl or —Si($CH_3$)$_2$—, with the proviso that oxygen atoms must not be bonded directly to one another; one or more hydrogen atoms of the alkyl group may be substituted by F; $R^1$ or $R^2$ can also be hydrogen, but not both simultaneously.

Very particular preference is given to the following compounds of the formula (II):

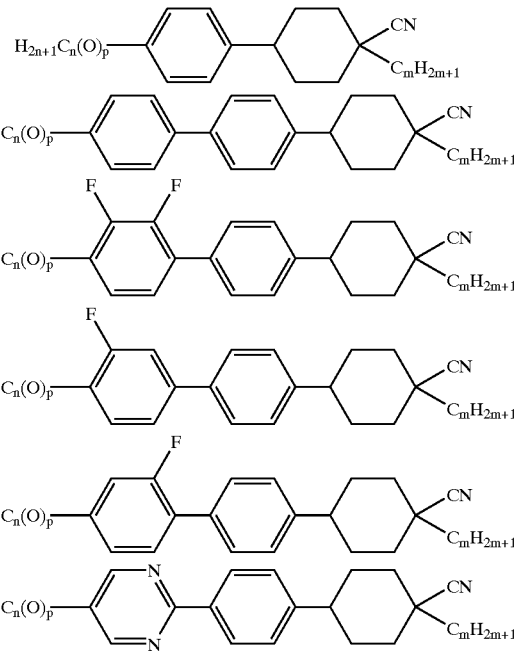

-continued

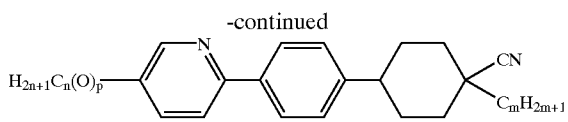

wherein n and m, independently from one another, are 0 to 16 (with the proviso that 3<n+m<29); p is 0 or 1.

The compounds of groups A to G are either known or can be prepared in a manner known per se, analogously to known compounds.

The compounds and synthesis thereof are described, e.g., in:

EP-A 0 546 338 and EP-A 0 647 695 (component A); especially EP-A-0 546 338 and

DE-A-197 48 432 (component A, formula IA);

DE-A 195 00 768 (component B);

U.S. Pat. No. 5,389,291 and WO-A 92/11 241 (component C);

EP-A 0 332 024 and J. Chem. Soc. Perkin Trans. 11 1989, 2041 (component D);

EP-A 0 578 054 (component E);

EP-A 0 309 514 and DE-A 37 03 651 (component F); and

EP-A 0 233 267 (component G);

all of which are incorporated herein by reference.

The smectic, nematic, or preferably ferroelectric liquid crystal mixtures according to the invention are prepared in a manner which is customary per se. As a rule the components are dissolved in one another, advantageously at elevated temperatures.

As stated above the ferroelectric liquid crystal mixture according to the invention comprises one or more compounds from group A and one or more compounds from groups B to G.

Preferably the mixture comprises 2 to 35, more preferably 2 to 30 and in particular 3 to 25 and especially 4 to 20 compounds of groups A to G.

Preferably the mixture's content of compounds of groups A to G is 5% by weight or more, more preferably 10% or more, particularly 15% or more.

In a preferred embodiment the mixture according to the invention comprises compounds from 2, 3 or 4 different groups B to G.

In a preferred embodiment the mixture according to the invention comprises at least one compound from each group:

| a) A + B | b) A + C | c) A + D |
| d) A + E | e) A + F | f) A + G |

In a further preferred embodiment the mixture according to the invention includes one or more compounds from group A, one or more compounds from group B and one or more compounds from groups C, D, E, F or G.

In a further preferred embodiment the mixture according to the invention includes one or more compounds from group A, one or more compounds from group C and one or more compounds from groups B, D, E, F or G.

In a further preferred embodiment the mixture according to the invention includes one or more compounds from group A, one or more compounds from group D and one or more compounds from groups B, C, E, F or G.

In a further preferred embodiment the mixture according to the invention includes one or more compounds from group A, one or more compounds from group E and one or more compounds from groups B, C, D, F or G.

In a further preferred embodiment the mixture according to the invention includes one or more compounds from group A one or more compounds from group F and one or more compounds from groups B, C, D, E or G.

In a further preferred embodiment the mixture according to the invention includes one or more compounds from group A, one or more compounds from group G and one or more compounds from groups B, C, D, E or F.

In a further preferred embodiment the mixture according to the invention comprises 3 or more compounds from each group:

| a) A + B + C | b) A + B + D | c) A + B + E | d) A + B + F |
| e) A + B + G | f) A + C + D | g) A + C + E | h) A + C + F |
| i) A + C + G | j) A + D + E | k) A + D + F | l) A + D + G |
| m) A + E + F | n) A + E + G | o) A + F + G. | |

In a further preferred embodiment the mixture according to the invention comprises 4 or more compounds from each group:

| a) A + B + C + D | b) A + B + C + E | c) A + B + C + F |
| d) A + B + C + G | e) A + B + D + E | f) A + B + D + F |
| g) A + B + D + G | h) A + B + E + F | i) A + B + E + G |
| j) A + B + F + G | k) A + C + D + E | l) A + C + D + F |
| m) A + C + D + G | n) A + C + E + F | o) A + C + E + G |
| p) A + C + F + G | q) A + D + E + F | r) A + D + E + G |
| s) A + D + F + G | t) A + E + F + G. | |

The liquid crystal mixtures according to the invention generally consists of 2 to 35, preferably from 2 to 30, particularly preferably from 3 to 25 compounds. Preferably 1 to 10, more referably 1 to 5, particularly preferably 1 to 3 of the compounds of formula (IA) may be present.

Since the mixture according to the invention is ferroelectric it must contain at least one optically active compound. Generally the mixture contains one or more optically non-active compounds (base mixture) and one or more optically active compounds (chiral dopants).

Further suitable components for the liquid crystal mixtures according to. the invention include, for example:

derivatives of phenylpyrimidine, as described, for example, in WO 86/06401 and U.S. Pat. No. 4,874,542, silicon compounds, as described, for example, in EP-A 0 355 008, mesogenic compounds containing only one side chain as described, for example, in EP-A 0 541 081, hydroquinone derivatives, as described, for example, in EP-A 0 603 786, pyridylpyrimidines, as described, for example, in WO 92/12974, phenylbenzoates, as described, for example, in P. Keller, Ferroelectrics 58 (1984), 3, and J. W. Goodby et al., Liquid Crystals and Ordered Fluids, Vol. 4, New York, 1984, thiazoles, as described, for example, in EP-A 0 430 170, fluorinated compounds, especially terphenyles, as described, for example, in EP-A 0 132 377, 4-cyano-cyclohexyl derivatives, as described, for example, in EP-A 0 233 267, 2-fluoro-pyrazines, as described, for example in EP-A 0 532 916, naphthalene compounds, as described, for example, in DE-A 42 40 041, and thiophene compounds, as described, for example in EP-A 0 400 072.

Examples of suitable chiral, non-racemic dopants include:

optically active phenylbenzoates, as described, for example, in P. Keller, Ferroelectrics 58 (1984), 3, and J. W. Goodby et al., Liquid Crystals and Ordered Fluids, Vol. 4, New York, 1984, optically active oxirane ethers, as described, for example, in EP-A 0 263 437 and WO-A 93/13093, optically active oxirane esters, as described, for example, in EP-A 0 292 954, optically active dioxolane ethers, as described, for example, in EP-A0 351 746, optically active dioxolane esters, as described, for example, in EP-A 0 361 272, optically active tetrahydrofuran-2-carboxylic esters, as described, for example, in EP-A 0 355 561, optically active 2-fluoroalkyl ethers, as described, for example, in EP-A 0 237 007 and U.S. Pat. No. 5,051,506, and optically active 4-cyano-cyclohexyl compounds, as described, for example, in EP-A 0 428 720.

Preferred additional compounds are one or more phenylpyrimidine compounds of the formula (VIII):

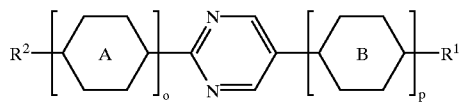
(VIII)

wherein $R_1$ and $R_2$ are as defined under formula (I);

rings A and B. independently of one another, are 1,4-phenylene or 1,4-cyclohexylene;

o and p are 0, 1 or 2, with the proviso that $0<o+p\leq2$; if o or p is 2 then the A or B groups can be different.

Examples of particularly preferred compounds of the formula (VIII) include:

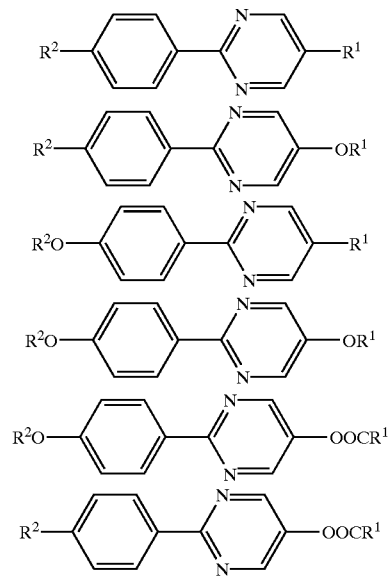

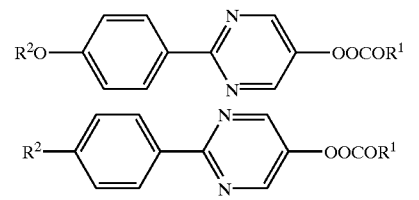

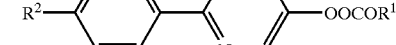

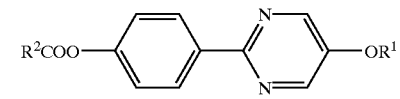

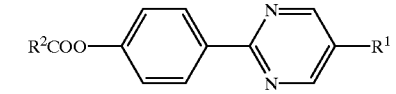

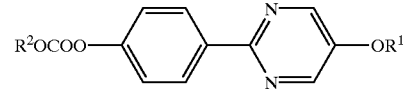

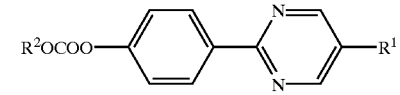

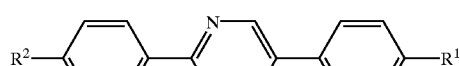

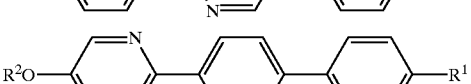

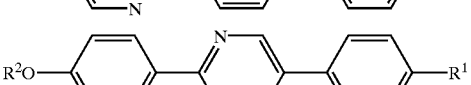

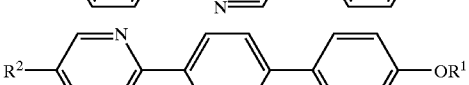

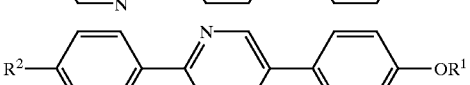

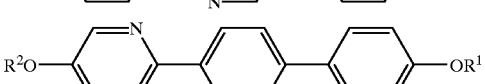

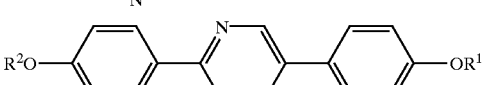

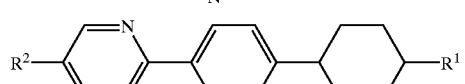

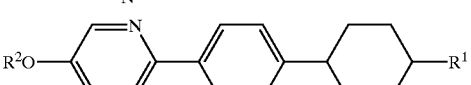

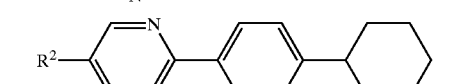

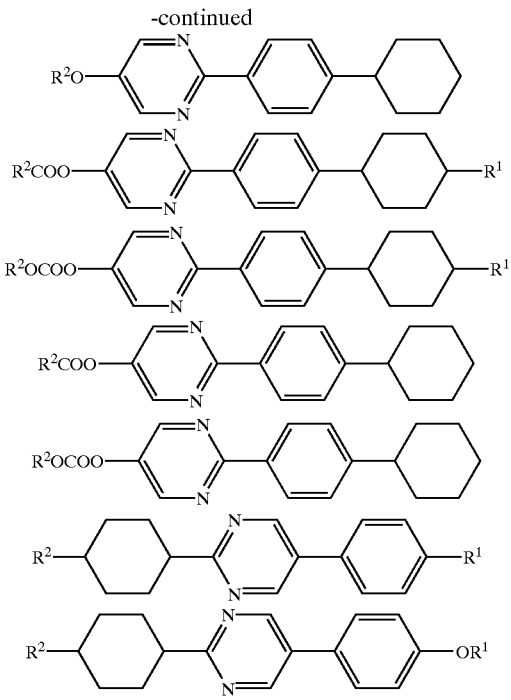

wherein $R^1$ and $R^2$, independently of each other, are alkyl groups having from 0 to 16 carbon atoms where one or two hydrogen atoms of the alkyl groups may be substituted by F; $R^1$ or $R^2$ can also be hydrogen, but not both simultaneously.

It is preferable that the liquid crystal mixture of the present invention has a negative $\Delta\in$. It is further preferable that the absolute value thereof is 2 or above, particularly 4 or above, at a temperatur in the working range of the display, preferably at a temperature in the range between 10° C. and 40° C., particularly preferred at 25° C.

It is preferable that the liquid crystal mixture employed in the ferroelectric liquid crystal display device has a phase sequence of $I—N^*—S_A—S_C^*$ (with decreasing temperature), a sufficiently broad $N^*$ phase and a broad $S_A$ phase, and sufficiently long helical pitches in the $N^*$ and $S_C^*$ phases, (preferably at least five times, more preferred ten times, the layer thickness of the FLC-layer) since good alignment characteristics can thus be achieved. (I stands for the isotropic phase, $N^*$ stands for the chiral nematic phase, SA stands for the smectic A phase, and $S_C^*$ stands for the chiral smectic C phase.) In particular, the smectic A phase and the nematic phase should have a temperature range of at least 1° C. without two phases coexisting, preferably 3° C. or more, more preferred 5° C. or more.

Use of the compounds of groups A to G, optionally together with the compounds of the general formula (VIII), in accordance with the present invention allows enlargement of the absolute value of the negative $\Delta\in$ of ferroelectric liquid crystals. In the conventional methods, the spontaneous polarization value of liquid crystals is selected to be sufficiently low so as to give a low driving voltage. However, the present invention makes it possible to improve the response speed by increasing the spontaneous polarization value without elevating the driving voltage. In the present invention, the spontaneous polarization value ranges preferably from 1 to 30 $nC/cm^2$, particularly preferably from 5 to 20 $nC/cm^2$.

With an increase in spontaneous polarization value, it is sometimes observed that sufficiently enough contrast cannot be obtained due to sticking or insufficient memory properties. It is, therefore, preferable that the ferroelectric liquid crystal mixture of the present invention contains at least one compound as described, e.g., in EP-A 0 502 964, EP-A 0 385 688 or WO-A 93/04142. These documents are hereby incorporated by reference.

Examples of these compounds include, in particular, ethylene glycol dimethyl ether and triethylene glycol dimethyl ether, and crown ethers (for example, 1 2-crown-4, 15-crown-5, 18-crown-6, etc.) and derivatives thereof.

It is preferable that the liquid crystal mixture according to the invention contains from 0.01 to 5% by weight, particularly from 0.1 to 2% of the above compounds.

It is also preferable that the pretilt angle of liquid crystal molecules at the interface between the liquid crystal and the alignment layer is 10° or less, preferably 0.1° to 8°.

In a preferred embodiment the mixtures according to the invention show a ratio $\theta_{(5V)}/\theta_{(0V)}$ of 1.4 or more preferably 1.8 or more, particularly preferably 2.0 or more.

The mixtures according to the invention can be used in electro-optical or fully optical elements, for example display elements, switching elements, light modulators, elements for image processing and/or signal processing or generally in the area of nonlinear optics.

Ferroelectric liquid crystal mixtures according to the invention are particularly suitable for use in electro-optical switching and display devices (displays). These displays are usually constructed in such a way that a liquid crystal layer is enclosed on both sides. by layers which are usually, in this sequence starting from the LC layer, at least one alignment layer, electrodes and a limiting sheet (for example of glass). In addition, they contain spacers, adhesive frames, polarizers and, for color displays, thin color-filter layers. Other possible components are antireflection, passivation, compensation and barrier layers and electric non-linear elements, such as thin-film transistors (TFTs) and metal-insulator-metal (MIM) elements. The structure of liquid crystal displays has already been described in detail in relevant monographs (see, for example, E. Kaneko, "Liquid Crystal TV Displays: Principles and Applications of Liquid Crystal Displays", KTK Scientific Publishers 1987).

They are especially useful for applications in the inverse or $\tau\text{-}V_{(min)}$ mode.

The present invention further provides a ferroelectric liquid crystal (FLC) display device comprising the above-mentioned liquid crystal mixture of the present invention between a pair of substrates each comprising an electrode and an alignment layer formed thereon.

In a preferred embodiment the FLC display is operated in the inverse mode.

Several documents are cited in this application, e.g. to discuss the state of the art, synthesis of compounds used in the present invention or application of the mixtures according to the invention. All these documents are hereby incorporated by reference.

Cell Fabrication

A solution of LQT 120 (Hitachi Kasei) is applied onto glass substrates with ITO by spin coating at 2500 rpm. The substrates are heated at 200° C. for 1 hour to form a film. After rubbing the coated film with a nylon cloth in one direction, the substrates are assembled into a cell with spacers having a thickness of 2.0 μm inserted between the substrates in such a manner that the rubbing directions are parallel to each other. The properties of the liquid crystal mixture is measured using the resulting cell. The voltage $(V_{min})$, which gives a minimum value $(\tau_{min})$ of the pulse width $(\tau)$ in the $\tau\text{-}V$ characteristics of a ferroelectric liquid crystal device, is measured by filling the liquid crystal mixture into the cell in an isotropic phase, cooling progressively through the nematic, smectic A and the smectic C phase and then applying a monopolar pulse to the cell at 25° C.

Phase transition temperatures were determined by optical polarizing microscopy and DTA.

The dielectric anisotropy ($\Delta\in$) is measured by filling the liquid crystal mixture into a homotropic orientation cell and a planar orientation cell (EHC, with a cell gap of 10 $\mu$m) and applying an electric field of 1V, 20 KHz to the cells at 25° C. The value for homotropic alignment is corrected for the tilt angle.

Spontaneous Polarization $P_s$

The Diamant bridge (or Sawver-Tower) method (H. Diamant, K. Prenck and R. Pepinsky, Rev. Sci. lnstr. 28, 30 (1957)) is used to determine $P_s$. The test cells have a thickness of 5 $\mu$m and are thinly coated with ITO.

$2\theta_{(5v)}$ was measured by optical inspection of two memory states under applying a high frequency rectangular pulse. The voltage of the rectangular pulse from peak to peak is 10 V.

The invention is further illustrated by the following examples.

EXAMPLES

Example 1

4-Fluoro-6-(5-nonyl-pyrimidine-2-yl)-2-octyl-indane 4-bromo-2-fluoro-benzylbromide [76283-09-5] is reacted in ethanol with stoichiometric compounds of natrium ethanolate and octylmalonic acid diethylester to form 2-(4-bromo-2-fluoro phenyl)methyl-2-octyl malonic acid diethylester. After usual post-treatment and distillation a 50% aqueous potassium hydroxide solution is added to the methanolic solution and heated until the saponification has ended. After cooling sulfuric acid is added to adjust the pH to a value of 1–2. The 4-fold volume of water is added followed by multiple extraction of methyl-tert.-butylether. The combined organic phases are dried and the solvent is removed under vacuum, finally at 60° C. in the heating bath. The 2-(4-bromo-2-fluoro phenyl)methyl-2-octyl-malonic acid thus obtained after heating for several hours at 150–170° C. is decarboxylated to obtain 3-(4-bromo-2-fluoro phenyl)-2-octyl-propionic acid.

This acid is heated with the 10-fold amount of polyphosphoric acid for several hours at 120 to 160° C. The solution cooled to 80° C. is poured into the 10-fold volume of water with stirring. After multiple extraction with toluene, the combined toluene-extracts are washed with 2n NaOH and subsequently with saturated brine. After drying, the solvent is removed by distillation in vacuum. After chromatographic cleaning (silica gel; dichloromethane/heptane 1:1) 6-bromo-4-fluoro-2-octyl-indane-1-one is obtained.

This ketone is dissolved in trifluoro acetic acid and an excess of triethylsilane is added. After completion of the reaction, the mixture is poured into the 10-fold amount of water and extracted with dichloromethane. The combined dichloromethane extracts are washed as described above and dried afterwards. After removing of the solvent by distillation and chromatographic cleaning (silica gel; dichloromethane/heptane; gradient, starting with 1:1) 6-bromo-4-fluoro-2-octyl-indane is obtained.

This product is reacted with n-butyllithium in tetrahydrofurane under inert gas at −70° C. After the lithiation trimethylborate is added at the same temperature. At the end of the reaction, at last at room temperature, the pH is adjusted to 2 by adding 15% hydrochloric acid dropwise. After extracting with methyl-tert.-butylether, washing of the combined organic phases with water and drying as well as distillating the solvent under vacuum 4-fluoro-2-octyl-indane-6-boronic acid is obtained. A purification can be performed by chromatography or stirring (optionally at −20° C.).

The raw, brown-colored end product is obtained by heating of this boronic acid with 2-chloro-5-nonyl-pyrimidine (available e.g. from Midori Kagaku) with catalytic amounts of tetrakis(triphenylphosphine)palladium(0) mixed in ethanol/toluene/water in the presence of sodium carbonate, diluting the mixture with the 4-fold amount of water, extracting with dichloromethane, washing the combined organic phases with water, drying and distillation of the solvent under vacuum. The cleaning is performed by chromatography (silica gel, toluene) and crystallization (propanone-2).

Starting from 4-fluoro-2-octyl-indane-6-boronic acid or alkyl chain homologs, the following compounds may be obtained analogous to the last step of example 1:

Example 2

4-Fluoro-6-(5-octyl-pyridine-2-yl)-2-octyl-indane

Obtained by reacting with 2,5-dibromopyridine to form 4-fluoro-6-(5-bromo-pyridine-2-yl)-2-octyl indane and subsequent reaction with the octene-9-BBN-adduct.

Example 3

4-Fluoro-6-(4-decyloxyphenyl)-2-octyl-indane

Obtained by reacting with 4-decyloxybromobenzene.

Example 4

6-(3-Fluoro-4-octyloxyphenyl)-4-fluoro-2-octyl-indane

Obtained by reacting with 3-fluoro-4-octyloxybromobenzene.

Starting from this compound 6-bromo-4-fluoro-2-octyl-indane and alkyl chain homologs thereof can be obtained.

Example 5

4-Fluoro-6-(6-fluoro-2-octyl-pyridine-5-yl)-2-octyl-indane

Obtained by reacting with 6-fluoro-2-octyl-pyridine-5-boronic acid (obtainable according to U.S. Pat. No. 5,630,962) analogous to the last step of example 1.

Example 6

1-(4-Ethylphenyl)-2-(4-fluoro-2-methyl-indane-6-yl)ethane

Obtained by reacting with 1-(4-ethylphenyl)ethane under the conditions modified for the Heck-coupling according to the last step of example 1 (see also DE-A-44 38 877).

Example 7

1-(2,3-Difluoro-4-propylphenyl)-2-(4-fluoro-2-methyl-indane-6-yl)ethane

Obtained by reacting with 1-(2,3-difluoro-4-propylphenyl) ethane analogous to example 5 and subsequent hydrogenation.

Example 8

1-(2,3-Difluoro-4-octylphenyl)-2-(4-fluoro-2-octyl-indane-6-yl)ethane

Obtained analogous to example 6.

Example 9

1-(4-Fluoro-2-ethyl-indane-6-yl)-2-(3-fluoro-4-propylphenyl)ethane

Obtained by reaction with 1-(3-fluoro-4-propylphenyl) ethane and subsequent treatment analogous to example 6.

Example 10

1-(4-Fluoro-2-ethyl-indane-6-yl)-2-(4-propylphenyl) ethane

Obtained by reaction with 1-(4-4-propylphenyl) ethane and subsequent treatment analogous to example 6.

Example 11

6-Decyl-4-fluoro-2-octyl-indane

Obtained via nickel-catalyzed coupling of decyl-magnesium-bromide.

Example 12

4-Fluoro-2-pentyl-6-propyl-indane

Obtained analogous to example 10.

Example 13

4-Fluoro-2-(4-trans-propylcyclohexyl)-6-octyl-indane

Obtained analogous to example 11 using 2-(trans-4-propylcyclohexyl)malonic acid diethylester (obtained according to JP-A-59070684) in the reaction sequence of example 1.

Example 14

4-Fluoro-6-propyl-2-(4-trans-propylcyclohexyl) indane

Obtained analogous to example 11 using 2(trans-4-propylcyclohexyl)malonic acid diethylester (obtained analogous to JP-A-59070684) in the reaction sequence of example 1.

What is claimed is:

1. A ferroelectric liquid crystal mixture comprising a compound of group A:

A. 5-arylindane derivatives of the formula (I),

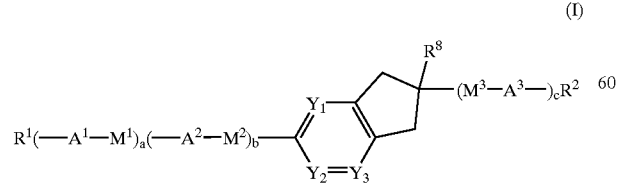

(I)

wherein the symbols and indices have the following meanings, $R^1$ and $R^2$, independently of one another, are
(a) a hydrogen atom, —F, —Cl, —CN, —$CF_3$ or —$OCF_3$,
(b) a straight-chain or branched-chain alkyl group (with or Without an asymmetric carbon atom) having from 1 to 20 carbon atoms, in which
b1) one or more non-adjacent and non-terminal —$CH_2$— groups may be replaced by —O—, —S—, —CO—, —CO—O—, —O—CO—, —O—CO—O— or —Si($CH_3$)$_2$— and/or
b2) one or more —$CH_2$— groups may be replaced by —CH=CH—, —C≡C—, 1,4-cyclohexylene, 1,4-phenylene, cyclopropane-1,2-diyl or 1,3-cyclopentylene and/or
b3) one or more hydrogen atoms of the alkyl group may be substituted by F and/or Cl and/or
b4) the terminal $CH_3$-group may be replaced by any one of the following chiral groups (optically active or racemic):

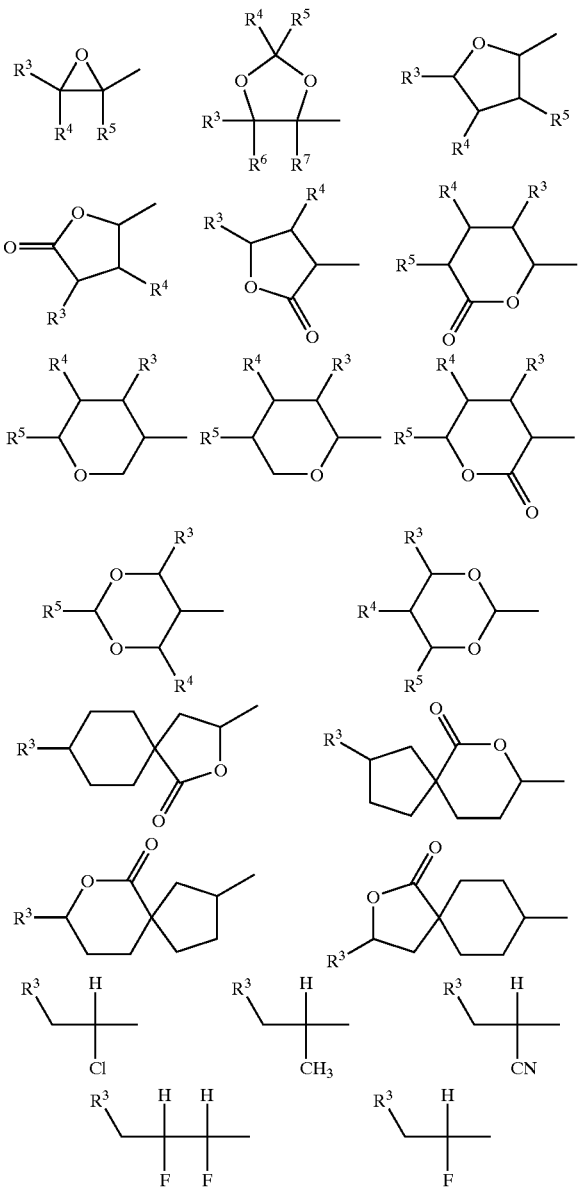

with the proviso that only one of $R^1$, $R^2$ can be a hydrogen atom, —F, —Cl, —CN, —$CF_3$ or —$OCF_3$;

$R^3$, $R^4$, $R^5$, $R^6$, $R^7$, independently of one another, are
  a) a hydrogen atom,
  b) a straight-chain or branched-chain alkyl group (with or without an asymmetric carbon atom) having from 1 to 16 carbon atoms, where
    b1) one or more non-adjacent and non-terminal —CH$_2$— groups may be replaced by —O— and/or
    b2) one or two —CH$_2$— groups may be replaced by —CH=CH— and/or
    b3) one or more hydrogen atoms of the alkyl group may be substituted by F or Cl,
  c) $R^4$ and $R^5$ may also together be —(CH$_2$)$_4$— or —(CH$_2$)$_5$— if they are bonded to an oxirane, dioxolane, tetrahydrofuran, tetrahydropyrane, butyrolactone or valerolactone system;

$R^8$ is
  a) a hydrogen atom, a halogen atom or CN
  b) a straight-chain or branched-chain alkyl group (with or without asymmetric carbon atoms) having from 1 to 16 carbon atoms, where
    b1) one or more non-adjacent and non-terminal —CH$_2$— groups may be replaced by —O—, —S—, —CO—, —CO—O— or —O—CO— and/or
    b2) one or more —CH$_2$— groups may be replaced by —CH=CH— or —C≡C— and/or
    b3) one or more hydrogen atoms of the alkyl group may be substituted by F and/or Cl;

$Y^1$, $Y^2$ and Y3, independently of one another, are —CF— or —CH—;
  with the proviso that at least one of $Y^1$, $Y^2$ and $Y^3$ is —N— or —CF—;

$M^1$, $M^2$, $M^3$, independently of one another, are —CO—O—, —O—CO—, —CH$_2$—O—, —O—CH$_2$—, —CH$_2$—CH$_2$—, —CH=CH—, —C≡C—; —CH$_2$—CH$_2$—CO—O—, —O—CO—CH$_2$—CH$_2$— or a single bond;

$A^1$, $A^2$, $A^3$, independently of one another, are
  1,4-phenylene, in which one or more H atoms may be replaced by F, Cl and/or CN, pyridine-2,5-diyl, in which one H atom may be replaced by F, pyrimidine-2,5-diyl, pyrazine-2,5-diyl, in which one H atom may be replaced by F, pyridazin-3,6-diyl, in which one H atom may be replaced by F, 1,4-cyclohexylene, in which one or two hydrogen atoms may be substituted by CN and/or F and/or CH$_3$, naphthalene-2,6-diyl, in which one or more H atoms may be replaced by F, Cl and/or CN, thiophene-2,5-diyl, in which one or two H atoms may be replaced by F, [1,1,3,4]-thiadiazole-2,5-diyl, [1,3]-thiazole-2,4-diyl, in which one H atom may be replaced by F, [1,3]-thiazole-2,5-diyl, in which one H atom may be replaced by F, or 1,3-dioxane-2,5-diyl;

a, b, c are 0 or 1 with the proviso, that compounds of the formula (I) do not contain more than four five- or six-membered ring systems;

and a further compound of any of the groups B to G:

B. phenanthrene derivatives of the formula (II)

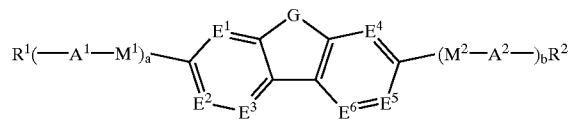

(II)

in which the symbols and indices have the following meanings:

$E^1$, $E^2$, $E^3$, $E^4$, $E^5$ and $E^6$ are —N—, —CF— or —CH—, with the following provisos:
  if $E^1$ ($E^4$) is —N— or —CF—, $E^2$ and $E^3$ ($E^5$ and $E^6$) must be —CH—,
  if $E^2$ and/or $E^3$ ($E^5$ and/or $E^6$) are —CF—, $E^1$ ($E^4$) must be —CH—;
  if $E^2$ ($E^5$) is —N—, $E^1$ ($E^4$) must be —CH—, while $E^3$ ($E^5$) can be —CH— or —CF—;
  and at least one of $E^1$ to $E^6$ must be —N— or —CF—;

G is —CH$_2$CH$_2$— or —CH—CH—;

$R^1$ and $R^2$, independently of one another, are
  (a) a hydrogen atom, —F, —Cl, —CN, —CF$_3$ or —OCF$_3$,
  (b) a straight-chain or branched-chain alkyl group (with or without an asymmetric carbon atom) having from 1 to 20 carbon atoms, in which
    b1) one or more non-adjacent and non-terminal —CH$_2$— groups may be replaced by —O—, —S—, —CO—, —CO—O—, —O—CO—, —O—CO—O— or —Si(CH$_3$)$_2$— and/or
    b2) one or more —CH$_2$— groups may be replaced by —CH=CH—, —C≡C—, 1,4-cyclohexylene, 1,4-phenylene, cyclopropane-1,2-diyl or 1,3-cyclopentylene and/or
    b3) one or more hydrogen atoms of the alkyl group may be substituted by F and/or Cl and/or
    b4) the terminal CH$_3$-group may be replaced by any one of the following chiral groups (optically active or racemic):

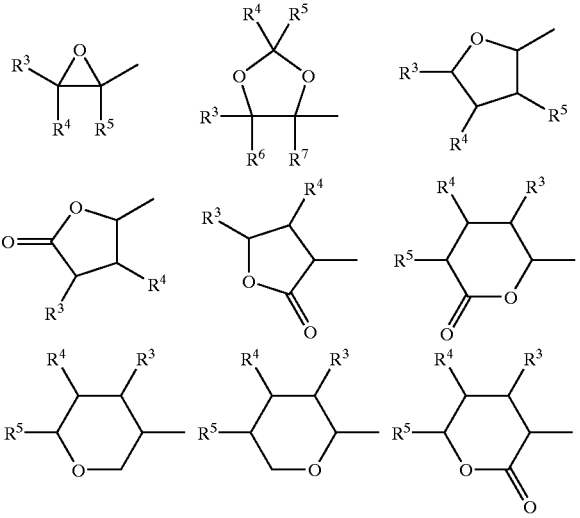

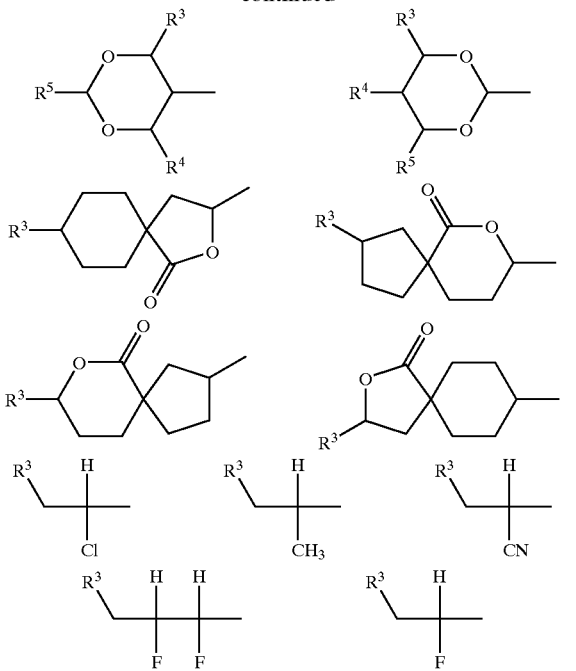

with the proviso that only one of $R^1$, $R^2$ can be a hydrogen atom, —F, —Cl, —CN, —$CF_3$ or —$OCF_3$;

$R^3$, $R^4$, $R^5$, $R^6$, $R^7$, independently of one another, are
a) a hydrogen atom,
b) a straight-chain or branched-chain alkyl group (with or without an asymmetric carbon atom) having from 1 to 16 carbon atoms, where
  b1) one or more non-adjacent and non-terminal —$CH_2$— groups may be replaced by —O— and/or
  b2) one or two —$CH_2$— groups may be replaced by —CH=CH— and/or
  b3) one or more hydrogen atoms of the alkyl group may be substituted by F or Cl,
c) $R^4$ and $R^5$ may also together be —$(CH_2)_4$— or —$(CH_2)_5$— if they are bonded to an oxirane, dioxolane, tetrahydrofuran, tetrahydropyrane, butyrolactone or valerolactone system;

$M^1$, $M^2$, independently of one another, are
—CO—O—, —O—CO—, —$CH_2$O—, —O—$CH_2$, —$CH_2$—$CH_2$—, —CH=CH—, —C≡C—, —$CH_2$—$CH_2$—CO—O—, —O—CO—$CH_2$—$CH_2$— or a single bond;

$A^1$, $A^2$, independently of one another, are
1,4-phenylene, in which one or more H atoms may be replaced by F, Cl and/or CN, pyridine-2,5-diyl, in which one H atom may be replaced by F, pyrimidine-2,5-diyl, pyrazine-2,5-diyl, in which one H atom may be replaced by F, pyridazin-3,6-diyl, in which one H atom may be replaced by F, 1,4-cyclohexylene in which one or two hydrogen atoms may be substituted by CN and/or F and/or $CH_3$, thiophene-2,5-diyl, [1,3,4]-thiadiazole-2,5-diyl, [1,31]-thiazole-2,4-diyl, [1,3]-thiazole-2,5-diyl or 1,3-dioxane-2,5-diyl;

a, b are 0 or 1 with the proviso, that compounds of the formula (II) do not contain more than three five- or six-membered ring systems;

C. 2-fluoropyridine derivatives of the formula (III),

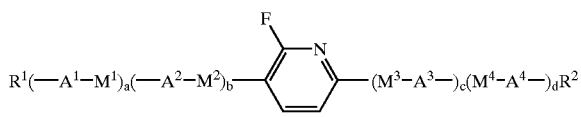

(III)

in which the symbols and indices have the following meanings:

$R^1$ and $R^2_1$ independently of one another, are
(a) a hydrogen atom, —F, —Cl, —CN, —$CF_3$ or —$OCF_3$,
(b) a straight-chain or branched-chain alkyl group (with or without an asymmetric carbon atom) having from 1 to 20 carbon atoms, in which
  b1) one or more non-adjacent and non-terminal —$CH_2$— groups may be replaced by —O—, —S—, —CO—, —CO—O—, —O—CO—, —O—CO—O— or —Si($CH_3$)$_2$— and/or
  b2) one or more —$CH_2$— groups may be replaced by —CH=CH—, —C≡C—, 1,4-cyclohexylene, 1,4-phenylene, cyclopropane-1,2-diyl or 1,3-cyclopentylene and/or
  b3) one or more hydrogen atoms of the alkyl group may be substituted by F and/or Cl and/or
  b4) the terminal $CH_3$-group may be replaced by any one of the following chiral groups (optically active or racemic):

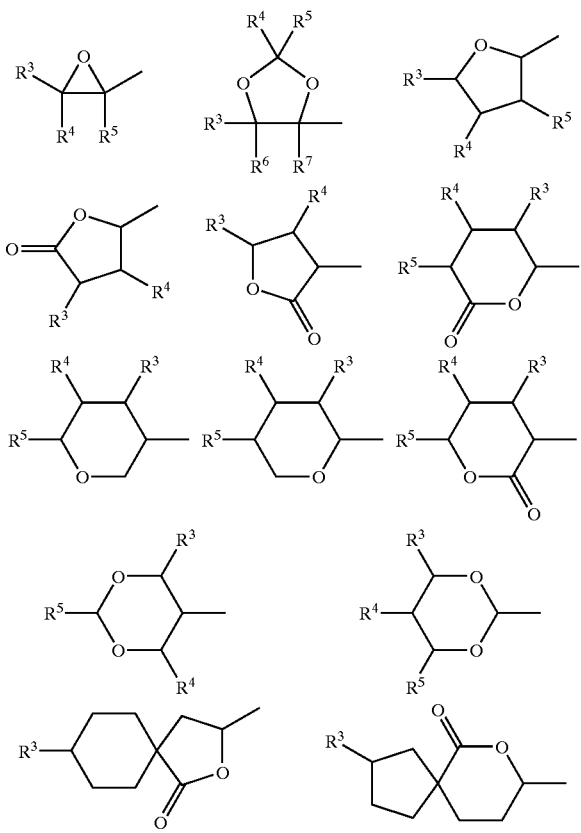

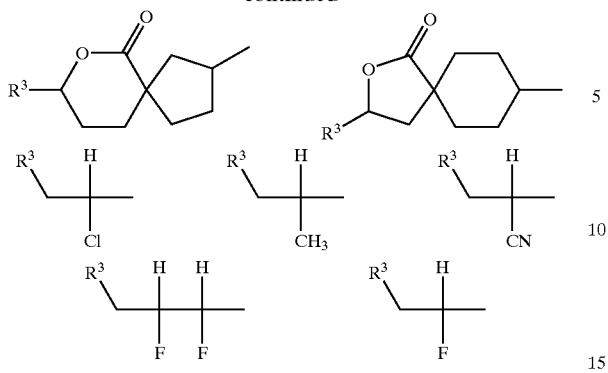

with the proviso that only one of $R^1$, $R^2$ can be a hydrogen atom, —F, —Cl, —CN, —$CF_3$ or —$OCF_3$;

$R^3$, $R^4$, $R^5$, $R^6$, $R^7$, independently of one another, are
  a) a hydrogen atom,
  b) a straight-chain or branched-chain alkyl group (with or without an asymmetric carbon atom) having from 1 to 16 carbon atoms, where
    b1) one or more non-adjacent and non-terminal —$CH_2$— groups may be replaced by —O— and/or
    b2) one or two —$CH_2$— groups may be replaced by —CH=CH— and/or
    b3) one or more hydrogen atoms of the alkyl group may be substituted by F or Cl,
  c) $R^4$ and $R^6$ may also together be —$(CH_2)_4$— or —$(CH_2)_5$— if they are bonded to an oxirane, dioxolane, tetrahydrofuran, tetrahydropyrane, butyrolactone or valerolactone system;

$M^1$, $M^2$, $M^3$, $M^4$, independently of one another, are —CO—O—, —O—CO—, —$CH_2$—O—, —O—$CH_2$—, —$CH_2$—$CH_2$—, —CH=CH—, —C≡C—, —$CH_2$—$CH_2$—CO—O—, —O—CO—$CH_2CH_2$— or a single bond;

$A^1$, $A^2$, $A^3$, $A^4{}_1$ independently of one another, are 1,4phenylene, in which one or more H atoms may be replaced by F, Cl and/or CN, pyridine-2,5-diyl, in which one H atom may be replaced by F, pyrimidine-2,5-diyl, pyrazine-2,5-diyl, in which one H atom may be replaced by F, pyridazin-3,6-diyl, in which one H atom may be replaced by F, 1,4-cyclohexylene in which one or two hydrogen atoms may be substituted by CN and/or F and/or $CH_3$, naphthalene-2,6-diyl in which one or more H atoms may be replaced by F, Cl and/or CN, thiophene-2,5-diyl, [1,3,4]-thiadiazole-2,5-diyl, [1,3]-thiazole-2,4-diyl, [1,31]-thiazole-2,5-diyl or 1,3-dioxane-2,5-diyl;

a, b, c, d are 0 or 1 with the proviso, that compounds of the formula (III) do not contain more than four five or six-membered ring systems;

D. phenylene derivatives of the formula (IV), (IV)

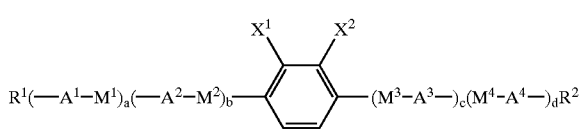

in which the symbols and indices have the following meanings:

$R^1$ and $R^2$, independently of one another, are
  (a) a hydrogen atom, —F, —Cl, —CN, —$CF_3$ or —$OCF_3$,
  (b) a straight-chain or branched-chain alkyl group (with or without an asymmetric carbon atom) having from 1 to 20 carbon atoms, in which
    b1) one or more non-adjacent and non-terminal —$CH_2$— groups may be replaced by —O—, —S—, —CO—, —CO—O—, —O—CO—, —O—CO—O— or —Si$(CH_3)_2$— and/or
    b2) one or more —$CH_2$— groups may be replaced by —CH=CH—, —C≡C—, 1,4-cyclohexylene, 1,4-phenylene, cyclopropane-1,2-diyl or 1,3-cyclopentylene and/or
    b3) one or more hydrogen atoms of the alkyl group may be substituted by F and/or Cl and/or
    b4) the terminal $CH_3$-group may be replaced by any one of the following chiral groups (optically active or racemic):

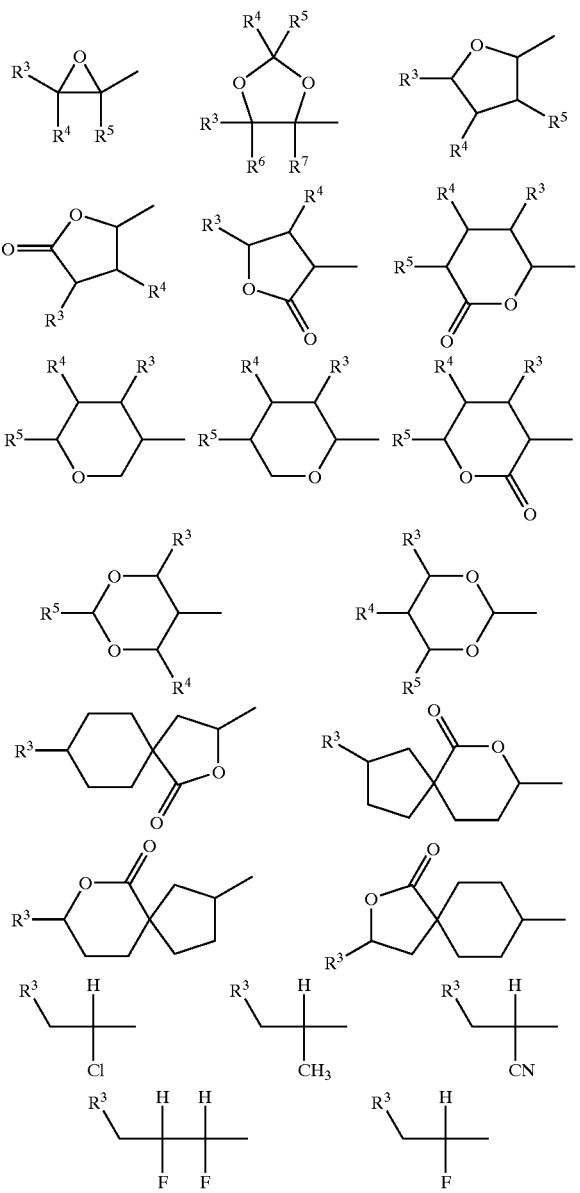

with the proviso that only one of $R^1$, $R^2$ can be a hydrogen atom, —F, —Cl, —CN, —$CF_3$ or —OCF;

$R^3$, $R^4$, $R^5$, $R^6$, $R^7$, independently of one another, are
a) a hydrogen atom,
b) a straight-chain or branched chain alkyl group (with or without asymmetric carbon atoms) having from 1 to 16 carbon atoms, where
b1) one or more non-adjacent and non-terminal —$CH_2$— groups may be replaced by —O— and/or
b2) one or two —$CH_2$— groups may be replaced by —CH=CH— and/or
b3) one or more hydrogen atoms of the alkyl group may be substituted by F or Cl,
c) $R^4$ and $R^5$ may also together be —$(CH_2)_4$— or —$(CH_2)_5$— if they are bonded to an oxirane, dioxolane, tetrahydrofuran tetrahydropyrane, butyrolactone or valerolactone system;

$X^1$ and $X^2$, independently of one another, are hydrogen, F, Cl, $CF_3$ or CN, with the proviso that $X^1$ and $x^2$ are not simultaneously hydrogen;

$M^1$, $M^2$, $M^3$, $M^4$, independently of one another, are —CO—O—, —O—CO—, —$CH_2$—O—, —O—$CH_2$, —$CH_2$—$CH_2$—, —CH=CH—, —C≡C—, —$CH_2$—$CH_2$—CO—O—, —O—CO—$CH_2CH_2$— or a single bond;

$A^1$, $A^2$, $A^4$, independently of one another, are 1,4-phenylene, in which one or more H atoms may be replaced by F, Cl and/or CN, pyridine-2,5-diyl, in which one H atom may be replaced by F, pyrimidine-2,5-diyl, pyrazine-2,5-diyl, in which one H atom may be replaced by F, pyridazin-3,6-diyl, in which one H atom may be replaced by F, 1,4-cyclohexylene in which one or two hydrogen atoms may be substituted by CN and/or F and/or $CH_3$, naphthalene-2,6-diyl in which one or more H atoms may be replaced by F, Cl and/or CN, 1,2,3,4-tetrahydronapthalene-2,6-diyl, thiophene-2,5-diyl, [3,4]-thiadiazole-2,5-diyl, [1,3]-thiazole-2,4-diyl, [1,3]-thiazole-2,5-diyl or 1,3-dioxane-2,5-diyl;

a, b, c, d are 0 or 1 with the proviso, that compounds of the formula (IV) do not contain more than four five- or six-membered ring systems;

E. meta-substituted aromatic compounds of the formula (V):

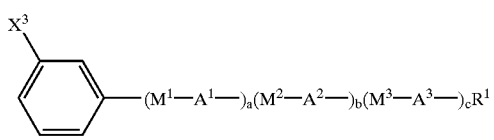

(V)

wherein the symbols and indices have the following meanings:

$X^3$ is
(a) —F, —Cl, —Br, —CN, —$CF_3$ or —$OCF_3$,
(b) a straight-chain or branched-chain alkyl group (with or without an asymmetric carbon atom) having from 1 to 12 carbon atoms, in which
b1) one or two non-adjacent and non-terminal —$CH_2$— groups may be replaced by —O—, —S—, —CO—, —CO—O— or —O—CO— and/or
b2) one or more hydrogen atoms of the alkyl group may be substituted by F and/or Cl and/or CN;

$R^1$ is
(a) a hydrogen atom, —F, —Cl, —CN, —$CF_3$ or —$OCF_3$, (b) a straight-chain or branched-chain alkyl group (with or without an asymmetric carbon atom) having from 1 to 20 carbon atoms, in which
b1) one or more non-adjacent and non-terminal —$CH_2$— groups may be replaced by —O—, —S—, —CO—, —CO—O—, —O—CO—, —O—CO—O— or —$Si(CH_3)_2$— and/or
b2) one or more —$CH_2$— groups may be replaced by —CH=CH—, —C≡C—, 1,4-cyclohexylene, 1,4-phenylene, cyclopropane-1,2-diyl or 1,3-cyclopentylene and/or
b3) one or more hydrogen atoms of the alkyl group may be substituted by F and/or Cl and/or
b4) the terminal $CH_3$-group may be replaced by any one of the following chiral groups (optically active or racemic):

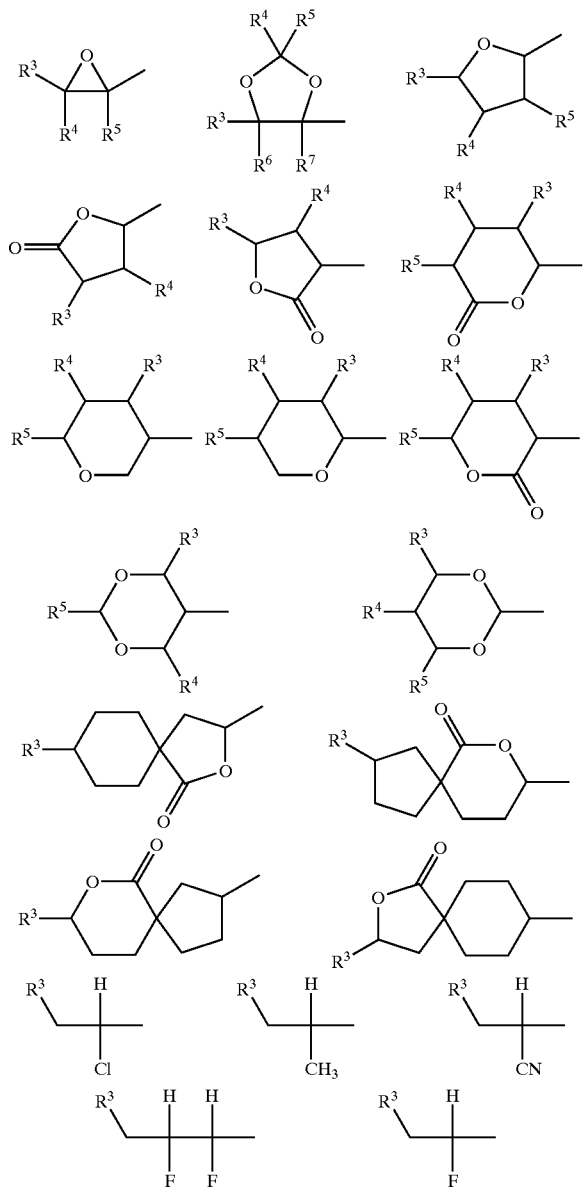

with the proviso that $R^1$ can not be a hydrogen atom, —F, —Cl, —CN, —$CF_3$ or —$OCF_3$ if $X^3$ is —F, —Cl, —Br, —CN, —$CF_3$ or —$OCF_3$;

$R^3$, $R^4$, $R^5$, $R^6$, $R^7$, independently of one another, are
a) a hydrogen atom,
b) a straight-chain or branched-chain alkyl group (with or without an asymmetric carbon atom) having from 1 to 16 carbon atoms, where
b1) one or more non-adjacent and non-terminal —$CH_2$— groups may be replaced by —O— and/or
b2) one or two —$CH_2$— groups may be replaced by —CH=CH— and/or
b3) one or more hydrogen atoms of the alkyl group may be substituted by F or Cl,
c) $R^4$ and $R^5$ may also together be —$(CH_2)_4$— or —$(CH_2)_5$— if they are bonded to an oxirane, dioxolane, tetrahydrofuran, tetrahydropyrane, butyrolactone or valerolactone system;
$M^1$, $M^2$, $M^3$, independently of one another, are —CO—O—, —O—CO—, —$CH_2$—O—, —O—$CH_2$—, —$CH_2$—$CH_2$—, —CH=CH—, —C≡C—, —$CH_2CH_2$—CO—O—, —O—CO—$CH_2CH_2$— or a single bond;
$A^1$, $A^2$, $A^3$, independently of one another, are 1,4-phenylene, in which one or more H atoms may be replaced by F, Cl and/or CN, pyridine-2,5-diyl, in which one H atom may be replaced by F, pyrimidine-2,5-diyl, pyrazine-2,5-diyl, in which one H atom may be replaced by F, pyridazin-3,6-diyl, in which one H atom may be replaced by F, 1,4-cyclohexylene in which one or two hydrogen atoms may be substituted by CN and/or F and/or $CH_3$, naphthalene-2,6-diyl in which one or more H atoms may be replaced by F, Cl and/or CN, thiophene-2,5-diyl, [1,3,4]-thiadiazole-2,5-diyl, [1,3]-thiazole-2,4-diyl, [1,3]-thiazole-2,5-diyl or 1,3-dioxane-2,5-diyl;
a, b, c are 0 or 1 with the proviso, that compounds of the formula (V) do; not contain more than four five- or six-membered ring systems;

F. (1,3,4)-thiadiazoles of the formula (I):

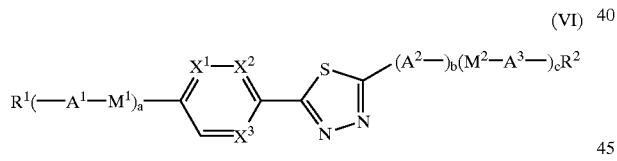

(VI)

wherein the symbols and indices have the following meanings:
$R^1$ and $R^2$, independently of one another, are
(a) a hydrogen atom, —F, —Cl, —CN, —$CF_3$ or —$OCF_3$,
(b) a straight-chain or branched-chain alkyl group (with or without an asymmetric carbon atom) having from 1 to 20 carbon atoms, in which
b1) one or more non-adjacent and non-terminal —$CH_2$— groups may be replaced by —O—, —S—, —CO, —CO—O—, —O—CO—, —O—CO—O— or —Si$(CH_3)_2$— and/or
b2) one or more —$CH_2$— groups may be replaced by —CH=CH—, —C≡C—, 1,4-cyclohexylene, 1,4-phenylene, cyclopropane-1,2-diyl or 1,3-cyclopentylene and/or
b3) one or more hydrogen atoms of the alkyl group may be substituted by F and/or Cl and/or
b4) the terminal $CH_3$-group may be replaced by any one of the following chiral groups (optically active or racemic):

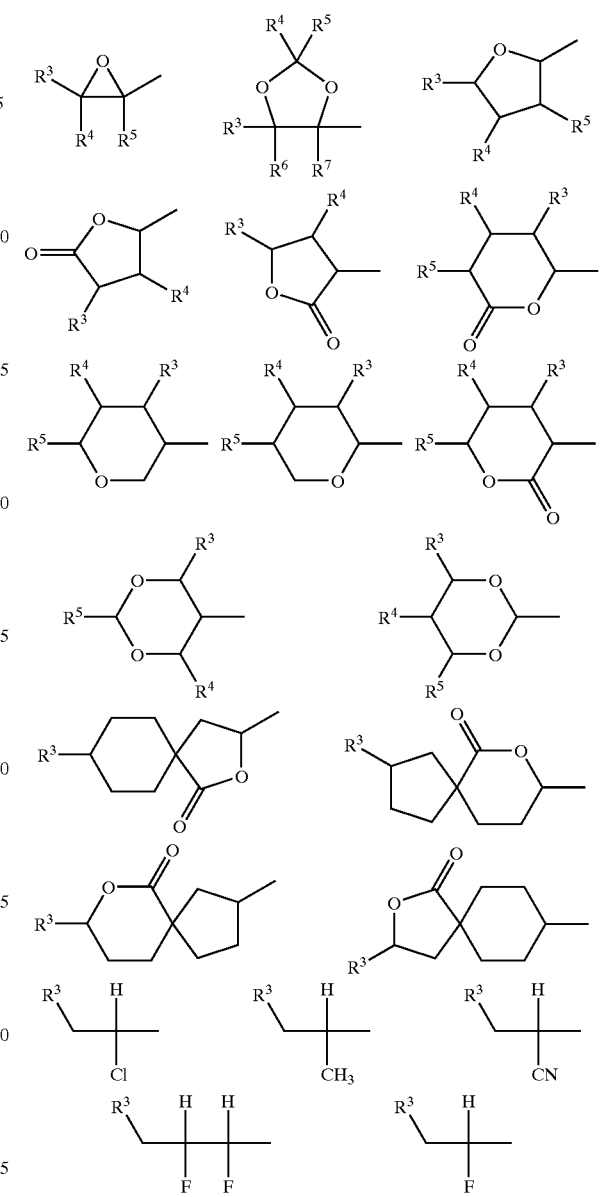

with the proviso that only one of $R^1$, $R^2$ can be a hydrogen atom, —F, —Cl, —CN, —$CF_3$ or —$OCF_3$;
$R^3$, $R^4$, $R^5$, $R^6$, $R^7$, independently of one another, are
a) a hydrogen atom,
b) a straight-chain or branched-chain alkyl group (with or without an asymmetric carbon atom) having from 1 to 16 carbon atoms, where
b1) one or more non-adjacent and non-terminal —$CH_2$— groups may be replaced by —O— and/or
b2) one or to —$CH_2$— groups may be replaced by —CH=CH— and/or
b3) one or more hydrogen atoms of the alkyl group may be substituted by F or Cl,
c) $R^4$ and $R^5$ may also together be —$(CH_2)_4$— or —$(CH_2)_5$— if they are bonded to an oxirane, dioxolane, tetrahydrofuran, tetrahydropyrane, butyrolactone or valerolactone system;
$X^1$, $X^2$, $X^3$, independently of one another, are —CF—, —N— or —CH—;

$M^1$, $M^2$, independently of one another, are
—CO—O—, —O—CO—, —CH$_2$—O—, —O—CH$_2$—, —CH$_2$—CH$_2$—, —CH=CH—, —C≡C—, —CH$_2$—CH$_2$—CO—O—, —O—CO—CH$_2$—CH$_2$— or a single bond;

$A^1$, $A^2$, $A^3$, independently of one another, are
1,4-phenylene, in which one or more H atoms may be replaced by F, Cl and/or CN, pyridine-2,5-diyl, in which one H atom may be replaced by F, pyrimidine-2,5-diyl, pyrazine-2,5-diyl, in which one H atom may be replaced by F, pyridazin-3,6-diyl, in which one H atom may be replaced by F, 1,4-cyclohexylene in which one or two hydrogen atoms may be substituted by CN and/or F and/or CH$_3$, naphthalene-2,6-diyl in which one or more H atoms may be replaced by F, Cl and/or CN, thiophene-2,5-diyl, [1,3,4]-thiadiazole-2,5-diyl, [1,31]-thiazole-2,4-diyl, [1,3]-thiazole-2,5-diyl or 1,3-dioxane-2,5-diyl;

a, b, c are 0 or 1 with the proviso, that compounds of the formula (VI) do not contain more than four five- or six-membered ring systems;

G. 4-cyanocyclohexyls of the formula (VII):

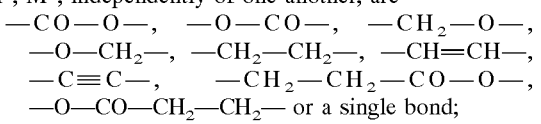

(VII)

wherein the symbols and indices have the following meanings:

$R^1$ is
(a) a hydrogen atom, —F, —Cl, —CN, —CF$_3$ or —OCF$_3$,
(b) a straight-chain or branched-chain alkyl group (with or without an asymmetric carbon atom) having from 1 to 20 carbon atoms, in which
b1) one or more non-adjacent and non-terminal —CH$_2$— groups may be replaced by —O—, —S—, —CO—, —CO—O—, —O—CO—, —O—CO—O— or —Si(CH$_3$)$_2$— and/or
b2) one or more —CH$_2$— groups may be replaced by —CH=CH—, —C≡C—, 1,4-cyclohexylene, 1,4-phenylene, cyclopropane-1,2-diyl or 1,3-cyclopentylene and/or
b3) one or more hydrogen atoms of the alkyl group may be substituted by F and/or Cl and/or
b4) the terminal CH$_3$ group may be replaced by any one of the following chiral groups (optically active or racemic):

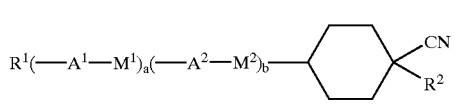

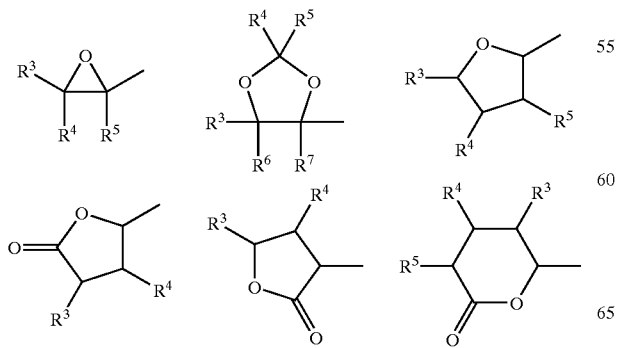

$R^2$ is
(a) a straight-chain or branched-chain alkyl group (with or without an asymmetric carbon atom), having from 1 to 16 carbon atoms, in which
a1) one or two non-adjacent and non-terminal —CH$_2$— groups may be replaced by —O—, —S—, —CO—, —CO—O—, —O—CO— or —Si(CH$_3$)$_2$— and/or
a2) one or two —CH$_2$— groups may be replaced by —CH=CH—, —C≡C— and/or
a3) one or more hydrogen atoms of the alkyl group may be substituted by F and/or Cl and/or CN and/or CF$_3$;

$R^3$, $R^4$, $R^5$, $R^6$, $R^7$, independently of one another, are
a) a hydrogen atom,
b) a straight-chain or branched-chain alkyl group (with or without an asymmetric carbon atom) having from 1 to 16 carbon atoms, where
b1) one or more non-adjacent and non-terminal —CH$_2$— groups may be replaced by —O— and/or
b2) one or two —CH$_2$— groups may be replaced by —CH=CH— and/or
b3) one or more hydrogen atoms of the alkyl group may be substituted by F or C,
c) $R^4$ and $R^5$ may also together be —(CH$_2$)$_4$— or —(CH$_2$)$_5$— if they are bonded to an oxirane, dioxolane, tetrahydrofuran, tetrahydropyrane, butyrolactone or valerolactone system;

$M^1$, $M^2$, independently of one another, are
—CO—O—, —O—CO—, —CH$_2$—O—, —O—CH$_2$—, —CH$_2$—CH$_2$—, —CH=CH—, —C≡C—, —CH$_2$—CH$_2$—CO—O—, —O—CO—CH$_2$—CH$_2$— or a single bond;

$A^1$, $A^2$, independently of one another, are
  1,4-phenylene, in which one or more H atoms may be replaced by F, Cl and/or CN, pyridine-2,5-diyl, in which one H atom may be replaced by F, pyrimidine-2,5-diyl, pyrazine-2,5-diyl, in which one H atom may be replaced by F, pyridazin-3,6-diyl, in which one H atom may be replaced by F, 1,4-cyclohexylene in which one or two hydrogen atoms may be substituted by CN and/or F and/or $CH_3$, naphthalene-2,6-diyl in which one or more H atoms may be replaced by F, Cl and/or CN, thiophene-2,5-diyl, [1,3,4]-thiadiazole-2,5-diyl, [1,3]-thiazole-2,4-diyl, [1,3]-thiazole-2,5-diyl or 1,3-dioxane-2,5-diyl;
a, b are 0 or 1 with the proviso, that compounds of the formula (VII) do not contain more than four five- or six-membered ring systems.

2. The mixture as claimed in claim 1 comprising 2 to 35 compounds of groups A to G.

3. The mixture as claimed in claim 1, comprising at least 5% by weight of compounds of group A to G.

4. The mixture as claimed in claim 1, comprising a combination of compounds selected from each group:

| a) A + B | b) A + C | c) A + D |
| d) A + E | e) A + F | f) A + G. |

5. The mixture as claimed in claim 1, comprising a combination of compounds selected from each group:

| a) A + B + C | b) A + B + D | c) A + B + E | d) A + B + F |
| e) A + B + G | f) A + C + D | g) A + C + E | h) A + C + F |
| i) A + C + G | j) A + D + E | k) A + D + F | l) A + D + G |
| m) A + E + F | n) A + E + G | o) A + F + G. | |

6. The mixture as claimed in claim 1, comprising a combination of compounds from each group:

| a) A + B + C + D | b) A + B + C + E | c) A + B + C + F |
| d) A + B + C + G | e) A + B + D + E | f) A + B + D + F |
| g) A + B + D + G | h) A + B + E + F | i) A + B + E + G |
| j) A + B + F + G | k) A + C + D + E | l) A + C + D + F |
| m) A + C + D + G | n) A + C + E + F | o) A + C + E + G |
| p) A + C + F + G | q) A + D + E + F | r) A + D + E + G |
| s) A + D + F + G | t) A + E + F + G. | |

7. The mixture as claimed in claim 1, wherein the compound A of the formula (I) is a fluorinated derivative of indane of the formula (IA)

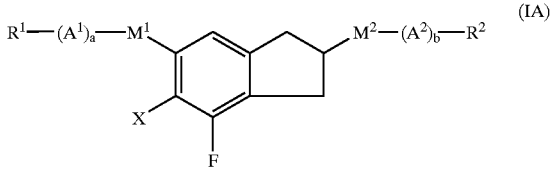

(IA)

wherein the symbols and indices have the following meanings:

$R^5$: Hydrogen or a straight-chain or branched-chain alkyl group (with or without an asymmetric carbon atom) having from 1 to 20 carbon atoms, in which one or more non-adjacent and non-terminal $CH_2$-groups may be replaced by —O—, —CO—O—, —O—CO—, —OC(=O)O— or —Si(CH_3)_2— and one or more hydrogen atoms may be substituted by F, and $R^1$ can be hydrogen only if a is not zero;

$R^2$: Hydrogen or a straight-chain or branched-chain alkyl group (with or without an asymmetric carbon atom) having from 1 to 20 carbon atoms, in which one non-terminal $CH_2$-group may be replaced by —O— and one or more hydrogen atoms may be substituted by F, and $R^2$ can be hydrogen only if d is not zero, $M^1$: —CO—O—, —O—CO—, —$CH_2$—O—, —O—$CH_2$—, —$CH_2CH_2$—, —C≡C— or a single bond $M^2$: —$CH_2CH_2$— or a single bond $A^1$: 1,4-phenylene, in which one or two H atoms may be replaced by F, pyridine-2,5-diyl, in which on H atom may be replaced by F, pyrimidine-2,5-diyl, wherein one H atom may be replaced by F, 1,4-cyclohexylene, 4'-(4-$R^1$-cyclohexyl)phenylene, 4-biphenyl-4'-yl, in which one or two H-atoms may be replaced by F, or 4-(1-$R^1$-silacyclohexane-4-yl)phenylene $A^2$: 1,4-cyclohexylene or 1,4-phenylene, in which one or two H-atoms may be replaced by F X: H or F a,b: zero or 1, wherein the sum (a+b) is at least 1.

8. The mixture as claimed in claim 7, wherein the symbols and indices of the formula (IA) have one ore more of the following meanings:

$R^1$, $R^2$ are the same or different
  a) a straight-chain or branched-chain alkyl group (with or without an asymmetric carbon atom) having from 1 to 18 carbon atoms, where
  b) one non-terminal $CH_2$-group may be replaced by —O—,
  c) one or more H-atoms may be replaced by F;

$M^1$ is —$CH_2CH_2$—, —C≡C— or a single bond;

$A^1$ is -1,4 phenylene, in which 1 or two H-atoms may be replaced by F, pyridine-2,5-diyl, wherein one H-atom may be replaced by F, or pyrimidine-2,5-diyl;

$A^2$ is 1,4-cyclohexylene;

X is H;

a is one and b is zero.

9. The mixture as claimed in claim 7, wherein the compound of the formula (IA) is selected from the group consisting of the following compounds of the formulae (Ia) to (In)

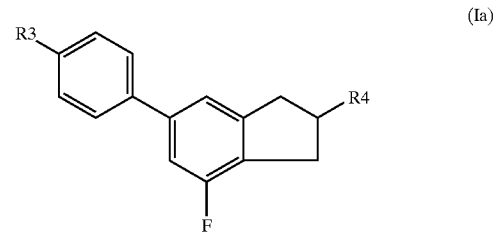

(Ia)

-continued (Ib) 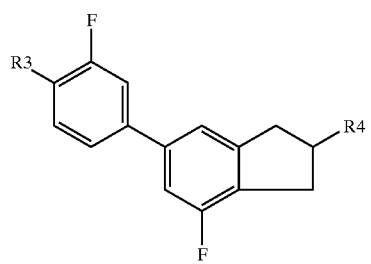

(Ic) 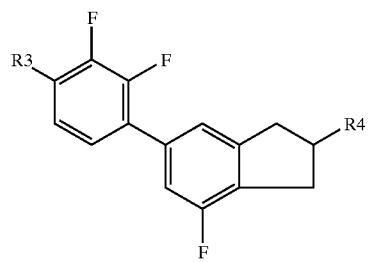

(Id) 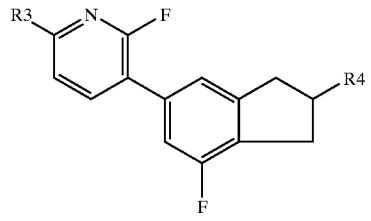

(Ie) 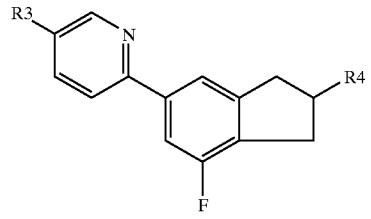

(If) 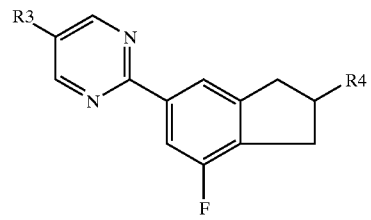

(Ig) 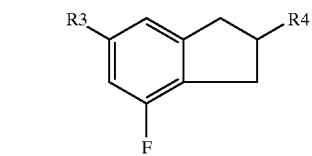

(Ih) 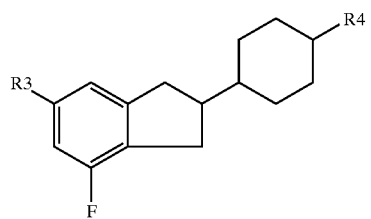

-continued (Ii) 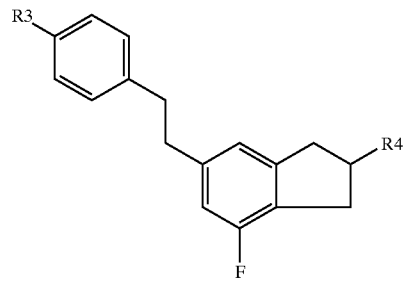

(Ik) 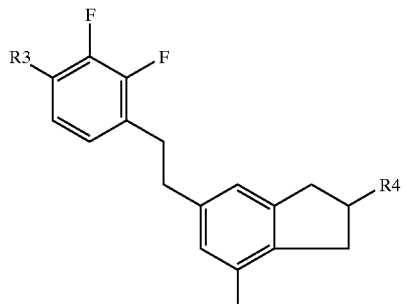

(Il) 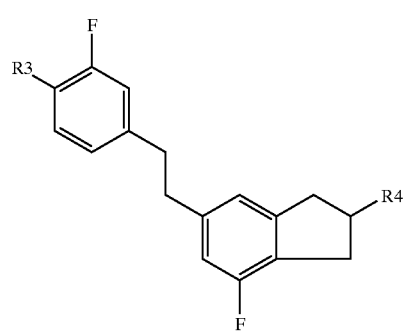

(Im) 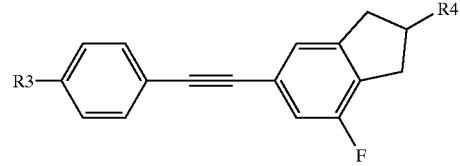

(In) 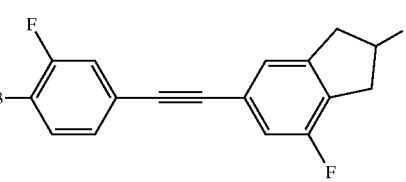

wherein $R^3$ is a straight-chain or branched-chain alkyl or alkyloxygroup having from 1 to 12 carbon atoms, and $R^4$ is a straight-chain or branched-chain alkyl group having from 1 to 12 carbon atoms.

10. A ferroelectric liquid crystal display device comprising a mixture as claimed in claim 1.

11. The device as claimed in claim 10 which is operated in the $\tau V_{min}$-mode.

12. A fluorinated derivative of indane of the formula (1A)

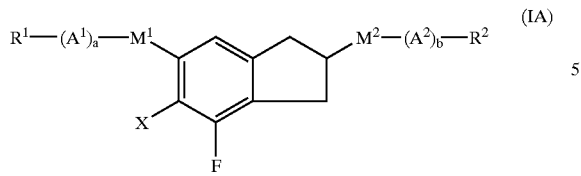

wherein the symbols and indices have the following meanings:

$R^1$: Hydrogen or a straight-chain or branched-chain alkyl group (with or without an asymmetric carbon atom) having from 1 to 20 carbon atoms, in which one or more non-adjacent and non-terminal $CH_2$-groups may be replaced by —O—, —CO—O—, —O—CO—, —OC(=O)O— or —Si(CH$_3$)$_2$— and one or more hydrogen atoms may be substituted by F, and $R^1$ can be hydrogen only if a is not zero;

$R^2$: Hydrogen or a straight-chain or branched-chain alkyl group (with or without an asymmetric carbon atom) having from 1 to 20 carbon atoms, in which one non-terminal $CH_2$-group may be replaced by —O— and one or more hydrogen atoms may be substituted by F, and $R^2$ can be hydrogen only if d is not zero, $M^1$: —CO—O—, —O—CO—, —CH$_2$—O—, —O—CH$_2$—, —CH$_2$CH$_2$—, —C≡C— or a single bond $M^2$: —CH$_2$CH$_2$— or a single bond $A^1$: 1,4-phenylene, in which one or two H atoms may be replaced by F, pyridine-2,5-diyl, in which on H atom may be replaced by F, pyrimidine-2,5-diyl. wherein one H atom may be replaced by F, 1,4-cyclohexylene, 4-(4-$R^1$-cyclohexyl)phenylene, 4-biphenyl-4'-yl, in which one or two H-atoms may be replaced by F, or 4-(1-R'-silacyclohexane-4-yl)phenylene $A^2$: 1,4-cyclohexylene or 1,4-phenylene, in which one or two H-atoms may be replaced by F X: H or F a,b: zero or 1, wherein the sum (a+b) is at least 1.

* * * * *